United States Patent
Ashe, III et al.

(10) Patent No.: US 6,284,905 B1
(45) Date of Patent: Sep. 4, 2001

(54) BRIDGED METAL COMPLEXES

(75) Inventors: Arthur J. Ashe, III, Ann Arbor; David D. Devore, Midland, both of MI (US); Xinggao Fang, Los Alamos, NM (US); Kevin A. Frazier, Midland, MI (US); D. Patrick Green, Midland, MI (US); Jasson T. Patton, Midland, MI (US); Francis J. Timmers, Midland, MI (US)

(73) Assignees: The Dow Chemical Company, Midland; The Regents of the University of Michigan, Ann Arbor, both of MI (US)

( * ) Notice: Subject to any disclaimer, the term of this patent is extended or adjusted under 35 U.S.C. 154(b) by 0 days.

(21) Appl. No.: 09/523,428

(22) Filed: Mar. 10, 2000

Related U.S. Application Data

(62) Division of application No. 09/383,996, filed on Aug. 26, 1999, now abandoned.
(60) Provisional application No. 60/103,511, filed on Oct. 8, 1998.

(51) Int. Cl.[7] .............. C07F 17/00; C07F 7/00; B01J 31/00; C08F 4/64

(52) U.S. Cl. ................ 556/7; 556/27; 556/53; 526/161; 526/177; 526/178; 526/186; 526/188; 526/189; 526/198; 526/348; 526/943; 502/103; 502/117; 502/120; 989/2

(58) Field of Search .................... 556/7, 27, 53; 526/161, 177, 178, 186, 188, 189, 198, 348, 943; 502/103, 117, 120; 989/2

(56) References Cited

U.S. PATENT DOCUMENTS 5,399,636  3/1995  Alt et al. .............. 526/129

OTHER PUBLICATIONS

Journal of Organometallic Chemistry, Preparation of some organo–bis(diisopropylamino)boranes and their application to the synthesis of oxazaborolidines, 455, (1993), pp. 37–46.
Inst. For Inorganic Chemistry, Munich Univ., Preparation of dimethylamino–diboron chlorides, $B_2(Nme_2)_{4-n}Cl_n^2$, Noth et al. 714–718, 1962.

*Primary Examiner*—Porfirio Nazario-Gonzalez

(57) ABSTRACT

A Group 4 transition metal complex containing a boron or aluminum bridging group containing a nitrogen containing electron donating group, especially an amido group.

47 Claims, 2 Drawing Sheets

BRIDGED METAL COMPLEXES

CROSS-REFERENCE TO RELATED APPLICATION

This application is a divisional of U.S. application Ser. No. 09/383,996, filed Aug. 26, 1999, now abandoned which claims benefit of priority from provisional application 60/103,511, filed Oct. 8, 1998.

BACKGROUND OF THE INVENTION

This invention relates to certain bridged Group 4 transition metal complexes possessing a unique bridging structure and to olefin polymerization catalysts obtained from such complexes. In one form, this invention embodies Group 4 transition metal complexes containing a unique bridged, or divalent ligand structure having two anionic, delocalized π-bonded ligands attached thereto. In a second embodiment the invention relates to Group 4 transition metal complexes containing a unique bridged ligand containing one of the foregoing anionic, delocalized π-bonded moieties and one anionic amido or phosphido moiety. In a third embodiment the invention relates to Group 4 transition metal complexes containing a unique bridged ligand containing two anionic amido and/or phosphido groups. In all cases the unique bridge consists of either boron or aluminum atoms which are further ligated with nitrogen containing groups.

In *Angew. Chem. Int. Ed. Enal.*, 36, 21, p2338–2340 (1997) and in *Phosphorus, Sulfur, and Silicon*, 124 & 125, p561–565 (1997) amido substituted boron bridged ferrocenophanes useful for forming poly(ferrocenes) by a ring opening polymerization were disclosed. The synthesis and characterization of Group 1 and 2 metal and tin complexes of 1,2-bis(dimethylamino)-1,2-di-9-fluorenyldiboranes were disclosed in *Chem. Ber.*, 127, p1901–1908, (1994). Diboranes having structure similar to those employed in the foregoing study were disclosed by the same researchers in *Eur. J. Inorg. Chem.*, p505–509 (1998). Ferrocenophane derivatives of similar bisboranes for further molecular property studies were disclosed by *J. Organomet. Chem.*, 530 p117–120 (1997). In *Organometallics*, 16, p4546–4550 (1997) boron bridged ansa metallocene complexes including dimethylsulfide and phosphine adducts thereof of possible use in Ziegler-Natta-type olefin polymerizations were disclosed.

In the patent literature, bridged metal complexes for use as olefin polymerization catalyst components, including such complexes containing one or more boron atoms in the bridge are generically disclosed by EP-A-416,815 and WO 98/39369.

SUMMARY OF THE INVENTION

Figure 1:
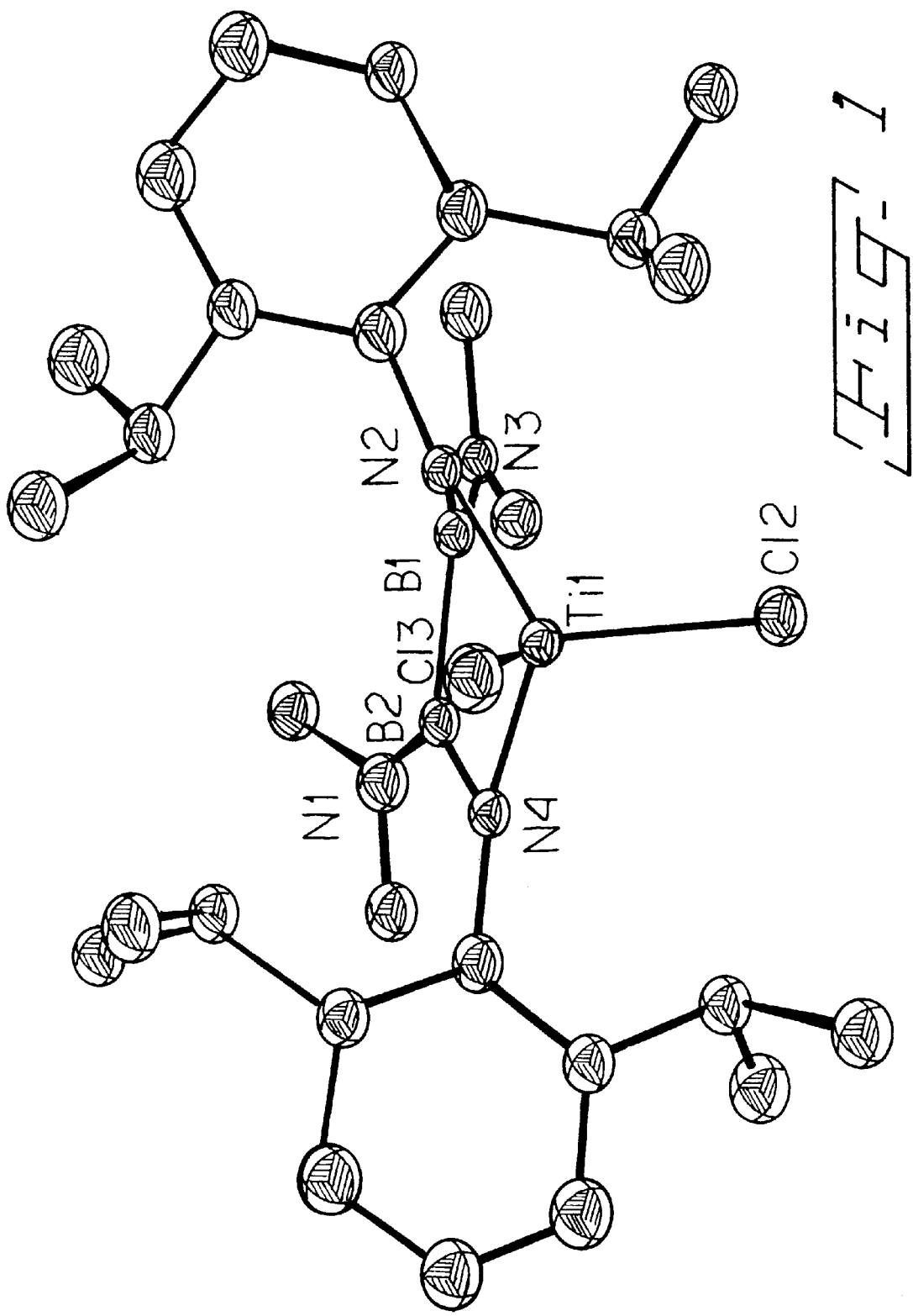
FIGS. 1 and 2 are the crystal structures (ORTEP) of the compounds of Examples 2 and 5 respectively.

The present invention relates to certain bridged Group 4 transition metal complexes and to olefin polymerization catalysts obtained from such, said complexes corresponding to the following formulas:

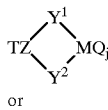

Formula 1 or

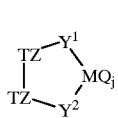

Formula 2 wherein:

M is titanium, zirconium, or hafnium in the +4, +3, or +2 oxidation state;

$Y^1$ and $Y^2$ are independently an anionic, cyclic or non-cyclic, π-bonded group, $NR^1$, $PR^1$; $NR^1_2$ or $PR^1_2$;

Z is boron or aluminum;

Q is a neutral, anionic or dianionic ligand group depending on the oxidation state of M;

j is 1, 2 or 3 depending on the oxidation state of M and the electronic nature of Q;

T independently each occurrence is:

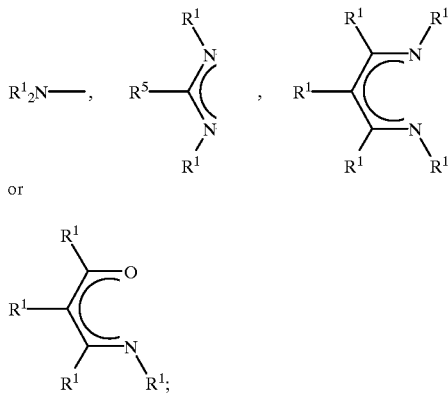

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups together or one or more $R^1$ groups together with $R^5$ may optionally be joined to form a ring structure.

It is understood that the foregoing metal complexes may exist as dimers and that one or more Lewis bases may optionally be coordinated with the complex or the dimer thereof and that when $Y^1$ or $Y^2$ are the neutral ligands, $NR^1_2$ or $PR^1_2$, the bond to M is a coordinate-covalent bond rather than a covalent bond. In addition, when T is $R^1_2N$ and Z is boron, the bond between T and Z, particularly in the compounds of formula 1, may possess double bond characteristics, that is, the resulting group may more accurately depicted by the formula $R^1_2N=B$.

Additionally, according to the present invention there are provided unique ligand structures of the following formulas:

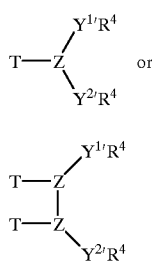

Formula 1A or Formula 2A wherein Z, T, R$^1$ and R$^5$ are as defined above;

Y$^{1'}$ and Y$^{2'}$ are an anionic, cyclic or non-cyclic, π-bonded group, NR$^1$, or PR$^1$; and R$^4$ is hydrogen or a trimethylsilyl group. Such ligand groups of Formula 1A or 2A are readily prepared by contacting sources of the anionic groups (Y$^{1'}$R$^4$)$^-$ and (Y$^{2'}$R$^4$)$^-$, particularly the Grignard or alkali metal salts thereof, with the neutral compound TZY$^3$ or (TZ)$_2$Y$^3_2$, where Y$^3$ is a leaving group, especially halide, either as neat reagents or in an inert solvent, employing temperatures from –100° C. to 150° C.

Additionally, according to the present invention there is provided a process for preparing complexes of formula 1 and formula 2 in high racemic purity in the +2 formal oxidation state by contacting ligand structures of formula 1A or 2A where R$^4$ is trimethylsilyl, or deprotonated dianionic derivatives of ligand structures of formula 1A or formula 2A, with a Group 4 precursor of the formula 3:

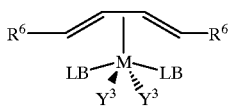

Formula 3 wherein M and Y$^3$ are defined as above,

R$^6$ independently each occurrence is hydrogen, a hydrocarbyl group, a tri(hydrocarbyl)silyl group, or a tri(hydrocarbyl)silylhydrocarbyl group, said R$^6$ groups containing up to 20 atoms not counting hydrogen; and LB is a Lewis base, especially an ether, amine, or phosphine of up to 20 carbons.

The reaction is desirably conducted in an inert solvent, especially an aliphatic or aromatic hydrocarbon or ether, employing temperatures from –100° C. to 150° C. This technique is similar to that disclosed in United States patent application 265,641, filed Mar. 10, 1999, differing in that different starting reagents are employed.

Further according to the present invention there are provided catalyst compositions suitable for the polymerization of addition polymerizable monomers comprising one or more metal complexes of formula 1 or 2 in combination with one or more activating cocatalysts or activated by use of an activating technique.

Finally, according to the present invention there is also provided a polymerization process comprising contacting one or more addition polymerizable monomers with a catalyst composition comprising one or more metal complexes of formula 1 or 2 in combination with one or more activating cocatalysts or activated by use of an activating technique. The polymerization is preferably performed under solution, slurry, suspension, or high pressure process conditions, and the catalyst composition or individual components thereof may be used in a heterogeneous state, that is, a supported state or in a homogeneous state as dictated by process conditions. The catalysts of the present invention can be used in combination with one or more additional catalysts of the same or different nature either simultaneously or sequentially in the same or in separate reactors.

Catalyst compositions according to the present invention possess improved catalytic efficiencies and improved thermal stability allowing for use under higher operating temperatures compared to catalysts comprising conventional metal complexes.

DETAILED DESCRIPTION

All references to the Periodic Table of the Elements herein shall refer to the Periodic Table of the Elements, published and copyrighted by CRC Press, Inc., 1997. Also, any references to a Group or Groups shall be to the Groups or Groups reflected in this Periodic Table of the Elements using the IUPAC system for numbering groups. Where any reference is made herein to any publication, patent application or provisional patent application, the contents thereof are incorporated herein in its entirety by reference. By the term "π-bonded" as used herein is meant that bonding occurs through an interaction involving delocalized electrons. Finally, by the term, "leaving group" is meant a ligand that is readily displaced by another ligand under ligand exchange conditions.

The present Group 4 transition metal complexes contain a unique bridging group: (T-Z) or (T-Z)$_2$, which imparts improved catalytic properties when used in combination with one or more activating cocatalysts or activating techniques in the presence of addition polymerizable monomers. While not desiring to be bound by theory, it is believed that the improvement in catalytic properties for such complexes may be due to the electronic properties of the ZT, Y$^1$ and Y$^2$ moieties.

Preferred Group 4 transition metal complexes of the present invention which correspond to formula 1 or 2 are represented in formulas 4, 5, 6, 7, 8 and 9:

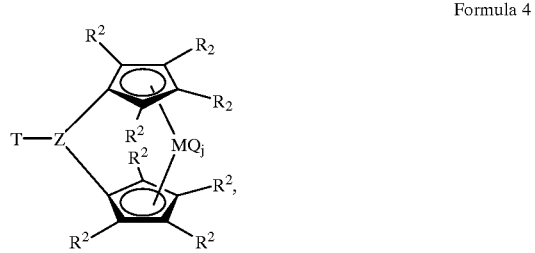

Formula 4

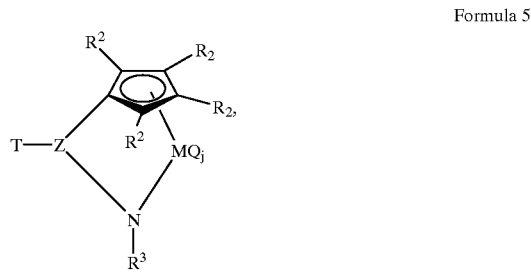

Formula 5

-continued

Formula 6
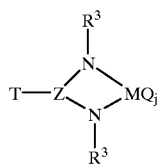

Formula 7
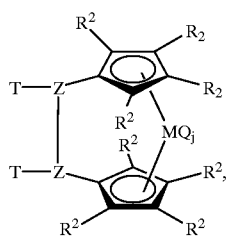

Formula 8
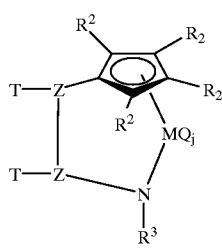

or

Formula 9
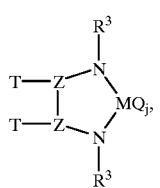

wherein M, Z, T, Q and j are as defined above;

$R^2$ is hydrogen, or a hydrocarbyl, halohydrocarbyl, dihydrocarbylamino-hydrocarbyl, tri(hydrocarbyisilyl)hydrocarbyl, $Si(R^3)_3$, $N(R^3)_2$, or $OR^3$ group of up to 20 carbon or silicon atoms, and optionally two adjacent $R^2$ groups can be joined together, thereby forming a fused ring structure, especially an indenyl ligand or a substituted indenyl ligand; and $R^3$ is independently hydrogen, a hydrocarbyl group, a trihydrocarbylsilyl group or a trihydrocarbylsilylhydrocarbyl group, said $R^3$ having up to 20 atoms not counting hydrogen.

When M is in the +4 oxidation state, j=2 and Q independently each occurrence is halide, hydride, hydrocarbyl, silylhydrocarbyl, hydrocarbyloxide, dihydrocarbylamide, said Q having up to 20 atoms not counting hydrogen. Alternatively, two Q groups may be joined together to form an alkanediyl group or a conjugated $C_{4-40}$ diene ligand which is coordinated to M in a metallocyclopentene fashion.

When M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, and being further substituted with an amine, phosphine, ether, or thioether containing substituent able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$ bond with M.

When M is in the +2 oxidation state, j=1 and Q is a neutral conjugated diene, optionally substituted with one or more tri(hydrocarbyl)silyl or tri(hydrocarbylsilyl)hydrocarbyl groups, said Q having up to 40 carbon atoms and forming a π-complex with M.

Specific examples of the above metal complexes wherein M is in the +4 oxidation state are shown below in formulas 4a–9a, wherein the definitions of M, Z, $R^1$, $R^2$, and $R^3$ are as defined above:

Formula 4a
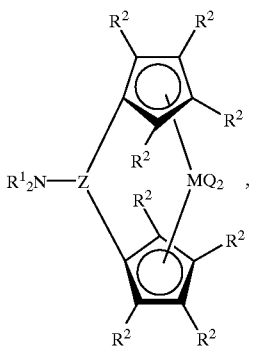

Formula 5a
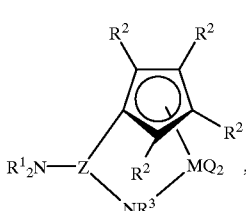

Formula 6a
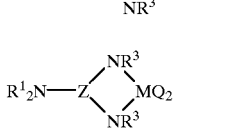

Formula 7a
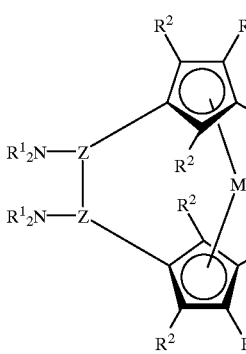

Formula 8a
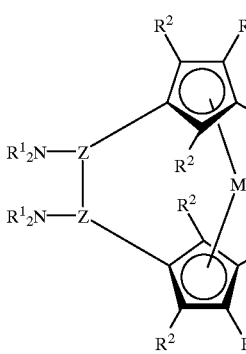

, or

Formula 9a
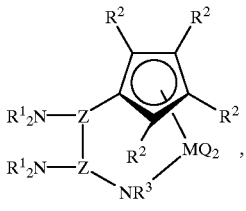

wherein Q, independently each occurrence is a halide, hydrocarbyl, hydrocarbyloxy, or dihydrocarbylamide group of up to 10 atoms not counting hydrogen, or two Q groups together form a $C_{4-20}$ diene ligand coordinated to M in a metallocyclopentene fashion. Most highly preferably Q independently each occurrence is chloride or a $C_{1-6}$ hydrocarbyl group, or two Q groups together form a 2-methyl-1,3-butadienyl or 2,3-dimethyl-1,3-butadienyl group.

Specific examples of the above metal complexes wherein M is in the +3 oxidation state are shown below in formulas 4b–9b, wherein the definitions of M, Z, $R^1$, $R^2$, and $R^3$ are as defined above:

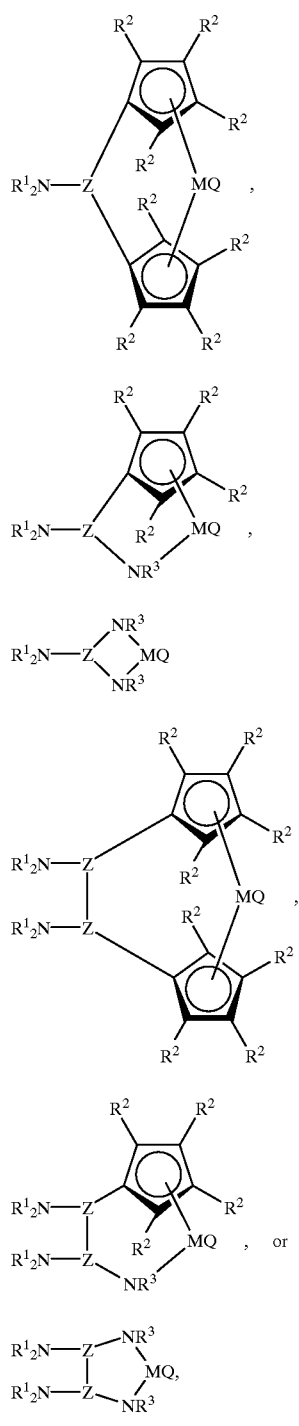

wherein Q, each occurrence is a monovalent anionic stabilizing ligand selected from the group consisting of alkyl, cycloalkyl, aryl, and silyl groups which are further substituted with one or more amine, phosphine, or ether substituents able to form a coordinate-covalent bond or chelating bond with M, said Q having up to 30 non-hydrogen atoms; or Q is a $C_{3-10}$ hydrocarbyl group comprising an ethylenic unsaturation able to form an $\eta^3$ bond with M. Most highly preferred examples of such Q ligands are 2-N,N-dimethylaminobenzyl, allyl, and 1-methyl-allyl.

Specific examples of the above metal complexes wherein M is in the +2 oxidation state are shown below in formulas 4c–9c, wherein the definitions of M, Z, $R^1$, $R^2$, and $R^3$ are as defined above:

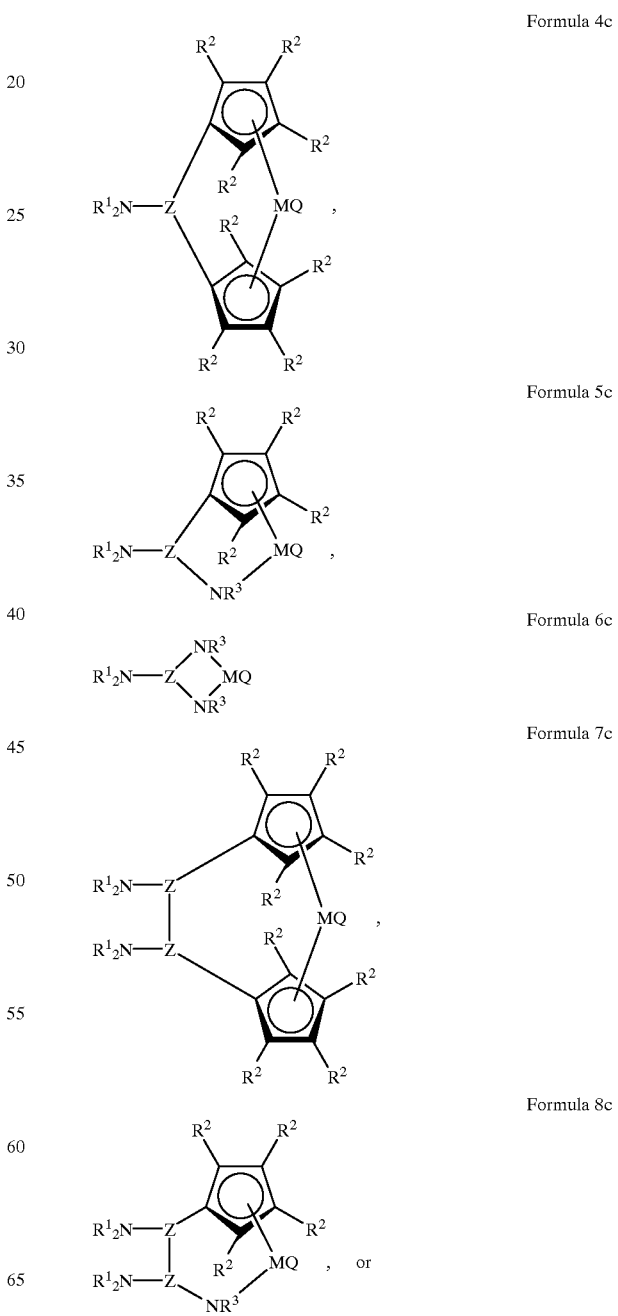

-continued

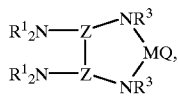

Formula 9c wherein Q, each occurrence is a neutral conjugated diene, optionally substituted with one or more tri(hydrocarbyl)silyl groups or tri(hydrocarbyl)silylhydrocarbyl groups, said Q having up to 30 atoms not counting hydrogen and forming a π-complex with M. Most highly preferred Q groups are 1,4-diphenyl-1,3-butadiene, 1,3-pentadiene, 3-methyl-1,3-pentadiene, 2,4-hexadiene, 1-phenyl-1,3-pentadiene, 1,4-dibenzyl-1,3-butadiene, 1,4-ditolyl-1,3-butadiene, 1,4-bis(trimethylsilyl)-1,3-butadiene, and 1,4-dinaphthyl-1,3-butadiene.

Preferably in the foregoing formulas, $R^1$ independently each occurrence is $C_{1-4}$ alkyl, or phenyl more preferably methyl or isopropyl, most preferably methyl, $Y^1$ and $Y^2$ are both inden-1-yl, 2-alkyl-4-arylinden-1-yl, or 3-alkylinden-1-yl, or $Y^1$ is cyclopentadienyl or alkyl-substituted cyclopentadienyl and $Y^2$ is fluorenyl; Z is boron and Q is halide, alkyl, N,N-dialkylamido, or 1,4-diphenyl-1,3-butadiene (said alkyl or aryl groups having up to 10 carbons). Even more preferably in formulas 4a–c and 7a–c, M is zirconium or hafnium and $R^1$ is methyl or isopropyl, most preferably methyl. During synthesis of these complexes, the use of methyl $R^1$ groups gives elevated, often quantitive, yields of the rac isomer.

In formulas 5a–c, 6a–c, 8a–c and 9a–c, M is even more preferably titanium, Z is boron and $R^1$ is $C_{1-4}$ alkyl or phenyl, most preferably methyl or isopropyl.

Most highly preferred metal complexes are those of formulas 4a–c and 7a–c wherein $Y^1$ and $Y^2$ are both inden-1-yl, 2-methyl-4-phenylinden-1-yl, 3-isopropylinden-1-yl, or 3-t-butylinden-1-yl groups, especially compositions comprising greater than 90 percent rac isomer.

Specific, but not limiting, metal complexes included with the invention described in the foregoing formulas are:
dimethylamidoborane-bis-$\eta^5$-cyclopentadienyl zirconium dichloride;
dimethylamidoborane-bis-$\eta^5$-cyclopentadienyl zirconium dimethyl;
dimethylamidoborane-bis-$\eta^5$-cyclopentadienyl zirconium bis-dimethylamide;
dimethylamidoborane-bis-$\eta^5$-cyclopentadienyl zirconium 2-methyl-1,3-butadiene;
dimethylamidoborane-bis-$\eta^5$-cyclopentadienyl zirconium 2,3-dimethyl-1,3-butadiene;
dimethylamidoborane-bis-$\eta^5$-cyclopentadienyl zirconium 2-N,N-dimethylaminobenzyl;
dimethylamidoborane-bis-$\eta^5$-cyclopentadienyl zirconium allyl;
dimethylamidoborane-bis-$\eta^5$-cyclopentadienyl zirconium $\eta^4$-1,4-diphenyl-1,3-butadiene;
dimethylamidoborane-bis-$\eta^5$-cyclopentadienyl zirconium $\eta^4$-2,4-hexadiene;
dimethylamidoborane-bis-$\eta^5$-cyclopentadienyl zirconium $\eta^4$-1,4-dinaphthyl-1,3-butadiene;
dimethylamidoborane-bis-$\eta^5$-cyclopentadienyl zirconium $\eta^4$-1-phenyl-1,3-pentadiene;
dimethylamidoborane-bis-$\eta^5$-cyclopentadienyl zirconium $\eta^5$-1,3-pentadiene;
dimethylamidoborane-bis-$\eta^5$-n-butylcyclopentadienyl zirconium dichloride;
dimethylamidoborane-bis-$\eta^5$-n-butylcyclopentadienyl zirconium dimethyl;
dimethylamidoborane-bis-$\eta^5$-n-butylcyclopentadienyl zirconium bis-dimethylamide;
dimethylamidoborane-bis-$\eta^5$-n-butylcyclopentadienyl zirconium 2-methyl-1,3-butadiene;
dimethylamidoborane-bis-$\eta^5$-n-butylcyclopentadienyl zirconium 2,3-dimethyl-1,3-butadiene;
dimethylamidoborane-bis-$\eta^5$-n-butylcyclopentadienyl zirconium 2-N,N-dimethylaminobenzyl;
dimethylamidoborane-bis-$\eta^5$-n-butylcyclopentadienyl zirconium allyl;
dimethylamidoborane-bis-$\eta^5$-n-butylcyclopentadienyl zirconium $\eta^4$-1,4-diphenyl-1,3-butadiene;
dimethylamidoborane-bis-$\eta^5$-n-butylcyclopentadienyl zirconium $\eta^4$-2,4-hexadiene;
dimethylamidoborane-bis-$\eta^5$-n-butylcyclopentadienyl zirconium $\eta^4$-1,4-dinaphthyl-1,3-butadiene;
dimethylamidoborane-bis-$\eta^5$-n-butylcyclopentadienyl zirconium $\eta^4$-1-phenyl-1,3-pentadiene;
dimethylamidoborane-bis-$\eta^5$-n-butylcyclopentadienyl zirconium $\eta^5$-1,3-pentadiene;
dimethylamidoborane-bis-$\eta^5$-inden-1-ylzirconium dichloride;
dimethylamidoborane-bis-$\eta^5$-inden-1-ylzirconium dimethyl;
dimethylamidoborane-bis-$\eta^5$-inden-1-ylzirconium bis-dimethylamide;
dimethylamidoborane-bis-$\eta^5$-inden-1-ylzirconium 2-methyl-1,3-butadiene;
dimethylamidoborane-bis-$\eta^5$-inden-1-ylzirconium 2,3-dimethyl-1,3-butadiene;
dimethylamidoborane-bis-$\eta^5$-inden-1-ylzirconium 2-N,N-dimethylaminobenzyl;
dimethylamidoborane-bis-$\eta^5$-inden-1-ylzirconium allyl;
dimethylamidoborane-bis-$\eta_5$-inden-1-ylzirconium $\eta^4$-1,4-diphenyl-1,3-butadiene;
dimethylamidoborane-bis-$\eta^5$-inden-1-ylzirconium $\eta^4$-2,4-hexadiene;
dimethylamidoborane-bis-$\eta^5$-inden-1-ylzirconium $\eta^4$-1,4-dinaphthyl-1,3-butadiene;
dimethylamidoborane-bis-$\eta^5$-inden-1-ylzirconium $\eta^4$-1-phenyl-1,3-pentadiene;
dimethylamidoborane-bis-$\eta^5$-inden-1-ylzirconium $\eta^4$-1,3-pentadiene;
dimethylamidoborane-bis-$\eta^5$-(2-methylinden-1-yl) zirconium dichloride;
dimethylamidoborane-bis-$\eta^5$-(2-methylinden-1-yl) zirconium dimethyl;
dimethylamidoborane-bis-$\eta^5$-(2-methylinden-1-yl) zirconium bis-dimethylamide;
dimethylamidoborane-bis-$\eta^5$-(2-methylinden-1-yl) zirconium 2-methyl-1,3-butadiene;
dimethylamidoborane-bis-$\eta^5$-(2-methylinden-1-yl) zirconium 2,3-dimethyl-1,3-butadiene;
dimethylamidoborane-bis-$\eta^5$-(2-methylinden-1-yl) zirconium 2-N,N-dimethylaminobenzyl;
dimethylamidoborane-bis-$\eta^5$-(2-methylinden-1-yl) zirconium allyl;
dimethylamidoborane-bis-$\eta^5$-(2-methylinden-1-yl) zirconium $\eta^4$-1,4-diphenyl-1,3-butadiene;
dimethylamidoborane-bis-$\eta^5$-(2-methylinden-1-yl) zirconium $\eta^4$-2,4-hexadiene;
dimethylamidoborane-bis-$\eta^5$-(2-methylinden-1-yl) zirconium $\eta^4$-1,4-dinaphthyl-1,3-butadiene;
dimethylamidoborane-bis-$\eta^5$-(2-methylinden-1-yl) zirconium $\eta^4$-1-phenyl-1,3-pentadiene;
dimethylamidoborane-bis-$\eta^5$-(2-methylinden-1-yl) zirconium $\eta^4$-1,3-pentadiene;

dimethylamidoborane-bis-$\eta^5$-(2-methyl-4-phenylinden-1-yl)zirconium dichloride;
dimethylamidoborane-bis-$\eta^5$-(2-methyl-4-phenylinden-1-yl)zirconium dimethyl;
dimethylamidoborane-bis-$\eta^5$-(2-methyl-4-phenylinden-1-yl)zirconium bis-dimethylamide;
dimethylamidoborane-bis-$\eta^5$-(2-methyl-4-phenylinden-1-yl)zirconium 2-methyl-1,3-butadiene;
dimethylamidoborane-bis-$\eta^5$-(2-methyl-4-phenylinden-1-yl)zirconium 2,3-dimethyl-1,3-butadiene;
dimethylamidoborane-bis-$\eta^5$-(2-methyl-4-phenylinden-1-yl)zirconium 2-N,N-dimethylaminobenzyl;
dimethylamidoborane-bis-$\eta^5$-(2-methyl-4-phenylinden-1-yl)zirconium allyl;
dimethylamidoborane-bis-$\eta^5$-(2-methyl-4-phenylinden-1-yl)zirconium $\eta^4$-1,4-diphenyl-1,3-butadiene;
dimethylamidoborane-bis-$\eta^5$-(2-methyl-4-phenylinden-1-yl)zirconium $\eta^4$-2,4-hexadiene;
dimethylamidoborane-bis-$\eta^5$-(2-methyl-4-phenylinden-1-yl)zirconium $\eta^4$-1,4-dinaphthyl-1,3-butadiene;
dimethylamidoborane-bis-$\eta^5$-(2-methyl-4-phenylinden-1-yl)zirconium $\eta^4$-1-phenyl-1,3-pentadiene;
dimethylamidoborane-bis-$\eta^5$-(2-methyl-4-phenylinden-1-yl)zirconium $\eta^4$-1,3-pentadiene;
dimethylamidoborane-bis-$\eta^5$-(2-ethyl-4-phenylinden-1-yl)zirconium dichloride;
dimethylamidoborane-bis-$\eta^5$-(2-ethyl-4-phenylinden-1-yl)zirconium dimethyl;
dimethylamidoborane-bis-$\eta^5$-(2-ethyl-4-phenylinden-1-yl)zirconium bis-dimethylamide;
dimethylamidoborane-bis-$\eta^5$-(2-ethyl-4-phenylinden-1-yl)zirconium 2-methyl-1,3-butadiene;
dimethylamidoborane-bis-$\eta^5$-(2-ethyl-4-phenylinden-1-yl)zirconium 2,3-dimethyl-1,3-butadiene;
dimethylamidoborane-bis-$\eta^5$-(2-ethyl-4-phenylinden-1-yl)zirconium 2-N,N-dimethylaminobenzyl;
dimethylamidoborane-bis-$\eta^5$-(2-ethyl-4-phenylinden-1-yl)zirconium allyl;
dimethylamidoborane-bis-$\eta^5$-(2-ethyl-4-phenylinden-1-yl)zirconium $\eta^4$-1,4-diphenyl-1,3-butadiene;
dimethylamidoborane-bis-$\eta^5$-(2-ethyl-4-phenylinden-1-yl)zirconium $\eta^4$-2,4-hexadiene;
dimethylamidoborane-bis-$\eta^5$-(2-ethyl-4-phenylinden-1-yl)zirconium $\eta^4$-1,4-dinaphthyl-1,3-butadiene;
dimethylamidoborane-bis-$\eta^5$-(2-ethyl-4-phenylinden-1-yl)zirconium $\eta^4$-1-phenyl-1,3-pentadiene;
dimethylamidoborane-bis-$\eta^5$-(2-ethyl-4-phenylinden-1-yl)zirconium $\eta^4$-1,3-pentadiene;
dimethylamidoborane-bis-$\eta^5$-(2-isopropyl-4-phenylinden-1-yl)zirconium dichloride;
dimethylamidoborane-bis-$\eta^5$-(2-isopropyl-4-phenylinden-1-yl)zirconium dimethyl;
dimethylamidoborane-bis-$\eta^5$-(2-isopropyl-4-phenylinden-1-yl)zirconium bis-dimethylamide;
dimethylamidoborane-bis-$\eta^5$-(2-isopropyl-4-phenylinden-1-yl)zirconium 2-methyl-1,3-butadiene;
dimethylamidoborane-bis-$\eta^5$-(2-isopropyl-4-phenylinden-1-yl)zirconium 2,3-dimethyl-1,3-butadiene;
dimethylamidoborane-bis-$\eta^5$-(2-isopropyl-4-phenylinden-1-yl)zirconium 2-N,N-dimethylaminobenzyl;
dimethylamidoborane-bis-$\eta^5$-(2-isopropyl-4-phenylinden-1-yl)zirconium allyl;
dimethylamidoborane-bis-$\eta^5$-(2-isopropyl-4-phenylinden-1-yl)zirconium $\eta^4$-1,4-diphenyl-1,3butadiene;
dimethylamidoborane-bis-$\eta^5$-(2-isopropyl-4-phenylinden-1-yl)zirconium $\eta^4$-2,4-hexadiene;
dimethylamidoborane-bis-$\eta^5$-(2-isopropyl-4-phenylinden-1-yl)zirconium $\eta^4$-1,4-dinaphthyl-1,3-butadiene;
dimethylamidoborane-bis-$\eta^5$-(2-isopropyl-4-phenylinden-1-yl)zirconium $\eta^4$-1-phenyl-1,3-pentadiene;
dimethylamidoborane-bis-$\eta^5$-(2-isopropyl-4-phenylinden-1-yl)zirconium $\eta^4$-1,3-pentadiene;
dimethylamidoborane-bis-$\eta^5$-(2-methyl-4-naphthylinden-1-yl)zirconium dichloride;
dimethylamidoborane-bis-$\eta^5$-(2-methyl-4-naphthylinden-1-yl)zirconium dimethyl;
dimethylamidoborane-bis-$\eta^5$-(2-methyl-4-naphthylinden-1-yl)zirconium bis-dimethylamide;
dimethylamidoborane-bis-$\eta^5$-(2-methyl-4-naphthylinden-1-yl)zirconium 2-methyl-1,3-butadiene;
dimethylamidoborane-bis-$\eta^5$-(2-methyl-4-naphthylinden-1-yl)zirconium 2,3-dimethyl-1,3-butadiene;
dimethylamidoborane-bis-$\eta^5$-(2-methyl-4-naphthylinden-1-yl)zirconium 2-N,N-dimethylaminobenzyl;
dimethylamidoborane-bis-$\eta^5$-(2-methyl-4-naphthylinden-1-yl)zirconium allyl;
dimethylamidoborane-bis-$\eta^5$-(2-methyl-4-naphthylinden-1-yl)zirconium $\eta^4$-1,4-diphenyl-1,3-butadiene;
dimethylamidoborane-bis-$\eta^5$-(2-methyl-4-naphthylinden-1-yl)zirconium $\eta^4$-2,4-hexadiene;
dimethylamidoborane-bis-$\eta^5$-(2-methyl-4-naphthylinden-1-yl)zirconium $\eta^4$-1,4-dinaphthyl-1,3-butadiene;
dimethylamidoborane-bis-$\eta^5$-(2-methyl-4-naphthylinden-1-yl)zirconium $\eta^4$-1-phenyl-1,3-pentadiene;
dimethylamidoborane-bis-$\eta^5$-(2-methyl-4-naphthylinden-1-yl)zirconium $\eta$4-1,3-pentadiene;
dimethylamidoborane-bis-$\eta^5$-(2-methyl-4-bis(3,5-trifluoromethyl)phenylinden-1-yl)zirconium dichloride;
dimethylamidoborane-bis-$\eta^5$-(2-methyl-4-bis(3,5-trifluoromethyl)phenylinden-1-yl)zirconium dimethyl;
dimethylamidoborane-bis-$\eta^5$-(2-methyl-4-bis(3,5-trifluoromethyl)phenylinden-1-yl)zirconium bis-dimethylamide;
dimethylamidoborane-bis-$\eta^5$-(2-methyl-4-bis(3,5-trifluoromethyl)phenylinden-1-yl)zirconium 2-methyl-1,3-butadiene;
dimethylamidoborane-bis-$\eta^5$-(2-methyl-4-bis(3,5-trifluoromethyl)phenylinden-1-yl)zirconium 2,3-dimethyl-1,3-butadiene;
dimethylamidoborane-bis-$\eta^5$-(2-methyl-4-bis(3,5-trifluoromethyl)phenylinden-1-yl)zirconium 2-N,N-dimethylaminobenzyl;
dimethylamidoborane-bis-$\eta^5$-(2-methyl-4-bis(3,5-trifluoromethyl)phenylinden-1-yl)zirconium allyl;
dimethylamidoborane-bis-$\eta^5$-(2-methyl-4-bis(3,5-trifluoromethyl)phenylinden-1-yl)zirconium $\eta^4$-1,4-diphenyl-1,3-butadiene;
dimethylamidoborane-bis-$\eta^5$-(2-methyl-4-bis(3,5-trifluoromethyl)phenylinden-1-yl)zirconium $\eta^4$-2,4-hexadiene;
dimethylamidoborane-bis-$\eta^5$-(2-methyl-4-bis(3,5-trifluoromethyl)phenylinden-1-yl)zirconium $\eta^4$-1,4-dinaphthyl-1,3-butadiene;
dimethylamidoborane-bis-$\eta^5$-(2-methyl-4-bis(3,5-trifluoromethyl)phenylinden-1-yl)zirconium $\eta^4$-1-phenyl-1,3-pentadiene;
dimethylamidoborane-bis-$\eta^5$-(2-methyl-4-bis(3,5-trifluoromethyl)phenylinden-1-yl)zirconium $\eta^4$-1,3-pentadiene;
dimethylamidoborane-bis-$\eta^5$-(2-ethyl-4-bis(3,5-trifluoromethyl)phenylinden-1-yl)zirconium dichloride;
dimethylamidoborane-bis-$\eta^5$-(2-ethyl-4-bis(3,5-trifluoromethyl)phenylinden-1-yl)zirconium dimethyl;
dimethylamidoborane-bis-$\eta^5$-(2-ethyl-4-bis(3,5-trifluoromethyl)phenylinden-1-yl)zirconium bis-dimethylamide;

dimethylamidoborane-bis-$\eta^5$-(2-ethyl-4-bis(3,5-trifluoromethyl)phenylinden-1-yl)zirconium 2-methyl-1,3-butadiene;
dimethylamidoborane-bis-$\eta^5$-(2-ethyl-4-bis(3,5-trifluoromethyl)phenylinden-1-yl)zirconium 2,3-dimethyl-1,3-butadiene;
dimethylamidoborane-bis-$\eta^5$-(2-ethyl-4-bis(3,5-trifluoromethyl)phenylinden-1-yl)zirconium 2-N,N-dimethylaminobenzyl;
dimethylamidoborane-bis-$\eta^5$-(2-ethyl-4-bis(3,5-trifluoromethyl)phenylinden-1-yl)zirconium allyl;
dimethylamidoborane-bis-$\eta^5$-(2-ethyl-4-bis(3,5-trifluoromethyl)phenylinden-1-yl)zirconium $\eta^4$-4-diphenyl-1,3-butadiene;
dimethylamidoborane-bis-$\eta^5$-(2-ethyl-4-bis(3,5-trifluoromethyl)phenylinden-1-yl)zirconium $\eta^4$-2,4-hexadiene;
dimethylamidoborane-bis-$\eta^5$-(2-ethyl-4-bis(3,5-trifluoromethyl)phenylinden-1-yl)zirconium $\eta^4$-1,4-dinaphthyl-1,3-butadiene;
dimethylamidoborane-bis-$\eta^5$-(2-ethyl-4-bis(3,5-trifluoromethyl)phenylinden-1-yl)zirconium $\eta^4$-1-phenyl-1,3-pentadiene;
dimethylamidoborane-bis-$\eta^5$-(2-ethyl-4-bis(3,5-trifluoromethyl)phenylinden-1-yl)zirconium $\eta^4$-1,3-pentadiene;
dimethylamidoborane-bis-$\eta^5$-(2-isopropyl-4-bis(3,5-trifluoromethyl)phenylinden-1-yl)zirconium dichloride;
dimethylamidoborane-bis-$\eta^5$-(2-isopropyl-4-bis(3,5-trifluoromethyl)phenylinden-1-yl)zirconium dimethyl;
dimethylamidoborane-bis-$\eta^5$-(2-isopropyl-4-bis(3,5-trifluoromethyl)phenylinden-1-yl)zirconium bis-dimethylamide;
dimethylamidoborane-bis-$\eta^5$-(2-isopropyl-4-bis(3,5-trifluoromethyl)phenylinden-1-yl)zirconium 2-methyl-1,3-butadiene;
dimethylamidoborane-bis-$\eta^5$-(2-isopropyl-4-bis(3,5-trifluoromethyl)phenylinden-1-yl)zirconium 2,3-dimethyl-1,3-butadiene;
dimethylamidoborane-bis-$\eta^5$-(2-isopropyl-4-bis(3,5-trifluoromethyl)phenylinden-1-yl)zirconium 2-N,N-dimethylaminobenzyl;
dimethylamidoborane-bis-$\eta^5$-(2-isopropyl-4-bis(3,5-trifluoromethyl)phenylinden-1-yl)zirconium allyl;
dimethylamidoborane-bis-$\eta^5$-(2-isopropyl-4-bis(3,5-trifluoromethyl)phenylinden-1-yl)zirconium $\eta^4$-1,4-diphenyl-1,3-butadiene;
dimethylamidoborane-bis-$\eta^5$-(2-isopropyl-4-bis(3,5-trifluoromethyl)phenylinden-1-yl)zirconium $\eta^4$-2,4-hexadiene;
dimethylamidoborane-bis-$\eta^5$-(2-isopropyl-4-bis(3,5-trifluoromethyl)phenylinden-1-yl)zirconium $\eta^4$-1,4-dinaphthyl-1,3-butadiene;
dimethylamidoborane-bis-$\eta^5$-(2-isopropyl-4-bis(3,5-trifluoromethyl)phenylinden-1-yl)zirconium $\eta^4$-1-phenyl-1,3-pentadiene;
dimethylamidoborane-bis-$\eta^5$-(2-isopropyl-4-bis(3,5-trifluoromethyl)phenylinden-1-yl)zirconium $\eta^4$-1,3-pentadiene;
dimethylamidoborane-bis-$\eta^5$-(3-isopropylinden-1-yl)zirconium dichloride;
dimethylamidoborane-bis-$\eta^5$-(3-isopropylinden-1-yl)zirconium dimethyl;
dimethylamidoborane-bis-$\eta^5$-(3-isopropylinden-1-yl)zirconium bis-dimethylamide;
dimethylamidoborane-bis-$\eta^5$-(3-isopropylinden-1-yl)zirconium 2-methyl-1,3-butadiene;
dimethylamidoborane-bis-$\eta^5$-(3-isopropylinden-1-yl)zirconium 2,3-dimethyl-1,3-butadiene;
dimethylamidoborane-bis-$\eta^5$-(3-isopropylinden-1-yl)zirconium 2-N,N-dimethylaminobenzyl;
dimethylamidoborane-bis-$\eta^5$-(3-isopropylinden-1-yl)zirconium allyl;
dimethylamidoborane-bis-$\eta^5$-(3-isopropylinden-1-yl)zirconium $\eta^4$-1,4-diphenyl-1,3-butadiene;
dimethylamidoborane-bis-$\eta^5$-(3-isopropylinden-1-yl)zirconium $\eta^4$-2,4-hexadiene;
dimethylamidoborane-bis-$\eta^5$-(3-isopropylinden-1-yl)zirconium $\eta^4$-1,4-dinaphthyl-1,3-butadiene;
dimethylamidoborane-bis-$\eta^5$-(3-isopropylinden-1-yl)zirconium $\eta^4$-1-phenyl-1,3-pentadiene;
dimethylamidoborane-bis-$\eta^5$-(3-isopropylinden-1-yl)zirconium $\eta^4$-1,3-pentadiene;
dimethylamidoborane-bis-$\eta^5$-(3-t-butylinden-1-yl)zirconium dichloride;
dimethylamidoborane-bis-$\eta^5$-(3-t-butylinden-1-yl)zirconium dimethyl;
dimethylamidoborane-bis-$\eta^5$-(3-t-butylinden-1-yl)zirconium bis-dimethylamide;
dimethylamidoborane-bis-$\eta^5$-(3-t-butylinden-1-yl)zirconium 2-methyl-1,3-butadiene;
dimethylamidoborane-bis-$\eta^5$-(3-t-butylinden-1-yl)zirconium 2,3-dimethyl-1,3-butadiene;
dimethylamidoborane-bis-$\eta^5$-(3-t-butylinden-1-yl)zirconium 2-N,N-dimethylaminobenzyl;
dimethylamidoborane-bis-$\eta^5$-(3-t-butylinden-1-yl)zirconium allyl;
dimethylamidoborane-bis-$\eta^5$-(3-t-butylinden-1-yl)zirconium $\eta^4$-1,4-diphenyl-1,3-butadiene;
dimethylamidoborane-bis-$\eta^5$-(3-t-butylinden-1-yl)zirconium $\eta^4$-2,4-hexadiene;
dimethylamidoborane-bis-$\eta^5$-(3-t-butylinden-1-yl)zirconium $\eta^4$-1,4-dinaphthyl-1,3-butadiene;
dimethylamidoborane-bis-$\eta^5$-(3-t-butylinden-1-yl)zirconium $\eta^4$-1-phenyl-1,3-pentadiene;
dimethylamidoborane-bis-$\eta^5$-(3-t-butylinden-1-yl)zirconium $\eta^4$-1,3-pentadiene;
diisopropylamidoborane-bis-$\eta^5$-cyclopentadienylzirconium dichloride;
diisopropylamidoborane-bis-$\eta^5$-cyclopentadienylzirconium dimethyl;
diisopropylamidoborane-bis-$\eta^5$-cyclopentadienylzirconium bis-dimethylamide;
diisopropylamidoborane-bis-$\eta^5$-cyclopentadienylzirconium 2-methyl-1,3-butadiene;
diisopropylamidoborane-bis-$\eta^5$-cyclopentadienylzirconium 2,3-dimethyl-1,3-butadiene;
diisopropylamidoborane-bis-$\eta^5$-cyclopentadienylzirconium 2-N,N-dimethylaminobenzyl;
diisopropylamidoborane-bis-$\eta^5$-cyclopentadienylzirconium allyl;
diisopropylamidoborane-bis-$\eta^5$-cyclopentadienylzirconium $\eta^4$-1,4-diphenyl-1,3-butadiene;
diisopropylamidoborane-bis-$\eta^5$-cyclopentadienylzirconium $\eta^4$-2,4-hexadiene;
diisopropylamidoborane-bis-$\eta^5$-cyclopentadienylzirconium $\eta^4$-1,4-dinaphthyl-1,3-butadiene;
diisopropylamidoborane-bis-$\eta^5$-cyclopentadienylzirconium $\eta^4$-1-phenyl-1,3-pentadiene;
diisopropylamidoborane-bis-$\eta^5$-cyclopentadienylzirconium $\eta^5$-1,3-pentadiene;
diisopropylamidoborane-bis-$\eta^5$-inden-1-ylzirconium dichloride;
diisopropylamidoborane-bis-$\eta^5$-inden-1-ylzirconium dimethyl;

diisopropylamidoborane-bis-$\eta^5$-inden-1-ylzirconium bis-dimethylamide;
diisopropylamidoborane-bis-$\eta^5$-inden-1-ylzirconium 2-methyl-1,3-butadiene;
diisopropylamidoborane-bis-$\eta^5$-inden-1-ylzirconium 2,3-dimethyl-1,3-butadiene;
diisopropylamidoborane-bis-$\eta^5$-inden-1-ylzirconium 2-N,N-dimethylaminobenzyl;
diisopropylamidoborane-bis-$\eta^5$-inden-1-ylzirconium allyl;
diisopropylamidoborane-bis-$\eta^5$-inden-1-ylzirconium 1,4-diphenyl-1,3-butadiene;
diisopropylamidoborane-bis-$\eta^5$-inden-1-ylzirconium $\eta^4$-2,4-hexadiene;
diisopropylamidoborane-bis-$\eta^5$-inden-1-ylzirconium $\eta^4$-1,4-dinaphthyl-1,3-butadiene;
diisopropylamidoborane-bis-$\eta^5$-inden-1-ylzirconium $\eta^4$-1-phenyl-1,3-pentadiene;
diisopropylamidoborane-bis-$\eta^5$-inden-1-ylzirconium $\eta^4$-1,3-pentadiene;
diisopropylamidoborane-bis-$\eta^5$-(2-methylinden-1-yl)zirconium dichloride;
diisopropylamidoborane-bis-$\eta^5$-(2-methylinden-1-yl)zirconium dimethyl;
diisopropylamidoborane-bis-$\eta^5$-(2-methylinden-1-yl)zirconium bis-dimethylamide;
diisopropylamidoborane-bis-$\eta^5$-(2-methylinden-1-yl)zirconium 2-methyl-1,3-butadiene;
diisopropylamidoborane-bis-$\eta^5$-(2-methylinden-1-yl)zirconium 2,3-dimethyl-1,3-butadiene;
diisopropylamidoborane-bis-$\eta^5$-(2-methylinden-1-yl)zirconium 2-N,N-dimethylaminobenzyl;
diisopropylamidoborane-bis-$\eta^5$-(2-methylinden-1-yl)zirconium allyl;
diisopropylamidoborane-bis-$\eta^5$-(2-methylinden-1-yl)zirconium $\eta^4$-1,4-diphenyl-1,3-butadiene;
diisopropylamidoborane-bis-$\eta^5$-(2-methylinden-1-yl)zirconium $\eta^4$-2,4-hexadiene;
diisopropylamidoborane-bis-$\eta^5$-(2-methylinden-1-yl)zirconium $\eta^4$-1,4-dinaphthyl-1,3-butadiene;
diisopropylamidoborane-bis-$\eta^5$-(2-methylinden-1-yl)zirconium $\eta^4$-1-phenyl-1,3-pentadiene;
diisopropylamidoborane-bis-$\eta^5$-(2-methylinden-1-yl)zirconium $\eta^4$-1,3-pentadiene;
diisopropylamidoborane-bis-$\eta^5$-(2-methyl-4-phenylinden-1-yl)zirconium dichloride;
diisopropylamidoborane-bis-$\eta^5$-(2-methyl-4-phenylinden-1-yl)zirconium dimethyl;
diisopropylamidoborane-bis-$\eta^5$-(2-methyl-4-phenylinden-1-yl)zirconium bis-dimethylamide;
diisopropylamidoborane-bis-$\eta^5$-(2-methyl-4-phenylinden-1-yl)zirconium 2-methyl-1,3-butadiene;
diisopropylamidoborane-bis-$\eta^5$-(2-methyl-4-phenylinden-1-yl)zirconium 2,3-dimethyl-1,3-butadiene;
diisopropylamidoborane-bis-$\eta^5$-(2-methyl-4-phenylinden-1-yl)zirconium 2-N,N-dimethylaminobenzyl;
diisopropylamidoborane-bis-$\eta^5$-(2-methyl-4-phenylinden-1-yl)zirconium allyl;
diisopropylamidoborane-bis-$\eta^5$-(2-methyl-4-phenylinden-1-yl)zirconium $\eta^4$-1,4-diphenyl-1,3-butadiene;
diisopropylamidoborane-bis-$\eta^5$-(2-methyl-4-phenylinden-1-yl)zirconium $\eta^4$-2,4-hexadiene;
diisopropylamidoborane-bis-$\eta^5$-(2-methyl-4-phenylinden-1-yl)zirconium $\eta^4$-1,4-dinaphthyl-1,3-butadiene;
diisopropylamidoborane-bis-$\eta^5$-(2-methyl-4-phenylinden-1-yl)zirconium $\eta^4$-1-phenyl-1,3-pentadiene;
diisopropylamidoborane-bis-$\eta^5$-(2-methyl-4-phenylinden-1-yl)zirconium $\eta^4$-1,3-pentadiene;
diisopropylamidoborane-bis-$\eta^5$-(2-methyl-4-naphthylinden-1-yl)zirconium dichloride;
diisopropylamidoborane-bis-$\eta^5$-(2-methyl-4-naphthylinden-1-yl)zirconium dimethyl;
diisopropylamidoborane-bis-$\eta^5$-(2-methyl-4-naphthylinden-1-yl)zirconium bis-dimethylamide;
diisopropylamidoborane-bis-$\eta^5$-(2-methyl-4-naphthylinden-1-yl)zirconium 2-methyl-1,3-butadiene;
diisopropylamidoborane-bis-$\eta^5$-(2-methyl-4-naphthylinden-1-yl)zirconium 2,3-dimethyl-1,3-butadiene;
diisopropylamidoborane-bis-$\eta^5$-(2-methyl-4-naphthylinden-1-yl)zirconium 2-N,N-dimethylaminobenzyl;
diisopropylamidoborane-bis-$\eta^5$-(2-methyl-4-naphthylinden-1-yl)zirconium allyl;
diisopropylamidoborane-bis-$\eta^5$-(2-methyl-4-naphthylinden-1-yl)zirconium $\eta^4$-1,4-diphenyl-1,3-butadiene;
diisopropylamidoborane-bis-$\eta^5$-(2-methyl-4-naphthylinden-1-yl)zirconium $\eta^4$-2,4-hexadiene;
diisopropylamidoborane-bis-$\eta^5$-(2-methyl-4-naphthylinden-1-yl)zirconium $\eta^4$-1,4-dinaphthyl-1,3-butadiene;
diisopropylamidoborane-bis-$\eta^5$-(2-methyl-4-naphthylinden-1-yl)zirconium $\eta^4$-1-phenyl-1,3-pentadiene;
diisopropylamidoborane-bis-$\eta^5$-(2-methyl-4-naphthylinden-1-yl)zirconium $\eta^4$-1,3-pentadiene;
diisopropylamidoborane-bis-$\eta^5$-(2-methyl-4-(3,5-dimethylphenyl)inden-1-yl)zirconium dichloride;
diisopropylamidoborane-bis-$\eta^5$-(2-methyl-4-(3,5-dimethylphenyl)inden-1-yl)zirconium dimethyl;
diisopropylamidoborane-bis-$\eta^5$-(2-methyl-4-(3,5-dimethylphenyl)inden-1-yl)zirconium bis-dimethylamide;
diisopropylamidoborane-bis-$\eta^5$-(2-methyl-4-(3,5-dimethylphenyl)inden-1-yl)zirconium 2-methyl-1,3-butadiene;
diisopropylamidoborane-bis-$\eta^5$-(2-methyl-4-(3,5-dimethylphenyl)inden-1-yl)zirconium 2,3-dimethyl-1,3-butadiene;
diisopropylamidoborane-bis-$\eta^5$-(2-methyl-4-(3,5-dimethylphenyl)inden-1-yl)zirconium 2-N,N-dimethylaminobenzyl;
diisopropylamidoborane-bis-$\eta^5$-(2-methyl-4-(3,5-dimethylphenyl)inden-1-yl)zirconium allyl;
diisopropylamidoborane-bis-$\eta^5$-(2-methyl-4-(3,5-dimethylphenyl)inden-1-yl)zirconium $\eta^4$-1,4-diphenyl-1,3-butadiene;
diisopropylamidoborane-bis-$\eta^5$-(2-methyl-4-(3,5-dimethylphenyl)inden-1-yl)zirconium $\eta^4$-2,4-hexadiene;
diisopropylamidoborane-bis-$\eta^5$-(2-methyl-4-(3,5-dimethylphenyl)inden-1-yl)zirconium $\eta^4$-1,4-dinaphthyl-1,3-butadiene;
diisopropylamidoborane-bis-$\eta^5$-(2-methyl-4-(3,5-dimethylphenyl)inden-1-yl)zirconium $\eta^4$-1-phenyl-1,3-pentadiene;
diisopropylamidoborane-bis-$\eta^5$-(2-methyl-4-(3,5-dimethylphenyl)inden-1-yl)zirconium $\eta^4$-1,3-pentadiene;
diisopropylamidoborane-bis-$\eta^5$-(2-methyl-4-(3,5-difluoromethylphenyl)inden-1-yl)zirconium dichloride;
diisopropylamidoborane-bis-$\eta^5$-(2-methyl-4-(3,5-difluoromethylphenyl)inden-1-yl)zirconium dimethyl;
diisopropylamidoborane-bis-$\eta^5$-(2-methyl-4-(3,5-difluoromethylphenyl)inden-1-yl)zirconium bis-dimethylamide;

diisopropylamidoborane-bis-$\eta^5$-(2-methyl-4-(3,5-difluoromethylphenyl)inden-1-yl)zirconium 2-methyl-1,3-butadiene;
diisopropylamidoborane-bis-$\eta^5$-(2-methyl-4-(3,5-difluoromethylphenyl)inden-1-yl)zirconium 2,3-dimethyl-1,3-butadiene;
diisopropylamidoborane-bis-$\eta^5$-(2-methyl-4-(3,5-difluoromethylphenyl)inden-1-yl)zirconium 2-N,N-dimethylaminobenzyl;
diisopropylamidoborane-bis-$\eta^5$-(2-methyl-4-(3,5-difluoromethylphenyl)inden-1-yl)zirconium allyl;
diisopropylamidoborane-bis-$\eta^5$-(2-methyl-4-(3,5-difluoromethylphenyl)inden-1-yl)zirconium $\eta^4$-1,4-diphenyl-1,3-butadiene;
diisopropylamidoborane-bis-$\eta^5$-(2-methyl-4-(3,5-difluoromethylphenyl)inden-1-yl)zirconium $\eta^4$-2,4-hexadiene;
diisopropylamidoborane-bis-$\eta^5$-(2-methyl-4-(3,5-difluoromethylphenyl)inden-1-yl)zirconium $\eta^4$-1,4-dinaphthyl-1,3-butadiene;
diisopropylamidoborane-bis-$\eta^5$-(2-methyl-4-(3,5-difluoromethylphenyl)inden-1-yl)zirconium $\eta^4$-1-phenyl-1,3-pentadiene;
diisopropylamidoborane-bis-$\eta^5$-(2-methyl-4-(3,5-difluoromethylphenyl)inden-1-1-yl)zirconium $\eta^4$-1,3-pentadiene;
diisopropylamidoborane-bis-$\eta^5$-(2-ethyl-4-phenylinden-1-yl)zirconium dichloride;
diisopropylamidoborane-bis-$\eta^5$-(2-ethyl-4-phenylinden-1-yl)zirconium dimethyl;
diisopropylamidoborane-bis-$\eta^5$-(2-ethyl-4-phenylinden-1-yl)zirconium bis-dimethylamide;
diisopropylamidoborane-bis-$\eta^5$-(2-ethyl-4-phenylinden-1-yl)zirconium 2-methyl-1,3-butadiene;
diisopropylamidoborane-bis-$\eta^5$-(2-ethyl-4-phenylinden-1-yl)zirconium 2,3-dimethyl-1,3-butadiene;
diisopropylamidoborane-bis-$\eta^5$-(2-ethyl-4-phenylinden-1-yl)zirconium 2-N,N-dimethylaminobenzyl;
diisopropylamidoborane-bis-$\eta^5$-(2-ethyl-4-phenylinden-1-yl)zirconium allyl;
diisopropylamidoborane-bis-$\eta^5$-(2-ethyl-4-phenylinden-1-yl)zirconium $\eta^4$-1,4-diphenyl-1,3-butadiene;
diisopropylamidoborane-bis-$\eta^5$-(2-ethyl-4-phenylinden-1-yl)zirconium $\eta^4$-2,4-hexadiene;
diisopropylamidoborane-bis-$\eta^5$-(2-ethyl-4-phenylinden-1-yl)zirconium $\eta^4$-1,4-dinaphthyl-1,3-butadiene;
diisopropylamidoborane-bis-$\eta^5$-(2-ethyl-4-phenylinden-1-yl)zirconium $\eta^4$-1-phenyl-1,3-pentadiene;
diisopropylamidoborane-bis-$\eta^5$-(2-ethyl-4-phenylinden-1-yl)zirconium $\eta^4$-1,3-pentadiene;
diisopropylamidoborane-bis-$\eta^5$-(2-isopropyl-4-phenylinden-1-yl)zirconium dichloride;
diisopropylamidoborane-bis-$\eta^5$-(2-isopropyl-4-phenylinden-1-yl)zirconium dimethyl;
diisopropylamidoborane-bis-$\eta^5$-(2-isopropyl-4-phenylinden-1-yl)zirconium bis-dimethylamide;
diisopropylamidoborane-bis-$\eta^5$-(2-isopropyl-4-phenylinden-1-yl)zirconium 2-methyl-1,3-butadiene;
diisopropylamidoborane-bis-$\eta^5$-(2-isopropyl-4-phenylinden-1-yl)zirconium 2,3-dimethyl-1,3-butadiene;
diisopropylamidoborane-bis-$\eta^5$-(2-isopropyl-4-phenylinden-1-yl)zirconium 2-N,N-dimethylaminobenzyl;
diisopropylamidoborane-bis-$\eta^5$-(2-isopropyl-4-phenylinden-1-yl)zirconium allyl;
diisopropylamidoborane-bis-$\eta^5$-(2-isopropyl-4-phenylinden-1-yl)zirconium $\eta^4$-1,4-diphenyl-1,3-butadiene;
diisopropylamidoborane-bis-$\eta^5$-(2-isopropyl-4-phenylinden-1-yl)zirconium $\eta^4$-2,4-hexadiene;
diisopropylamidoborane-bis-$\eta^5$-(2-isopropyl-4-phenylinden-1-yl)zirconium $\eta^4$-1,4-dinaphthyl-1,3-butadiene;
diisopropylamidoborane-bis-$\eta^5$-(2-isopropyl-4-phenylinden-1-yl)zirconium $\eta^4$-1-phenyl-1,3-pentadiene;
diisopropylamidoborane-bis-$\eta^5$-(2-isopropyl-4-phenylinden-1-yl)zirconium $\eta^4$-1,3-pentadiene;
diisopropylamidoborane-bis-$\eta^5$-(3-isopropylinden-1-yl)zirconium dichloride;
diisopropylamidoborane-bis-$\eta^5$-(3-isopropylinden-1-yl)zirconium dimethyl;
diisopropylamidoborane-bis-$\eta^5$-(3-isopropylinden-1-yl)zirconium bis-dimethylamide;
diisopropylamidoborane-bis-$\eta^5$-(3-isopropylinden-1-yl)zirconium 2-methyl-1,3-butadiene;
diisopropylamidoborane-bis-$\eta^5$-(3-isopropylinden-1-yl)zirconium 2,3-dimethyl-1,3-butadiene;
diisopropylamidoborane-bis-$\eta^5$-(3-isopropylinden-1-yl)zirconium 2-N,N-dimethylaminobenzyl;
diisopropylamidoborane-bis-$\eta^5$-(3-isopropylinden-1-yl)zirconium allyl;
diisopropylamidoborane-bis-$\eta^5$-(3-isopropylinden-1-yl)zirconium $\eta^4$-1,4-diphenyl-1,3-butadiene;
diisopropylamidoborane-bis-$\eta^5$-(3-isopropylinden-1-yl)zirconium $\eta^4$-2,4-hexadiene;
diisopropylamidoborane-bis-$\eta^5$-(3-isopropylinden-1-yl)zirconium $\eta^4$-1,4-dinaphthyl-1,3-butadiene;
diisopropylamidoborane-bis-$\eta^5$-(3-isopropylinden-1-yl)zirconium $\eta^4$-1-phenyl-1,3-pentadiene;
diisopropylamidoborane-bis-$\eta^5$-(3-isopropylinden-1-yl)zirconium $\eta^4$-1,3-pentadiene;
diisopropylamidoborane-bis-$\eta^5$-(3-t-butylinden-1-yl)zirconium dichloride;
diisopropylamidoborane-bis-$\eta^5$-(3-t-butylinden-1-yl)zirconium dimethyl;
diisopropylamidoborane-bis-$\eta^5$-(3-t-butylinden-1-yl)zirconium bis-dimethylamide;
diisopropylamidoborane-bis-$\eta^5$-(3-t-butylinden-1-yl)zirconium 2-methyl-1,3-butadiene;
diisopropylamidoborane-bis-$\eta^5$-(3-t-butylinden-1-yl)zirconium 2,3-dimethyl-1,3-butadiene;
diisopropylamidoborane-bis-$\eta^5$-(3-t-butylinden-1-yl)zirconium 2-N,N-dimethylaminobenzyl;
diisopropylamidoborane-bis-$\eta^5$-(3-t-butylinden-1-yl)zirconium allyl;
diisopropylamidoborane-bis-$\eta^5$-(3-t-butylinden-1-yl)zirconium $\eta^4$-1,4-diphenyl-1,3-butadiene;
diisopropylamidoborane-bis-$\eta^5$-(3-t-butylinden-1-yl)zirconium $\eta^4$-2,4-hexadiene;
diisopropylamidoborane-bis-$\eta^5$-(3-t-butylinden-1-yl)zirconium $\eta^4$-1,4-dinaphthyl-1,3-butadiene;
diisopropylamidoborane-bis-$\eta^5$-(3-t-butylinden-1-yl)zirconium $\eta^4$-1-phenyl-1,3-pentadiene;
diisopropylamidoborane-bis-$\eta^5$-(3-t-butylinden-1-yl)zirconium $\eta^4$-1,3-pentadiene;
diphenylamidoborane-bis-$\eta^5$-cyclopentadienyl zirconium dichloride;
diphenylamidoborane-bis-$\eta^5$-cyclopentadienyl zirconium dimethyl;
diphenylamidoborane-bis-$\eta^5$-cyclopentadienyl zirconium bis-dimethylamide;
diphenylamidoborane-bis-$\eta^5$-cyclopentadienyl zirconium 2-methyl-1,3-butadiene;
diphenylamidoborane-bis-$\eta^5$-cyclopentadienyl zirconium 2,3-dimethyl-1,3-butadiene;

diphenylamidoborane-bis-η⁵-cyclopentadienyl zirconium 2-N,N-dimethylaminobenzyl;
diphenylamidoborane-bis-η⁵-cyclopentadienyl zirconium allyl;
diphenylamidoborane-bis-η⁵-cyclopentadienyl zirconium η⁴-1,4-diphenyl-1,3-butadiene;
diphenylamidoborane-bis-η⁵-cyclopentadienyl zirconium η⁴-2,4-hexadiene;
diphenylamidoborane-bis-η⁵-cyclopentadienyl zirconium η⁴-1,4-dinaphthyl-1,3-butadiene;
diphenylamidoborane-bis-η⁵-cyclopentadienyl zirconium η⁴-1-phenyl-1,3-pentadiene;
diphenylamidoborane-bis-η⁵-cyclopentadienyl zirconium η⁵-1,3-pentadiene;
diphenylamidoborane-bis-η⁵-n-butylcyclopentadienyl zirconium dichloride;
diphenylamidoborane-bis-η⁵-n-butylcyclopentadienyl zirconium dimethyl;
diphenylamidoborane-bis-η⁵-n-butylcyclopentadienyl zirconium bis-dimethylamide;
diphenylamidoborane-bis-η⁵-n-butylcyclopentadienyl zirconium 2-methyl-1,3-butadiene;
diphenylamidoborane-bis-η⁵-n-butylcyclopentadienyl zirconium 2,3-dimethyl-1,3-butadiene;
diphenylamidoborane-bis-η⁵-n-butylcyclopentadienyl zirconium 2-N,N-dimethylaminobenzyl;
diphenylamidoborane-bis-η⁵-n-butylcyclopentadienyl zirconium allyl;
diphenylamidoborane-bis-η⁵-n-butylcyclopentadienyl zirconium η⁴-diphenyl-1,3-butadiene;
diphenylamidoborane-bis-η⁵-n-butylcyclopentadienyl zirconium η⁴-2,4-hexadiene;
diphenylamidoborane-bis-η⁵-n-butylcyclopentadienyl zirconium η⁴-1,4-dinaphthyl-1,3-butadiene;
diphenylamidoborane-bis-η⁵-n-butylcyclopentadienyl zirconium η⁴-1-phenyl-1,3-pentadiene;
diphenylamidoborane-bis-η⁵-n-butylcyclopentadienyl zirconium η⁵-1,3-pentadiene;
diphenylamidoborane-bis-η⁵-inden-1-ylzirconium dichloride;
diphenylamidoborane-bis-η⁵-inden-1-ylzirconium dimethyl;
diphenylamidoborane-bis-η⁵-inden-1-ylzirconium bis-dimethylamide;
diphenylamidoborane-bis-η⁵-inden-1-ylzirconium 2-methyl-1,3-butadiene;
diphenylamidoborane-bis-η⁵-inden-1-ylzirconium 2,3-dimethyl-1,3-butadiene;
diphenylamidoborane-bis-η⁵-inden-1-ylzirconium 2-N,N-dimethylaminobenzyl;
diphenylamidoborane-bis-η⁵-inden-1-ylzirconium allyl;
diphenylamidoborane-bis-η⁵-inden-1-ylzirconium η⁴-1,4-diphenyl-1,3-butadiene;
diphenylamidoborane-bis-η⁵-inden-1-ylzirconium η⁴-2,4-hexadiene;
diphenylamidoborane-bis-η⁵-inden-1-ylzirconium η⁴-1,4-dinaphthyl-1,3-butadiene;
diphenylamidoborane-bis-η⁵-inden-1-ylzirconium η⁴-1-phenyl-1,3-pentadiene;
diphenylamidoborane-bis-η⁵-inden-1-ylzirconium η⁴-1,3-pentadiene;
diphenylamidoborane-bis-η⁵-(2-methylinden-1-yl)zirconium dichloride;
diphenylamidoborane-bis-η⁵-(2-methylinden-1-yl)zirconium dimethyl;
diphenylamidoborane-bis-η⁵-(2-methylinden-1-yl)zirconium bis-dimethylamide;
diphenylamidoborane-bis-η⁵-(2-methylinden-1-yl)zirconium 2-methyl-1,3-butadiene;
diphenylamidoborane-bis-η⁵-(2-methylinden-1-yl)zirconium 2,3-dimethyl-1,3-butadiene;
diphenylamidoborane-bis-η⁵-(2-methylinden-1-yl)zirconium 2-N,N-dimethylaminobenzyl;
diphenylamidoborane-bis-η⁵-(2-methylinden-1-yl)zirconium allyl;
diphenylamidoborane-bis-η⁵-(2-methylinden-1-yl)zirconium η⁴-1,4-diphenyl-1,3-butadiene;
diphenylamidoborane-bis-η⁵-(2-methylinden-1-yl)zirconium η⁴-2,4-hexadiene;
diphenylamidoborane-bis-η⁵-(2-methylinden-1-yl)zirconium η⁴-1,4-dinaphthyl-1,3-butadiene;
diphenylamidoborane-bis-η⁵-(2-methylinden-1-yl)zirconium η⁴-1-phenyl-1,3-pentadiene;
diphenylamidoborane-bis-η⁵-(2-methylinden-1-yl)zirconium η⁴-1,3-pentadiene;
diphenylamidoborane-bis-η⁵-(2-methyl-4-phenylinden-1-yl)zirconium dichloride;
diphenylamidoborane-bis-η⁵-(2-methyl-4-phenylinden-1-yl)zirconium dimethyl;
diphenylamidoborane-bis-η⁵-(2-methyl-4-phenylinden-1-yl)zirconium bis-dimethylamide;
diphenylamidoborane-bis-η⁵-(2-methyl-4-phenylinden-1-yl)zirconium 2-methyl-1,3-butadiene;
diphenylamidoborane-bis-η⁵-(2-methyl-4-phenylinden-1-yl)zirconium 2,3-dimethyl-1,3-butadiene;
diphenylamidoborane-bis-η⁵-(2-methyl-4-phenylinden-1-yl)zirconium 2-N,N-dimethylaminobenzyl;
diphenylamidoborane-bis-η⁵-(2-methyl-4-phenylinden-1-yl)zirconium allyl;
diphenylamidoborane-bis-η⁵-(2-methyl-4-phenylinden-1-yl)zirconium η⁴-1,4-diphenyl-1,3-butadiene;
diphenylamidoborane-bis-η⁵-(2-methyl-4-phenylinden-1-yl)zirconium η⁴-2,4-hexadiene;
diphenylamidoborane-bis-η⁵-(2-methyl-4-phenylinden-1-yl)zirconium η⁴-1,4-dinaphthyl-1,3-butadiene;
diphenylamidoborane-bis-η⁵-(2-methyl-4-phenylinden-1-yl)zirconium η⁴-1-phenyl-1,3-pentadiene;
diphenylamidoborane-bis-η⁵-(2-methyl-4-phenylinden-1-yl)zirconium η⁴-1,3-pentadiene;
diphenylamidoborane-bis-η⁵-(2-ethyl-4-phenylinden-1-yl)zirconium dichloride;
diphenylamidoborane-bis-η⁵-(2-ethyl-4-phenylinden-1-yl)zirconium dimethyl;
diphenylamidoborane-bis-η⁵-(2-ethyl-4-phenylinden-1-yl)zirconium bis-dimethylamide;
diphenylamidoborane-bis-η⁵-(2-ethyl-4-phenylinden-1-yl)zirconium 2-methyl-1,3-butadiene;
diphenylamidoborane-bis-η⁵-(2-ethyl-4-phenylinden-1-yl)zirconium 2,3-dimethyl-1,3-butadiene;
diphenylamidoborane-bis-η⁵-(2-ethyl-4-phenylinden-1-yl)zirconium 2-N,N-dimethylaminobenzyl;
diphenylamidoborane-bis-η⁵-(2-ethyl-4-phenylinden-1-yl)zirconium allyl;
diphenylamidoborane-bis-η⁵-(2-ethyl-4-phenylinden-1-yl)zirconium η⁴-1,4-diphenyl-1,3-butadiene;
diphenylamidoborane-bis-η⁵-(2-ethyl-4-phenylinden-1-yl)zirconium η⁴-2,4-hexadiene;
diphenylamidoborane-bis-η⁵-(2-ethyl-4-phenylinden-1-yl)zirconium η⁴-1,4-dinaphthyl-1,3-butadiene;
diphenylamidoborane-bis-η⁵-(2-ethyl-4-phenylinden-1-yl)zirconium η⁴-1-phenyl-1,3-pentadiene;
diphenylamidoborane-bis-η⁵-(2-ethyl-4-phenylinden-1-yl)zirconium η⁴-1,3-pentadiene;
diphenylamidoborane-bis-η⁵-(2-isopropyl-4-phenylinden-1-yl)zirconium dichloride;

diphenylamidoborane-bis-$\eta^5$-(2-isopropyl-4-phenylinden-1-yl)zirconium dimethyl;
diphenylamidoborane-bis-$\eta^5$-(2-isopropyl-4-phenylinden-1-yl)zirconium bis-dimethylamide;
diphenylamidoborane-bis-$\eta^5$-(2-isopropyl-4-phenylinden-1-yl)zirconium 2-methyl-1,3-butadiene;
diphenylamidoborane-bis-$\eta^5$-(2-isopropyl-4-phenylinden-1-yl)zirconium 2,3-dimethyl-1,3-butadiene;
diphenylamidoborane-bis-$\eta^5$-(2-isopropyl-4-phenylinden-1-yl)zirconium 2-N,N-dimethylaminobenzyl;
diphenylamidoborane-bis-$\eta^5$-(2-isopropyl-4-phenylinden-1-yl)zirconium allyl;
diphenylamidoborane-bis-$\eta^5$-(2-isopropyl-4-phenylinden-1-yl)zirconium $\eta^4$-1,4-diphenyl-1,3-butadiene;
diphenylamidoborane-bis-$\eta^5$-(2-isopropyl-4-phenylinden-1-yl)zirconium $\eta^4$-2,4-hexadiene;
diphenylamidoborane-bis-$\eta^5$-(2-isopropyl-4-phenylinden-1-yl)zirconium $\eta^4$-1,4-dinaphthyl-1,3-butadiene;
diphenylamidoborane-bis-$\eta^5$-(2-isopropyl-4-phenylinden-1-yl)zirconium $\eta^4$-1-phenyl-1,3-pentadiene;
diphenylamidoborane-bis-$\eta^5$-(2-isopropyl-4-phenylinden-1-yl)zirconium $\eta^4$-1,3-pentadiene;
diphenylamidoborane-bis-$\eta^5$-(2-methyl-4-naphthylinden-1-yl)zirconium dichloride;
diphenylamidoborane-bis-$\eta^5$-(2-methyl-4-naphthylinden-1-yl)zirconium dimethyl;
diphenylamidoborane-bis-$\eta^5$-(2-methyl-4-naphthylinden-1-yl)zirconium bis-dimethylamide;
diphenylamidoborane-bis-$\eta^5$-(2-methyl-4-naphthylinden-1-yl)zirconium 2-methyl-1,3-butadiene;
diphenylamidoborane-bis-$\eta^5$-(2-methyl-4-naphthylinden-1-yl)zirconium 2,3-dimethyl-1,3-butadiene;
diphenylamidoborane-bis-$\eta^5$-(2-methyl-4-naphthylinden-1-yl)zirconium 2-N,N-dimethylaminobenzyl;
diphenylamidoborane-bis-$\eta^5$-(2-methyl-4-naphthylinden-1-yl)zirconium allyl;
diphenylamidoborane-bis-$\eta^5$-(2-methyl-4-naphthylinden-1-yl)zirconium $\eta^4$-1,4-diphenyl-1,3-butadiene;
diphenylamidoborane-bis-$\eta^5$-(2-methyl-4-naphthylinden-1-yl)zirconium $\eta^4$-2,4-hexadiene;
diphenylamidoborane-bis-$\eta^5$-(2-methyl-4-naphthylinden-1-yl)zirconium $\eta^4$-1,4-dinaphthyl-1,3-butadiene;
diphenylamidoborane-bis-$\eta^5$-(2-methyl-4-naphthylinden-1-yl)zirconium $\eta^4$-1-phenyl-1,3-pentadiene;
diphenylamidoborane-bis-$\eta^5$-(2-methyl-4-naphthylinden-1-yl)zirconium $\eta^4$-1,3-pentadiene;
diphenylamidoborane-bis-$\eta^5$-(2-methyl-4-bis(3,5-trifluoromethyl)phenylinden-1-yl)zirconium dichloride;
diphenylamidoborane-bis-$\eta^5$-(2-methyl-4-bis(3,5-trifluoromethyl)phenylinden-1-yl)zirconium dimethyl;
diphenylamidoborane-bis-$\eta^5$-(2-methyl-4-bis(3,5-trifluoromethyl)phenylinden-1-yl)zirconium bis-dimethylamide;
diphenylamidoborane-bis-$\eta^5$-(2-methyl-4-bis(3,5-trifluoromethyl)phenylinden-1-yl)zirconium 2-methyl-1,3-butadiene;
diphenylamidoborane-bis-$\eta^5$-(2-methyl-4-bis(3,5-trifluoromethyl)phenylinden-1-yl)zirconium 2,3-dimethyl-1,3-butadiene;
diphenylamidoborane-bis-$\eta^5$-(2-methyl-4-bis(3,5-trifluoromethyl)phenylinden-1-yl)zirconium 2-N,N-dimethylaminobenzyl;
diphenylamidoborane-bis-$\eta^5$-(2-methyl-4-bis(3,5-trifluoromethyl)phenylinden-1-yl)zirconium allyl;
diphenylamidoborane-bis-$\eta^5$-(2-methyl-4-bis(3,5-trifluoromethyl)phenylinden-1-yl)zirconium $\eta^4$-1,4-diphenyl-1,3-butadiene;
diphenylamidoborane-bis-$\eta^5$-(2-methyl-4-bis(3,5-trifluoromethyl)phenylinden-1-yl)zirconium $\eta^4$-2,4-hexadiene;
diphenylamidoborane-bis-$\eta^5$-(2-methyl-4-bis(3,5-trifluoromethyl)phenylinden-1-yl)zirconium $\eta^4$-1,4-dinaphthyl-1,3-butadiene;
diphenylamidoborane-bis-$\eta^5$-(2-methyl-4-bis(3,5-trifluoromethyl)phenylinden-1-yl)zirconium $\eta^4$-1-phenyl-1,3-pentadiene;
diphenylamidoborane-bis-$\eta^5$-(2-methyl-4-bis(3,4-trifluoromethyl)phenylinden-1-yl)zirconium $\eta^4$-1,3-pentadiene;
diphenylamidoborane-bis-$\eta^5$-(2-ethyl-4-bis(3,5-trifluoromethyl)phenylinden-1-yl)zirconium dichloride;
diphenylamidoborane-bis-$\eta^5$-(2-ethyl-4-bis(3,5-trifluoromethyl)phenylinden-1-yl)zirconium dimethyl;
diphenylamidoborane-bis-$\eta^5$-(2-ethyl-4-bis(3,5-trifluoromethyl)phenylinden-1-yl)zirconium bis-dimethylamide;
diphenylamidoborane-bis-$\eta^5$-(2-ethyl-4-bis(3,5-trifluoromethyl)phenylinden-1-yl)zirconium 2-methyl-1,3-butadiene;
diphenylamidoborane-bis-$\eta^5$-(2-ethyl-4-bis(3,5-trifluoromethyl)phenylinden-1-yl)zirconium 2,3-dimethyl-1,3-butadiene;
diphenylamidoborane-bis-$\eta^5$-(2-ethyl-4-bis(3,5-trifluoromethyl)phenylinden-1-yl)zirconium 2-N,N-dimethylaminobenzyl;
diphenylamidoborane-bis-$\eta^5$-(2-ethyl-4-bis(3,5-trifluoromethyl)phenylinden-1-yl)zirconium allyl;
diphenylamidoborane-bis-$\eta^5$-(2-ethyl-4-bis(3,5-trifluoromethyl)phenylinden-1-yl)zirconium $\eta^4$-1,4-diphenyl-1,3-butadiene;
diphenylamidoborane-bis-$\eta^5$-(2-ethyl-4-bis(3,5-trifluoromethyl)phenylinden-1-yl)zirconium $\eta^4$-2,4-hexadiene;
diphenylamidoborane-bis-$\eta^5$-(2-ethyl-4-bis(3,5-trifluoromethyl)phenylinden-1-yl)zirconium $\eta^4$-1,4-dinaphthyl-1,3-butadiene;
diphenylamidoborane-bis-$\eta^5$-(2-ethyl-4-bis(3,5-trifluoromethyl)phenylinden-1-yl)zirconium $\eta^4$-1-phenyl-1,3-pentadiene;
diphenylamidoborane-bis-$\eta^5$-(2-ethyl-4-bis(3,5-trifluoromethyl)phenylinden-1-yl)zirconium $\eta^4$-1,3-pentadiene;
diphenylamidoborane-bis-$\eta^5$-(2-isopropyl-4-bis(3,5-trifluoromethyl)phenylinden-1-yl)zirconium dichloride;
diphenylamidoborane-bis-$\eta^5$-(2-isopropyl-4-bis(3,5-trifluoromethyl)phenylinden-1-yl)zirconium dimethyl;
diphenylamidoborane-bis-$\eta^5$-(2-isopropyl-4-bis(3,5-trifluoromethyl)phenylinden-1-yl)zirconium bis-dimethylamide;
diphenylamidoborane-bis-$\eta^5$-(2-isopropyl-4-bis(3,5-trifluoromethyl)phenylinden-1-yl)zirconium 2-methyl-1,3-butadiene;
diphenylamidoborane-bis-$\eta^5$-(2-isopropyl-4-bis(3,5-trifluoromethyl)phenylinden-1-yl)zirconium 2,3-dimethyl-1,3-butadiene;
diphenylamidoborane-bis-$\eta^5$-(2-isopropyl-4-bis(3,5-trifluoromethyl)phenylinden-1-yl)zirconium 2-N,N-dimethylaminobenzyl;
diphenylamidoborane-bis-$\eta^5$-(2-isopropyl-4-bis(3,5-trifluoromethyl)phenylinden-1-yl)zirconium allyl;
diphenylamidoborane-bis-$\eta^5$-(2-isopropyl-4-bis(3,5-trifluoromethyl)phenylinden-1-yl)zirconium $\eta^4$-1,4-diphenyl-1,3-butadiene;
diphenylamidoborane-bis-$\eta^5$-(2-isopropyl-4-bis(3,5-trifluoromethyl)phenylinden-1-yl)zirconium $\eta^4$-2,4-hexadiene;

diphenylamidoborane-bis-η⁵-(2-isopropyl-4-bis(3,5-trifluoromethyl)phenylinden-1-yl)zirconium η⁴-1,4-dinaphthyl-1,3-butadiene;
diphenylamidoborane-bis-η⁵-(2-isopropyl-4-bis(3,5-trifluoromethyl)phenylinden-1-yl)zirconium η⁴-1-phenyl-1,3-pentadiene;
diphenylamidoborane-bis-η⁵-(2-isopropyl-4-bis(3,5-trifluoromethyl)phenylinden-1-yl)zirconium η⁴-1,3-pentadiene;
diphenylamidoborane-bis-η⁵-(3-isopropylinden-1-yl)zirconium dichloride;
diphenylamidoborane-bis-η⁵-(3-isopropylinden-1-yl)zirconium dimethyl;
diphenylamidoborane-bis-η⁵-(3-isopropylinden-1-yl)zirconium bis-dimethylamide;
diphenylamidoborane-bis-η⁵-(3-isopropylinden-1-yl)zirconium 2-methyl-1,3-butadiene;
diphenylamidoborane-bis-η⁵-(3-isopropylinden-1-yl)zirconium 2,3-dimethyl-1,3-butadiene;
diphenylamidoborane-bis-η⁵-(3-isopropylinden-1-yl)zirconium 2-N,N-dimethylaminobenzyl;
diphenylamidoborane-bis-η⁵-(3-isopropylinden-1-yl)zirconium allyl;
diphenylamidoborane-bis-η⁵-(3-isopropylinden-1-yl)zirconium η⁴-,1,4-diphenyl-1,3-butadiene;
diphenylamidoborane-bis-η⁵-(3-isopropylinden-1-yl)zirconium η⁴-2,4-hexadiene;
diphenylamidoborane-bis-η⁵-(3-isopropylinden-1-yl)zirconium η⁴-1,4-dinaphthyl-1,3-butadiene;
diphenylamidoborane-bis-η⁵-(3-isopropylinden-1-yl)zirconium η⁴-1-phenyl-1,3-pentadiene;
diphenylamidoborane-bis-η⁵-(3-isopropylinden-1-yl)zirconium η⁴-1,3-pentadiene;
diphenylamidoborane-bis-η⁵-(3-t-butylinden-1-yl)zirconium dichloride;
diphenylamidoborane-bis-η⁵-(3-t-butylinden-1-yl)zirconium dimethyl;
diphenylamidoborane-bis-η⁵-(3-t-butylinden-1-yl)zirconium bis-dimethylamide;
diphenylamidoborane-bis-η⁵-(3-t-butylinden-1-yl)zirconium 2-methyl-1,3-butadiene;
diphenylamidoborane-bis-η⁵-(3-t-butylinden-1-yl)zirconium 2,3-dimethyl-1,3-butadiene;
diphenylamidoborane-bis-η⁵-(3-t-butylinden-1-yl)zirconium 2-N,N-dimethylaminobenzyl;
diphenylamidoborane-bis-η⁵-(3-t-butylinden-1-yl)zirconium allyl;
diphenylamidoborane-bis-η⁵-(3-t-butylinden-1-yl)zirconium η⁴-1,4-diphenyl-1,3-butadiene;
diphenylamidoborane-bis-η⁵-(3-t-butylinden-1-yl)zirconium η⁴-2,4-hexadiene;
diphenylamidoborane-bis-η⁵-(3-t-butylinden-1-yl)zirconium η⁴-1,4-dinaphthyl-1,3-butadiene;
diphenylamidoborane-bis-η⁵-(3-t-butylinden-1-yl)zirconium η⁴-1-phenyl-1,3-pentadiene;
diphenylamidoborane-bis-η⁵-(3-t-butylinden-1-yl)zirconium η⁴-1,3-pentadiene;
bis(trimethylsilyl)amidoborane-bis-η⁵-cyclopentadienylzirconium dichloride;
bis(trimethylsilyl)amidoborane-bis-η⁵-cyclopentadienylzirconium dimethyl;
bis(trimethylsilyl)amidoborane-bis-η⁵-cyclopentadienylzirconium bis-dimethylamide;
bis(trimethylsilyl)amidoborane-bis-η⁵-cyclopentadienylzirconium 2-methyl-1,3-butadiene;
bis(trimethylsilyl)amidoborane-bis-η⁵-cyclopentadienylzirconium 2,3-dimethyl-1,3-butadiene;
bis(trimethylsilyl)amidoborane-bis-η⁵-cyclopentadienylzirconium 2-N,N-dimethylaminobenzyl;
bis(trimethylsilyl)amidoborane-bis-η⁵-cyclopentadienylzirconium allyl;
bis(trimethylsilyl)amidoborane-bis-η⁵-cyclopentadienylzirconium η⁴-1,4-diphenyl-1,3-butadiene;
bis(trimethylsilyl)amidoborane-bis-η⁵-cyclopentadienylzirconium η⁴-2,4-hexadiene;
bis(trimethylsilyl)amidoborane-bis-η⁵-cyclopentadienylzirconium η⁴-1,4-dinaphthyl-1,3-butadiene;
bis(trimethylsilyl)amidoborane-bis-η⁵-cyclopentadienylzirconium η⁴-1-phenyl-1,3-pentadiene;
bis(trimethylsilyl)amidoborane-bis-η⁵-cyclopentadienylzirconium η⁵-1,3-pentadiene;
bis(trimethylsilyl)amidoborane-bis-η⁵-inden-1-ylzirconium dichloride;
bis(trimethylsilyl)amidoborane-bis-η⁵-inden-1-ylzirconium dimethyl;
bis(trimethylsilyl)amidoborane-bis-η⁵-inden-1-ylzirconium bis-dimethylamide;
bis(trimethylsilyl)amidoborane-bis-η⁵-inden-1-ylzirconium 2-methyl-1,3-butadiene;
bis(trimethylsilyl)amidoborane-bis-η⁵-inden-1-ylzirconium 2,3-dimethyl-1,3-butadiene;
bis(trimethylsilyl)amidoborane-bis-η⁵-inden-1-ylzirconium 2-N,N-dimethylaminobenzyl;
bis(trimethylsilyl)amidoborane-bis-η⁵-inden-1-ylzirconium allyl;
bis(trimethylsilyl)amidoborane-bis-η⁵-inden-1-ylzirconium η⁴-1,4-diphenyl-1,3-butadiene;
bis(trimethylsilyl)amidoborane-bis-η⁵-inden-1-ylzirconium η⁴-2,4-hexadiene;
bis(trimethylsilyl)amidoborane-bis-η⁵-inden-1-ylzirconium η⁴-1,4-dinaphthyl-1,3-butadiene;
bis(trimethylsilyl)amidoborane-bis-η⁵-inden-1-ylzirconium η⁴-1-phenyl-1,3-pentadiene;
bis(trimethylsilyl)amidoborane-bis-η⁵-inden-1-ylzirconium η⁴-1,3-pentadiene;
bis(trimethylsilyl)amidoborane-bis-η⁵-(2-methylinden-1-yl)zirconium dichloride;
bis(trimethylsilyl)amidoborane-bis-η⁵-(2-methylinden-1-yl)zirconium dimethyl;
bis(trimethylsilyl)amidoborane-bis-η⁵-(2-methylinden-1-yl)zirconium bis-dimethylamide;
bis(trimethylsilyl)amidoborane-bis-η⁵-(2-methylinden-1-yl)zirconium 2-methyl-1,3-butadiene;
bis(trimethylsilyl)amidoborane-bis-η⁵-(2-methylinden-1-yl)zirconium 2,3-dimethyl-1,3-butadiene;
bis(trimethylsilyl)amidoborane-bis-η⁵-(2-methylinden-1-yl)zirconium 2-N,N-dimethylaminobenzyl;
bis(trimethylsilyl)amidoborane-bis-η⁵-(2-methylinden-1-yl)zirconium allyl;
bis(trimethylsilyl)amidoborane-bis-η⁵-(2-methylinden-1-yl)zirconium η⁴-1,4-diphenyl-1,3-butadiene;
bis(trimethylsilyl)amidoborane-bis-η⁵-(2-methylinden-1-yl)zirconium η⁴-2,4-hexadiene;
bis(trimethylsilyl)amidoborane-bis-η⁵-(2-methylinden-1-yl)zirconium η⁴-1,4-dinaphthyl-1,3-butadiene;
bis(trimethylsilyl)amidoborane-bis-η⁵-(2-methylinden-1-yl)zirconium η⁴-1-phenyl-1,3-pentadiene;
bis(trimethylsilyl)amidoborane-bis-η⁵-(2-methylinden-1-yl)zirconium η⁴-1,3-pentadiene;
bis(trimethylsilyl)amidoborane-bis-η⁵-(2-methyl-4-phenylinden-1-yl)zirconium dichloride;
bis(trimethylsilyl)amidoborane-bis-η⁵-(2-methyl-4-phenylinden-1-yl)zirconium dimethyl;

bis(trimethylsilyl)amidoborane-bis-$\eta^5$-(2-methyl-4-phenylinden-1-yl)zirconium bis-dimethylamide;
bis(trimethylsilyl)amidoborane-bis-$\eta^5$-(2-methyl-4-phenylinden-1-yl)zirconium 2-methyl-1,3-butadiene;
bis(trimethylsilyl)amidoborane-bis-$\eta^5$-(2-methyl-4-phenylinden-1-yl)zirconium 2,3-dimethyl-1,3-butadiene;
bis(trimethylsilyl)amidoborane-bis-$\eta^5$-(2-methyl-4-phenylinden-1-yl)zirconium 2-N,N-dimethylaminobenzyl;
bis(trimethylsilyl)amidoborane-bis-$\eta^5$-(2-methyl-4-phenylinden-1-yl)zirconium allyl;
bis(trimethylsilyl)amidoborane-bis-$\eta^5$-(2-methyl-4-phenylinden-1-yl)zirconium $\eta^4$-1,4-diphenyl-1,3-butadiene;
bis(trimethylsilyl)amidoborane-bis-$\eta^5$-(2-methyl-4-phenylinden-1-yl)zirconium $\eta^4$-2,4-hexadiene;
bis(trimethylsilyl)amidoborane-bis-$\eta^5$-(2-methyl-4-phenylinden-1-yl)zirconium $\eta^4$-1,4-dinaphthyl-1,3-butadiene;
bis(trimethylsilyl)amidoborane-bis-$\eta^5$-(2-methyl-4-phenylinden-1-yl)zirconium $\eta^4$-1-phenyl-1,3-pentadiene;
bis(trimethylsilyl)amidoborane-bis-$\eta^5$-(2-methyl-4-phenylinden-1-yl)zirconium $\eta^4$-1,3-pentadiene;
bis(trimethylsilyl)amidoborane-bis-$\eta^5$-(2-methyl-4-naphthylinden-1-yl)zirconium dichloride;
bis(trimethylsilyl)amidoborane-bis-$\eta^5$-(2-methyl-4-naphthylinden-1-yl)zirconium dimethyl;
bis(trimethylsilyl)amidoborane-bis-$\eta^5$-(2-methyl-4-naphthylinden-1-yl)zirconium bis-dimethylamide;
bis(trimethylsilyl)amidoborane-bis-$\eta^5$-(2-methyl-4-naphthylinden-1-yl)zirconium 2-methyl-1,3-butadiene;
bis(trimethylsilyl)amidoborane-bis-$\eta^5$-(2-methyl-4-naphthylinden-1-yl)zirconium 2,3-dimethyl-1,3-butadiene;
bis(trimethylsilyl)amidoborane-bis-$\eta^5$-(2-methyl-4-naphthylinden-1-yl)zirconium 2-N,N-dimethylaminobenzyl;
bis(trimethylsilyl)amidoborane-bis-$\eta^5$-(2-methyl-4-naphthylinden-1-yl)zirconium allyl;
bis(trimethylsilyl)amidoborane-bis-$\eta^5$-(2-methyl-4-naphthylinden-1-yl)zirconium $\eta^4$-1,4-diphenyl-1,3-butadiene;
bis(trimethylsilyl)amidoborane-bis-$\eta^5$-(2-methyl-4-naphthylinden-1-yl)zirconium $\eta^4$-2,4-hexadiene;
bis(trimethylsilyl)amidoborane-bis-$\eta^5$-(2-methyl-4-naphthylinden-1-yl)zirconium $\eta^4$-1,4-dinaphthyl-1,3-butadiene;
bis(trimethylsilyl)amidoborane-bis-$\eta^5$-(2-methyl-4-naphthylinden-1-yl)zirconium $\eta^4$-1-phenyl-1,3-pentadiene;
bis(trimethylsilyl)amidoborane-bis-$\eta^5$-(2-methyl-4-naphthylinden-1-yl)zirconium $\eta^4$-1,3-pentadiene;
bis(trimethylsilyl)amidoborane-bis-$\eta^5$-(3-isopropylinden-1-yl)zirconium dichloride;
bis(trimethylsilyl)amidoborane-bis-$\eta^5$-(3-isopropylinden-1-yl)zirconium dimethyl;
bis(trimethylsilyl)amidoborane-bis-$\eta^5$-(3-isopropylinden-1-yl)zirconium bis-dimethylamide;
bis(trimethylsilyl)amidoborane-bis-$\eta^5$-(3-isopropylinden-1-yl)zirconium 2-methyl-1,3-butadiene;
bis(trimethylsilyl)amidoborane-bis-$\eta^5$-(3-isopropylinden-1-yl)zirconium 2,3-dimethyl-1,3-butadiene;
bis(trimethylsilyl)amidoborane-bis-$\eta^5$-(3-isopropylinden-1-yl)zirconium 2-N,N-dimethylaminobenzyl;
bis(trimethylsilyl)amidoborane-bis-$\eta^5$-(3-isopropylinden-1-yl)zirconium allyl;
bis(trimethylsilyl)amidoborane-bis-$\eta^5$-(3-isopropylinden-1-yl)zirconium $\eta^4$-1,4-diphenyl-1,3-butadiene;
bis(trimethylsilyl)amidoborane-bis-$\eta^5$-(3-isopropylinden-1-yl)zirconium $\eta^4$-2,4-hexadiene;
bis(trimethylsilyl)amidoborane-bis-$\eta^5$-(3-isopropylinden-1-yl)zirconium $\eta^4$-1,4-dinaphthyl-1,3-butadiene;
bis(trimethylsilyl)amidoborane-bis-$\eta^5$-(3-isopropylinden-1-yl)zirconium $\eta^4$-1-phenyl-1,3-pentadiene;
bis(trimethylsilyl)amidoborane-bis-$\eta^5$-(3-isopropylinden-1-yl)zirconium $\eta^4$-1,3-pentadiene;
bis(trimethylsilyl)amidoborane-bis-$\eta^5$-(3-t-butylinden-1-yl)zirconium dichloride;
bis(trimethylsilyl)amidoborane-bis-$\eta^5$-(3-t-butylinden-1-yl)zirconium dimethyl;
bis(trimethylsilyl)amidoborane-bis-$\eta^5$-(3-t-butylinden-1-yl)zirconium bis-dimethylamide;
bis(trimethylsilyl)amidoborane-bis-$\eta^5$-(3-t-butylinden-1-yl)zirconium 2-methyl-1,3-butadiene;
bis(trimethylsilyl)amidoborane-bis-$\eta^5$-(3-t-butylinden-1-yl)zirconium 2,3-dimethyl-1,3-butadiene;
bis(trimethylsilyl)amidoborane-bis-$\eta^5$-(3-t-butylinden-1-yl)zirconium 2-N,N-dimethylaminobenzyl;
bis(trimethylsilyl)amidoborane-bis-$\eta^5$-(3-t-butylinden-1-yl)zirconium allyl;
bis(trimethylsilyl)amidoborane-bis-$\eta^5$-(3-t-butylinden-1-yl)zirconium $\eta^4$-1,4-diphenyl-1,3-butadiene;
bis(trimethylsilyl)amidoborane-bis-$\eta^5$-(3-t-butylinden-1-yl)zirconium $\eta^4$-2,4-hexadiene;
bis(trimethylsilyl)amidoborane-bis-$\eta^5$-(3-t-butylinden-1-yl)zirconium $\eta^4$-1,4-dinaphthyl-1,3-butadiene;
bis(trimethylsilyl)amidoborane-bis-$\eta^5$-(3-t-butylinden-1-yl)zirconium $\eta^4$-1-phenyl-1,3-pentadiene;
bis(trimethylsilyl)amidoborane-bis-$\eta^5$-(3-t-butylinden-1-yl)zirconium $\eta^4$-1,3-pentadiene;
bis(diisopropylamido)diborane-1,2-bis-$\eta^5$-(2-methyl-4-phenylinden-1-yl)zirconium dichloride;
bis(diisopropylamido)diborane-1,2-bis-$\eta^5$-(2-methyl-4-phenylinden-1-yl)zirconium dimethyl;
bis(diisopropylamido)diborane-1,2-bis-$\eta^5$-(2-methyl-4-phenylinden-1-yl)zirconium bis-dimethylamide;
bis(diisopropylamido)diborane-1,2-bis-$\eta^5$-(2-methyl-4-phenylinden-1-yl)zirconium 2-methyl-1,3-butadiene;
bis(diisopropylamido)diborane-1,2-bis-$\eta^5$-(2-methyl-4-phenylinden-1-yl)zirconium 2,3-dimethyl-1,3-butadiene;
bis(diisopropylamido)diborane-1,2-bis-$\eta^5$-(2-methyl-4-phenylinden-1-yl)zirconium 2-N,N-dimethylaminobenzyl;
bis(diisopropylamido)diborane-1,2-bis-$\eta^5$-(2-methyl-4-phenylinden-1-yl)zirconium allyl;
bis(diisopropylamido)diborane-1,2-bis-$\eta^5$-(2-methyl-4-phenylinden-1-yl)zirconium $\eta^4$-1,4-diphenyl-1,3-butadiene;
bis(diisopropylamido)diborane-1,2-bis-$\eta^5$-(2-methyl-4-phenylinden-1-yl)zirconium $\eta^4$-2,4-hexadiene;
bis(diisopropylamido)diborane-1,2-bis-$\eta^5$-(2-methyl-4-phenylinden-1-yl)zirconium $\eta^4$-1,4-dinaphthyl-1,3-butadiene;
bis(diisopropylamido)diborane-1,2-bis-$\eta^5$-(2-methyl-4-phenylinden-1-yl)zirconium $\eta^4$-1-phenyl-1,3-pentadiene;
bis(diisopropylamido)diborane-1,2-bis-$\eta^5$-(2-methyl-4-phenylinden-1-yl)zirconium $\eta^4$-1,3-pentadiene;
dimethylamidoborane-bis-$\eta^5$-cyclopentadienyl hafnium dichloride;
dimethylamidoborane-bis-$\eta^5$-cyclopentadienyl hafnium dimethyl;
dimethylamidoborane-bis-$\eta^5$-cyclopentadienyl hafnium bis-dimethylamide;
dimethylamidoborane-bis-$\eta^5$-cyclopentadienyl hafnium 2-methyl-1,3-butadiene;

dimethylamidoborane-bis-$\eta^5$-cyclopentadienyl hafnium 2,3-dimethyl-1,3-butadiene;
dimethylamidoborane-bis-$\eta^5$-cyclopentadienyl hafnium 2-N,N-dimethylaminobenzyl;
dimethylamidoborane-bis-$\eta^5$-cyclopentadienyl hafnium allyl;
dimethylamidoborane-bis-$\eta^5$-cyclopentadienyl hafnium $\eta^4$-1,4-diphenyl-1,3-butadiene;
dimethylamidoborane-bis-$\eta^5$-cyclopentadienyl hafnium $\eta^4$-2,4-hexadiene;
dimethylamidoborane-bis-$\eta^5$-cyclopentadienyl hafnium $\eta^4$-1,4-dinaphthyl-1,3-butadiene;
dimethylamidoborane-bis-$\eta^5$-cyclopentadienyl hafnium $\eta^4$-1-phenyl-1,3-pentadiene;
dimethylamidoborane-bis-$\eta^5$-cyclopentadienyl hafnium $\eta^5$-1,3-pentadiene;
dimethylamidoborane-bis-$\eta^5$-n-butylcyclopentadienyl hafnium dichloride;
dimethylamidoborane-bis-$\eta^5$-n-butylcyclopentadienyl hafnium dimethyl;
dimethylamidoborane-bis-$\eta^5$-n-butylcyclopentadienyl hafnium bis-dimethylamide;
dimethylamidoborane-bis-$\eta^5$-n-butylcyclopentadienyl hafnium 2-methyl-1,3-butadiene;
dimethylamidoborane-bis-$\eta^5$-n-butylcyclopentadienyl hafnium 2,3-dimethyl-1,3-butadiene;
dimethylamidoborane-bis-$\eta^5$-n-butylcyclopentadienyl hafnium 2-N,N-dimethylaminobenzyl;
dimethylamidoborane-bis-$\eta^5$-n-butylcyclopentadienyl hafnium allyl;
dimethylamidoborane-bis-$\eta^5$-n-butylcyclopentadienyl hafnium $\eta^4$-1,4-diphenyl-1,3-butadiene;
dimethylamidoborane-bis-$\eta^5$-n-butylcyclopentadienyl hafnium $\eta^4$-2,4-hexadiene;
dimethylamidoborane-bis-$\eta^5$-n-butylcyclopentadienyl hafnium $\eta^4$-1,4-dinaphthyl-1,3-butadiene;
dimethylamidoborane-bis-$\eta^5$-n-butylcyclopentadienyl hafnium $\eta^4$-1-phenyl-1,3-pentadiene;
dimethylamidoborane-bis-$\eta^5$-n-butylcyclopentadienyl hafnium $\eta^5$-1,3-pentadiene;
dimethylamidoborane-bis-$\eta^5$-inden-1-ylhafnium dichloride;
dimethylamidoborane-bis-$\eta^5$-inden-1-ylhafnium dimethyl;
dimethylamidoborane-bis-$\eta^5$-inden-1-ylhafnium bis-dimethylamide;
dimethylamidoborane-bis-$\eta^5$-inden-1-ylhafnium 2-methyl-1,3-butadiene;
dimethylamidoborane-bis-$\eta^5$-inden-1-ylhafnium 2,3-dimethyl-1,3-butadiene;
dimethylamidoborane-bis-$\eta^5$-inden-1-ylhafnium 2-N,N-dimethylaminobenzyl;
dimethylamidoborane-bis-$\eta^5$-inden-1-ylhafnium allyl;
dimethylamidoborane-bis-$\eta^5$-inden-1-ylhafnium $\eta^4$-1,4-diphenyl-1,3-butadiene;
dimethylamidoborane-bis-$\eta^5$-inden-1-ylhafnium $\eta^4$-2,4-hexadiene;
dimethylamidoborane-bis-$\eta^5$-inden-1-ylhafnium $\eta^4$-1,4-dinaphthyl-1,3-butadiene;
dimethylamidoborane-bis-$\eta^5$-inden-1-ylhafnium $\eta^4$-1-phenyl-1,3-pentadiene;
dimethylamidoborane-bis-$\eta^5$-inden-1-ylhafnium $\eta^4$-1,3-pentadiene;
dimethylamidoborane-bis-$\eta^5$-(2-methylinden-1-yl)hafnium dichloride;
dimethylamidoborane-bis-$\eta^5$-(2-methylinden-1-yl)hafnium dimethyl;
dimethylamidoborane-bis-$\eta^5$-(2-methylinden-1-yl)hafnium bis-dimethylamide;
dimethylamidoborane-bis-$\eta^5$-(2-methylinden-1-yl)hafnium 2-methyl-1,3-butadiene;
dimethylamidoborane-bis-$\eta^5$-(2-methylinden-1-yl)hafnium 2,3-dimethyl-1,3-butadiene;
dimethylamidoborane-bis-$\eta^5$-(2-methylinden-1-yl)hafnium 2-N,N-dimethylaminobenzyl;
dimethylamidoborane-bis-$\eta^5$-(2-methylinden-1-yl)hafnium allyl;
dimethylamidoborane-bis-$\eta^5$-(2-methylinden-1-yl)hafnium $\eta^4$-1,4-diphenyl-1,3-butadiene;
dimethylamidoborane-bis-$\eta^5$-(2-methylinden-1-yl)hafnium $\eta^4$-2,4-hexadiene;
dimethylamidoborane-bis-$\eta^5$-(2-methylinden-1-yl)hafnium $\eta^4$-1,4-dinaphthyl-1,3-butadiene;
dimethylamidoborane-bis-$\eta^5$-(2-methylinden-1-yl)hafnium $\eta^4$-1-phenyl-1,3-pentadiene;
dimethylamidoborane-bis-$\eta^5$-(2-methylinden-1-yl)hafnium $\eta^4$-1,3-pentadiene;
dimethylamidoborane-bis-$\eta^5$-(2-methyl-4-phenylinden-1-yl)hafnium dichloride;
dimethylamidoborane-bis-$\eta^5$-(2-methyl-4-phenylinden-1-yl)hafnium dimethyl;
dimethylamidoborane-bis-$\eta^5$-(2-methyl-4-phenylinden-1-yl)hafnium bis-dimethylamide;
dimethylamidoborane-bis-$\eta^5$-(2-methyl-4-phenylinden-1-yl)hafnium 2-methyl-1,3-butadiene;
dimethylamidoborane-bis-$\eta^5$-(2-methyl-4-phenylinden-1-yl)hafnium 2,3-dimethyl-1,3-butadiene;
dimethylamidoborane-bis-$\eta^5$-(2-methyl-4-phenylinden-1-yl)hafnium 2-N,N-dimethylaminobenzyl;
dimethylamidoborane-bis-$\eta^5$-(2-methyl-4-phenylinden-1-yl)hafnium allyl;
dimethylamidoborane-bis-$\eta^5$-(2-methyl-4-phenylinden-1-yl)hafnium $\eta^4$-1,4-diphenyl-1,3-butadiene;
dimethylamidoborane-bis-$\eta^5$-(2-methyl-4-phenylinden-1-yl)hafnium $\eta^4$-2,4-hexadiene;
dimethylamidoborane-bis-$\eta^5$-(2-methyl-4-phenylinden-1-yl)hafnium $\eta^4$-1,4-dinaphthyl-1,3-butadiene;
dimethylamidoborane-bis-$\eta^5$-(2-methyl-4-phenylinden-1-yl)hafnium $\eta^4$-1-phenyl-1,3-pentadiene;
dimethylamidoborane-bis-$\eta^5$-(2-methyl-4-phenylinden-1-yl)hafnium $\eta^4$-1,3-pentadiene;
dimethylamidoborane-bis-$\eta^5$-(2-methyl-4-naphthylinden-1-yl)hafnium dichloride;
dimethylamidoborane-bis-$\eta^5$-(2-methyl-4-naphthylinden-1-yl)hafnium dimethyl;
dimethylamidoborane-bis-$\eta^5$-(2-methyl-4-naphthylinden-1-yl)hafnium bis-dimethylamide;
dimethylamidoborane-bis-$\eta^5$-(2-methyl-4-naphthylinden-1-yl)hafnium 2-methyl-1,3-butadiene;
dimethylamidoborane-bis-$\eta^5$-(2-methyl-4-naphthylinden-1-yl)hafnium 2,3-dimethyl-1,3-butadiene;
dimethylamidoborane-bis-$\eta^5$-(2-methyl-4-naphthylinden-1-yl)hafnium 2-N,N-dimethylaminobenzyl;
dimethylamidoborane-bis-$\eta^5$-(2-methyl-4-naphthylinden-1-yl)hafnium allyl;
dimethylamidoborane-bis-$\eta^5$-(2-methyl-4-naphthylinden-1-yl)hafnium $\eta^4$-1,4-diphenyl-1,3-butadiene;
dimethylamidoborane-bis-$\eta^5$-(2-methyl-4-naphthylinden-1-yl)hafnium $\eta^4$-2,4-hexadiene;
dimethylamidoborane-bis-$\eta^5$-(2-methyl-4-naphthylinden-1-yl)hafnium $\eta^4$-1,4-dinaphthyl-1,3-butadiene;
dimethylamidoborane-bis-$\eta^5$-(2-methyl-4-naphthylinden-1-yl)hafnium $\eta^4$-1-phenyl-1,3-pentadiene;
dimethylamidoborane-bis-$\eta^5$-(2-methyl-4-naphthylinden-1-yl)hafnium $\eta^4$-1,3-pentadiene;
dimethylamidoborane-bis-$\eta^5$-(3-isopropylinden-1-yl)hafnium dichloride;

dimethylamidoborane-bis-$\eta^5$-(3-isopropylinden-1-yl)hafnium dimethyl;
dimethylamidoborane-bis-$\eta^5$-(3-isopropylinden-1-yl)hafnium bis-dimethylamide;
dimethylamidoborane-bis-$\eta^5$-(3-isopropylinden-1-yl)hafnium 2-methyl-1,3-butadiene;
dimethylamidoborane-bis-$\eta^5$-(3-isopropylinden-1-yl)hafnium 2,3-dimethyl-1,3-butadiene;
dimethylamidoborane-bis-$\eta^5$-(3-isopropylinden-1-yl)hafnium 2-N,N-dimethylaminobenzyl;
dimethylamidoborane-bis-$\eta^5$-(3-isopropylinden-1-yl)hafnium allyl;
dimethylamidoborane-bis-$\eta^5$-(3-isopropylinden-1-yl)hafnium $\eta^4$-1,4-diphenyl-1,3-butadiene;
dimethylamidoborane-bis-$\eta^5$-(3-isopropylinden-1-yl)hafnium $\eta^4$-2,4-hexadiene;
dimethylamidoborane-bis-$\eta^5$-(3-isopropylinden-1-yl)hafnium $\eta^4$-1,4-dinaphthyl-1,3-butadiene;
dimethylamidoborane-bis-$\eta^5$-(3-isopropylinden-1-yl)hafnium $\eta^4$-1-phenyl-1,3-pentadiene;
dimethylamidoborane-bis-$\eta^5$-(3-isopropylinden-1-yl)hafnium $\eta^4$-1,3-pentadiene;
dimethylamidoborane-bis-$\eta^5$-(3-t-butylinden-1-yl)hafnium dichloride;
dimethylamidoborane-bis-$\eta^5$-(3-t-butylinden-1-yl)hafnium dimethyl;
dimethylamidoborane-bis-$\eta^5$-(3-t-butylinden-1-yl)hafnium bis-dimethylamide;
dimethylamidoborane-bis-$\eta^5$-(3-t-butylinden-1-yl)hafnium 2-methyl-1,3-butadiene;
dimethylamidoborane-bis-$\eta^5$-(3-t-butylinden-1-yl)hafnium 2,3-dimethyl-1,3-butadiene;
dimethylamidoborane-bis-$\eta^5$-(3-t-butylinden-1-yl)hafnium 2-N,N-dimethylaminobenzyl;
dimethylamidoborane-bis-$\eta^5$-(3-t-butylinden-1-yl)hafnium allyl;
dimethylamidoborane-bis-$\eta^5$-(3-t-butylinden-1-yl)hafnium $\eta^4$-1,4-diphenyl-1,3-butadiene;
dimethylamidoborane-bis-$\eta^5$-(3-t-butylinden-1-yl)hafnium $\eta^4$-2,4-hexadiene;
dimethylamidoborane-bis-$\eta^5$-(3-t-butylinden-1-yl)hafnium $\eta^4$-1,4-dinaphthyl-1,3-butadiene;
dimethylamidoborane-bis-$\eta^5$-(3-t-butylinden-1-yl)hafnium $\eta^4$-1-phenyl-1,3-pentadiene;
dimethylamidoborane-bis-$\eta^5$-(3-t-butylinden-1-yl)hafnium $\eta^4$-1,3-pentadiene;
diisopropylamidoborane-bis-$\eta^5$-cyclopentadienylhafnium dichloride;
diisopropylamidoborane-bis-$\eta^5$-cyclopentadienylhafnium dimethyl;
diisopropylamidoborane-bis-$\eta^5$-cyclopentadienylhafnium bis-dimethylamide;
diisopropylamidoborane-bis-$\eta^5$-cyclopentadienylhafnium 2-methyl-1,3-butadiene;
diisopropylamidoborane-bis-$\eta^5$-cyclopentadienylhafnium 2,3-dimethyl-1,3-butadiene;
diisopropylamidoborane-bis-$\eta^5$-cyclopentadienylhafnium 2-N,N-dimethylaminobenzyl;
diisopropylamidoborane-bis-$\eta^5$-cyclopentadienylhafnium allyl;
diisopropylamidoborane-bis-$\eta^5$-cyclopentadienylhafnium $\eta^4$-1,4-diphenyl-1,3-butadiene;
diisopropylamidoborane-bis-$\eta^5$-cyclopentadienylhafnium $\eta^4$-2,4-hexadiene;
diisopropylamidoborane-bis-$\eta^5$-cyclopentadienylhafnium $\eta^4$-1,4-dinaphthyl-1,3-butadiene;
diisopropylamidoborane-bis-$\eta^5$-cyclopentadienylhafnium $\eta^4$-1-phenyl-1,3-pentadiene;
diisopropylamidoborane-bis-$\eta^5$-cyclopentadienylhafnium $\eta^5$-1,3-pentadiene;
diisopropylamidoborane-bis-$\eta^5$-inden-1-ylhafnium dichloride;
diisopropylamidoborane-bis-$\eta^5$-inden-1-ylhafnium dimethyl;
diisopropylamidoborane-bis-$\eta^5$-inden-1-ylhafnium bis-dimethylamide;
diisopropylamidoborane-bis-$\eta^5$-inden-1-ylhafnium 2-methyl-1,3-butadiene;
diisopropylamidoborane-bis-$\eta^5$-inden-1-ylhafnium 2,3-dimethyl-1,3-butadiene;
diisopropylamidoborane-bis-$\eta^5$-inden-1-ylhafnium 2-N,N-dimethylaminobenzyl;
diisopropylamidoborane-bis-$\eta^5$-inden-1-ylhafnium allyl;
diisopropylamidoborane-bis-$\eta^5$-inden-1-ylhafnium $\eta^4$-1,4-diphenyl-1,3-butadiene;
diisopropylamidoborane-bis-$\eta^5$-inden-1-ylhafnium $\eta^4$-2,4-hexadiene;
diisopropylamidoborane-bis-$\eta^5$-inden-1-ylhafnium $\eta^4$-1,4-dinaphthyl-1,3-butadiene;
diisopropylamidoborane-bis-$\eta^5$-inden-1-ylhafnium $\eta^4$-1-phenyl-1,3-pentadiene;
diisopropylamidoborane-bis-$\eta^5$-inden-1-ylhafnium $\eta^4$-1,3-pentadiene;
diisopropylamidoborane-bis-$\eta^5$-(2-methylinden-1-yl)hafnium dichloride;
diisopropylamidoborane-bis-$\eta^5$-(2-methylinden-1-yl)hafnium dimethyl;
diisopropylamidoborane-bis-$\eta^5$-(2-methylinden-1-yl)hafnium bis-dimethylamide;
diisopropylamidoborane-bis-$\eta^5$-(2-methylinden-1-yl)hafnium 2-methyl-1,3-butadiene;
diisopropylamidoborane-bis-$\eta^5$-(2-methylinden-1-yl)hafnium 2,3-dimethyl-1,3-butadiene;
diisopropylamidoborane-bis-$\eta^5$-(2-methylinden-1-yl)hafnium 2-N,N-dimethylaminobenzyl;
diisopropylamidoborane-bis-$\eta^5$-(2-methylinden-1-yl)hafnium allyl;
diisopropylamidoborane-bis-$\eta^5$-(2-methylinden-1-yl)hafnium $\eta^4$-1,4-diphenyl-1,3-butadiene;
diisopropylamidoborane-bis-$\eta^5$-(2-methylinden-1-yl)hafnium $\eta^4$-2,4-hexadiene;
diisopropylamidoborane-bis-$\eta^5$-(2-methylinden-1-yl)hafnium $\eta^4$-1,4-dinaphthyl-1,3-butadiene;
diisopropylamidoborane-bis-$\eta^5$-(2-methylinden-1-yl)hafnium $\eta^4$-1-phenyl-1,3-pentadiene;
diisopropylamidoborane-bis-$\eta^5$-(2-methylinden-1-yl)hafnium $\eta^4$-1,3-pentadiene;
diisopropylamidoborane-bis-$\eta^5$-(2-methyl-4-phenylinden-1-yl)hafnium dichloride;
diisopropylamidoborane-bis-$\eta^5$-(2-methyl-4-phenylinden-1-yl)hafnium dimethyl;
diisopropylamidoborane-bis-$\eta^5$-(2-methyl-4-phenylinden-1-yl)hafnium bis-dimethylamide;
diisopropylamidoborane-bis-$\eta^5$-(2-methyl-4-phenylinden-1-yl)hafnium 2-methyl-1,3-butadiene;
diisopropylamidoborane-bis-$\eta^5$-(2-methyl-4-phenylinden-1-yl)hafnium 2,3-dimethyl-1,3-butadiene;
diisopropylamidoborane-bis-$\eta^5$-(2-methyl-4-phenylinden-1-yl)hafnium 2-N,N-dimethylaminobenzyl;
diisopropylamidoborane-bis-$\eta^5$-(2-methyl-4-phenylinden-1-yl)hafnium allyl;
diisopropylamidoborane-bis-$\eta^5$-(2-methyl-4-phenylinden-1-yl)hafnium $\eta^4$-1,4-diphenyl-1,3-butadiene;
diisopropylamidoborane-bis-$\eta^5$-(2-methyl-4-phenylinden-1-yl)hafnium $\eta^4$-2,4-hexadiene;

diisopropylamidoborane-bis-$\eta^5$-(2-methyl-4-phenylinden-1-yl)hafnium $\eta^4$-1,4-dinaphthyl-1,3-butadiene;
diisopropylamidoborane-bis-$\eta^5$-(2-methyl-4-phenylinden-1-yl)hafnium $\eta^4$-1-phenyl-1,3-pentadiene;
diisopropylamidoborane-bis-$\eta^5$-(2-methyl-4-phenylinden-1-yl)hafnium $\eta^4$-1,3-pentadiene;
diisopropylamidoborane-bis-$\eta^5$-(2-methyl-4-naphthylinden-1-yl)hafnium dichloride;
diisopropylamidoborane-bis-$\eta^5$-(2-methyl-4-naphthylinden-1-yl)hafnium dimethyl;
diisopropylamidoborane-bis-$\eta^5$-(2-methyl-4-naphthylinden-1-yl)hafnium bis-dimethylamide;
diisopropylamidoborane-bis-$\eta^5$-(2-methyl-4-naphthylinden-1-yl)hafnium 2-methyl-1,3-butadiene;
diisopropylamidoborane-bis-$\eta^5$-(2-methyl-4-naphthylinden-1-yl)hafnium 2,3-dimethyl-1,3-butadiene;
diisopropylamidoborane-bis-$\eta^5$-(2-methyl-4-naphthylinden-1-yl)hafnium 2-N,N-dimethylaminobenzyl;
diisopropylamidoborane-bis-$\eta^5$-(2-methyl-4-naphthylinden-1-yl)hafnium allyl;
diisopropylamidoborane-bis-$\eta^5$-(2-methyl-4-naphthylinden-1-yl)hafnium $\eta^4$-1,4-diphenyl-1,3-butadiene;
diisopropylamidoborane-bis-$\eta^5$-(2-methyl-4-naphthylinden-1-yl)hafnium $\eta^4$-2,4-hexadiene;
diisopropylamidoborane-bis-$\eta^5$-(2-methyl-4-naphthylinden-1-yl)hafnium $\eta^4$-1,4-dinaphthyl-1,3-butadiene;
diisopropylamidoborane-bis-$\eta^5$-(2-methyl-4-naphthylinden-1-yl)hafnium $\eta^4$-1-phenyl-1,3-pentadiene;
diisopropylamidoborane-bis-$\eta^5$-(2-methyl-4-naphthylinden-1-yl)hafnium $\eta^4$-1,3-pentadiene;
diisopropylamidoborane-bis-$\eta^5$-(3-isopropylinden-1-yl)hafnium dichloride;
diisopropylamidoborane-bis-$\eta^5$-(3-isopropylinden-1-yl)hafnium dimethyl;
diisopropylamidoborane-bis-$\eta^5$-(3-isopropylinden-1-yl)hafnium bis-dimethylamide;
diisopropylamidoborane-bis-$\eta^5$-(3-isopropylinden-1-yl)hafnium 2-methyl-1,3-butadiene;
diisopropylamidoborane-bis-$\eta^5$-(3-isopropylinden-1-yl)hafnium 2,3-dimethyl-1,3-butadiene;
diisopropylamidoborane-bis-$\eta^5$-(3-isopropylinden-1-yl)hafnium 2-N,N-dimethylaminobenzyl;
diisopropylamidoborane-bis-$\eta^5$-(3-isopropylinden-1-yl)hafnium allyl;
diisopropylamidoborane-bis-$\eta^5$-(3-isopropylinden-1-yl)hafnium $\eta^4$-1,4-diphenyl-1,3-butadiene;
diisopropylamidoborane-bis-$\eta^5$-(3-isopropylinden-1-yl)hafnium $\eta^4$-2,4-hexadiene;
diisopropylamidoborane-bis-$\eta^5$-(3-isopropylinden-1-yl)hafnium $\eta^4$-1,4-dinaphthyl-1,3-butadiene;
diisopropylamidoborane-bis-$\eta^5$-(3-isopropylinden-1-yl)hafnium $\eta^4$-1-phenyl-1,3-pentadiene;
diisopropylamidoborane-bis-$\eta^5$-(3-isopropylinden-1-yl)hafnium $\eta^4$-1,3-pentadiene;
diisopropylamidoborane-bis-$\eta^5$-(3-t-butylinden-1-yl)hafnium dichloride;
diisopropylamidoborane-bis-$\eta^5$-(3-t-butylinden-1-yl)hafnium dimethyl;
diisopropylamidoborane-bis-$\eta^5$-(3-t-butylinden-1-yl)hafnium bis-dimethylamide;
diisopropylamidoborane-bis-$\eta^5$-(3-t-butylinden-1-yl)hafnium 2-methyl-1,3-butadiene;
diisopropylamidoborane-bis-$\eta^5$-(3-t-butylinden-1-yl)hafnium 2,3-dimethyl-1,3-butadiene;
diisopropylamidoborane-bis-$\eta^5$-(3-t-butylinden-1-yl)hafnium 2-N,N-dimethylaminobenzyl;
diisopropylamidoborane-bis-$\eta^5$-(3-t-butylinden-1-yl)hafnium allyl;
diisopropylamidoborane-bis-$\eta^5$-(3-t-butylinden-1-yl)hafnium $\eta^4$-1,4-diphenyl-1,3-butadiene;
diisopropylamidoborane-bis-$\eta^5$-(3-t-butylinden-1-yl)hafnium $\eta^4$-2,4-hexadiene;
diisopropylamidoborane-bis-$\eta^5$-(3-t-butylinden-1-yl)hafnium $\eta^4$-1,4-dinaphthyl-1,3-butadiene;
diisopropylamidoborane-bis-$\eta^5$-(3-t-butylinden-1-yl)hafnium $\eta^4$-1-phenyl-1,3-pentadiene;
diisopropylamidoborane-bis-$\eta^5$-(3-t-butylinden-1-yl)hafnium $\eta^4$-1,3-pentadiene;
bis(trimethylsilyl)amidoborane-bis-$\eta^5$-cyclopentadienylhafnium dichloride;
bis(trimethylsilyl)amidoborane-bis-$\eta^5$-cyclopentadienylhafnium dimethyl;
bis(trimethylsilyl)amidoborane-bis-$\eta^5$-cyclopentadienylhafnium bis-dimethylamide;
bis(trimethylsilyl)amidoborane-bis-$\eta^5$-cyclopentadienylhafnium 2-methyl-1,3-butadiene;
bis(trimethylsilyl)amidoborane-bis-$\eta^5$-cyclopentadienylhafnium 2,3-dimethyl-1,3-butadiene;
bis(trimethylsilyl)amidoborane-bis-$\eta^5$-cyclopentadienylhafnium 2-N,N-dimethylaminobenzyl;
bis(trimethylsilyl)amidoborane-bis-$\eta^5$-cyclopentadienylhafnium allyl;
bis(trimethylsilyl)amidoborane-bis-$\eta^5$-cyclopentadienylhafnium $\eta^4$-1,4-diphenyl-1,3-butadiene;
bis(trimethylsilyl)amidoborane-bis-$\eta^5$-cyclopentadienylhafnium $\eta^4$-2,4-hexadiene,
bis(trimethylsilyl)amidoborane-bis-$\eta^5$-cyclopentadienylhafnium $\eta^4$-1,4-dinaphthyl-1,3-butadiene;
bis(trimethylsilyl)amidoborane-bis-$\eta^5$-cyclopentadienylhafnium $\eta^4$-1-phenyl-1,3-pentadiene;
bis(trimethylsilyl)amidoborane-bis-$\eta^5$-cyclopentadienylhafnium $\eta^5$-1,3-pentadiene;
bis(trimethylsilyl)amidoborane-bis-$\eta^5$-inden-1-ylhafnium dichloride;
bis(trimethylsilyl)amidoborane-bis-$\eta^5$-inden-1-ylhafnium dimethyl;
bis(trimethylsilyl)amidoborane-bis-$\eta^5$-inden-1-ylhafnium bis-dimethylamide;
bis(trimethylsilyl)amidoborane-bis-$\eta^5$-inden-1-ylhafnium 2-methyl-1,3-butadiene;
bis(trimethylsilyl)amidoborane-bis-$\eta^5$-inden-1-ylhafnium 2,3-dimethyl-1,3-butadiene;
bis(trimethylsilyl)amidoborane-bis-$\eta^5$-inden-1-ylhafnium 2-N,N-dimethylaminobenzyl;
bis(trimethylsilyl)amidoborane-bis-$\eta^5$-inden-1-ylhafnium allyl;
bis(trimethylsilyl)amidoborane-bis-$\eta^5$-inden-1-ylhafnium $\eta^4$-1,4-diphenyl-1,3-butadiene;
bis(trimethylsilyl)amidoborane-bis-$\eta^5$-inden-1-ylhafnium $\eta^4$-2,4-hexadiene;
bis(trimethylsilyl)amidoborane-bis-$\eta^5$-inden-1-ylhafnium $\eta^4$-1,4-dinaphthyl-1,3-butadiene;
bis(trimethylsilyl)amidoborane-bis-$\eta^5$-inden-1-ylhafnium $\eta^4$-1-phenyl-1,3-pentadiene;
bis(trimethylsilyl)amidoborane-bis-$\eta^5$-inden-1-ylhafnium $\eta^4$-1,3-pentadiene;
bis(trimethylsilyl)amidoborane-bis-$\eta^5$-(2-methylinden-1-yl)hafnium dichloride;
bis(trimethylsilyl)amidoborane-bis-$\eta^5$-(2-methylinden-1-yl)hafnium dimethyl;

bis(trimethylsilyl)amidoborane-bis-$\eta^5$-(2-methylinden-1-yl)hafnium bis-dimethylamide;
bis(trimethylsilyl)amidoborane-bis-$\eta^5$-(2-methylinden-1-yl)hafnium 2-methyl-1,3-butadiene;
bis(trimethylsilyl)amidoborane-bis-$\eta^5$-(2-methylinden-1-yl)hafnium 2,3-dimethyl-1,3-butadiene;
bis(trimethylsilyl)amidoborane-bis-$\eta^5$-(2-methylinden-1-yl)hafnium 2-N,N-dimethylaminobenzyl;
bis(trimethylsilyl)amidoborane-bis-$\eta^5$-(2-methylinden-1-yl)hafnium allyl;
bis(trimethylsilyl)amidoborane-bis-$\eta^5$-(2-methylinden-1-yl)hafnium $\eta^4$-1,4-diphenyl-1,3-butadiene;
bis(trimethylsilyl)amidoborane-bis-$\eta^5$-(2-methylinden-1-yl)hafnium $\eta^4$-2,4-hexadiene;
bis(trimethylsilyl)amidoborane-bis-$\eta^5$-(2-methylinden-1-yl)hafnium $\eta^4$-1,4-dinaphthyl-1,3-butadiene;
bis(trimethylsilyl)amidoborane-bis-$\eta^5$-(2-methylinden-1-yl)hafnium $\eta^4$-1-phenyl-1,3-pentadiene;
bis(trimethylsilyl)amidoborane-bis-$\eta^5$-(2-methylinden-1-yl)hafnium $\eta^4$-1,3-pentadiene;
bis(trimethylsilyl)amidoborane-bis-$\eta^5$-(2-methyl-4-phenylinden-1-yl)hafnium dichloride;
bis(trimethylsilyl)amidoborane-bis-$\eta^5$-(2-methyl-4-phenylinden-1-yl)hafnium dimethyl;
bis(trimethylsilyl)amidoborane-bis-$\eta^5$-(2-methyl-4-phenylinden-1-yl)hafnium bis-dimethylamide;
bis(trimethylsilyl)amidoborane-bis-$\eta^5$-(2-methyl-4-phenylinden-1-yl)hafnium 2-methyl-1,3-butadiene;
bis(trimethylsilyl)amidoborane-bis-$\eta^5$-(2-methyl-4-phenylinden-1-yl)hafnium 2,3-dimethyl-1,3-butadiene;
bis(trimethylsilyl)amidoborane-bis-$\eta^5$-(2-methyl-4-phenylinden-1-yl)hafnium 2-N,N-dimethylaminobenzyl;
bis(trimethylsilyl)amidoborane-bis-$\eta^5$-(2-methyl-4-phenylinden-1-yl)hafnium allyl;
bis(trimethylsilyl)amidoborane-bis-$\eta^5$-(2-methyl-4-phenylinden-1-yl)hafnium $\eta^4$-1,4-diphenyl-1,3-butadiene;
bis(trimethylsilyl)amidoborane-bis-$\eta^5$-(2-methyl-4-phenylinden-1-yl)hafnium $\eta^4$-2,4-hexadiene;
bis(trimethylsilyl)amidoborane-bis-$\eta^5$-(2-methyl-4-phenylinden-1-yl)hafnium $\eta^4$-1,4-dinaphthyl-1,3-butadiene;
bis(trimethylsilyl)amidoborane-bis-$\eta^5$-(2-methyl-4-phenylinden-1-yl)hafnium $\eta^4$-1-phenyl-1,3-pentadiene;
bis(trimethylsilyl)amidoborane-bis-$\eta^5$-(2-methyl-4-phenylinden-1-yl)hafnium $\eta^4$-1,3-pentadiene;
bis(trimethylsilyl)amidoborane-bis-$\eta^5$-(2-methyl-4-naphthylinden-1-yl)hafnium dichloride;
bis(trimethylsilyl)amidoborane-bis-$\eta^5$-(2-methyl-4-naphthylinden-1-yl)hafnium dimethyl;
bis(trimethylsilyl)amidoborane-bis-$\eta^5$-(2-methyl-4-naphthylinden-1-yl)hafnium bis-dimethylamide;
bis(trimethylsilyl)amidoborane-bis-$\eta^5$-(2-methyl-4-naphthylinden-1-yl)hafnium 2-methyl-1,3-butadiene;
bis(trimethylsilyl)amidoborane-bis-$\eta^5$-(2-methyl-4-naphthylinden-1-yl)hafnium 2,3-dimethyl-1,3-butadiene;
bis(trimethylsilyl)amidoborane-bis-$\eta^5$-(2-methyl-4-naphthylinden-1-yl)hafnium 2-N,N-dimethylaminobenzyl;
bis(trimethylsilyl)amidoborane-bis-$\eta^5$-(2-methyl-4-naphthylinden-1-yl)hafnium allyl;
bis(trimethylsilyl)amidoborane-bis-$\eta^5$-(2-methyl-4-naphthylinden-1-yl)hafnium $\eta^4$-1,4-diphenyl-1,3-butadiene;
bis(trimethylsilyl)amidoborane-bis-$\eta^5$-(2-methyl-4-naphthylinden-1-yl)hafnium $\eta^4$-2,4-hexadiene;
bis(trimethylsilyl)amidoborane-bis-$\eta^5$-(2-methyl-4-naphthylinden-1-yl)hafnium $\eta^4$-1,4-dinaphthyl-1,3-butadiene;
bis(trimethylsilyl)amidoborane-bis-$\eta^5$-(2-methyl-4-naphthylinden-1-yl)hafnium $\eta^4$-1-phenyl-1,3-pentadiene;
bis(trimethylsilyl)amidoborane-bis-$\eta^5$-(2-methyl-4-naphthylinden-1-yl)hafnium $\eta^4$-1,3-pentadiene;
bis(trimethylsilyl)amidoborane-bis-$\eta^5$-(3-isopropylinden-1-yl)hafnium dichloride;
bis(trimethylsilyl)amidoborane-bis-$\eta^5$-(3-isopropylinden-1-yl)hafnium dimethyl;
bis(trimethylsilyl)amidoborane-bis-$\eta^5$-(3-isopropylinden-1-yl)hafnium bis-dimethylamide;
bis(trimethylsilyl)amidoborane-bis-$\eta^5$-(3-isopropylinden-1-yl)hafnium 2-methyl-1,3-butadiene;
bis(trimethylsilyl)amidoborane-bis-$\eta^5$-(3-isopropylinden-1-yl)hafnium 2,3-dimethyl-1,3-butadiene;
bis(trimethylsilyl)amidoborane-bis-$\eta^5$-(3-isopropylinden-1-yl)hafnium 2-N,N-dimethylaminobenzyl;
bis(trimethylsilyl)amidoborane-bis-$\eta^5$-(3-isopropylinden-1-yl)hafnium allyl;
bis(trimethylsilyl)amidoborane-bis-$\eta^5$-(3-isopropylinden-1-yl)hafnium $\eta^4$-1,4-diphenyl-1,3-butadiene;
bis(trimethylsilyl)amidoborane-bis-$\eta^5$-(3-isopropylinden-1-yl)hafnium $\eta^4$-2,4-hexadiene;
bis(trimethylsilyl)amidoborane-bis-$\eta^5$-(3-isopropylinden-1-yl)hafnium $\eta^4$-1,4-dinaphthyl-1,3-butadiene;
bis(trimethylsilyl)amidoborane-bis-$\eta^5$-(3-isopropylinden-1-yl)hafnium $\eta^4$-1-phenyl-1,3-pentadiene;
bis(trimethylsilyl)amidoborane-bis-$\eta^5$-(3-isopropylinden-1-yl)hafnium $\eta^4$-1,3-pentadiene;
bis(trimethylsilyl)amidoborane-bis-$\eta^5$-(3-t-butylinden-1-yl)hafnium dichloride;
bis(trimethylsilyl)amidoborane-bis-$\eta^5$-(3-t-butylinden-1-yl)hafnium dimethyl;
bis(trimethylsilyl)amidoborane-bis-$\eta^5$-(3-t-butylinden-1-yl)hafnium bis-dimethylamide;
bis(trimethylsilyl)amidoborane-bis-$\eta^5$-(3-t-butylinden-1-yl)hafnium 2-methyl-1,3-butadiene;
bis(trimethylsilyl)amidoborane-bis-$\eta^5$-(3-t-butylinden-1-yl)hafnium 2,3-dimethyl-1,3-butadiene;
bis(trimethylsilyl)amidoborane-bis-$\eta^5$-(3-t-butylinden-1-yl)hafnium 2-N,N-dimethylaminobenzyl;
bis(trimethylsilyl)amidoborane-bis-$\eta^5$-(3-t-butylinden-1-yl)hafnium allyl;
bis(trimethylsilyl)amidoborane-bis-$\eta^5$-(3-t-butylinden-1-yl)hafnium $\eta^4$-1,4-diphenyl-1,3-butadiene;
bis(trimethylsilyl)amidoborane-bis-$\eta^5$-(3-t-butylinden-1-yl)hafnium $\eta^4$-2,4-hexadiene;
bis(trimethylsilyl)amidoborane-bis-$\eta^5$-(3-t-butylinden-1-yl)hafnium $\eta^4$-1,4-dinaphthyl-1,3-butadiene;
bis(trimethylsilyl)amidoborane-bis-$\eta^5$-(3-t-butylinden-1-yl)hafnium $\eta^4$-1-phenyl-1,3-pentadiene;
bis(trimethylsilyl)amidoborane-bis-$\eta^5$-(3-t-butylinden-1-yl)hafnium $\eta^4$-1,3-pentadiene;
bis(diisopropylamido)diborane-1,2-bis-$\eta^5$-(2-methyl-4-phenylinden-1-yl)hafnium dichloride;
bis(diisopropylamido)diborane-1,2-bis-$\eta^5$-(2-methyl-4-phenylinden-1-yl)hafnium dimethyl;
bis(diisopropylamido)diborane-1,2-bis-$\eta^5$-(2-methyl-4-phenylinden-1-yl)hafnium bis-dimethylamide;
bis(diisopropylamido)diborane-1,2-bis-$\eta^5$-(2-methyl-4-phenylinden-1-yl)hafnium 2-methyl-1,3-butadiene;
bis(diisopropylamido)diborane-1,2-bis-$\eta^5$-(2-methyl-4-phenylinden-1-yl)hafnium 2,3-dimethyl-1,3-butadiene;
bis(diisopropylamido)diborane-1,2-bis-$\eta^5$-(2-methyl-4-phenylinden-1-yl)hafnium 2-N,N-dimethylaminobenzyl;
bis(diisopropylamido)diborane-1,2-bis-$\eta^5$-(2-methyl-4-phenylinden-1-yl)hafnium allyl;
bis(diisopropylamido)diborane-1,2-bis-$\eta^5$-(2-methyl-4-phenylinden-1-yl)hafnium $\eta^4$-1,4-diphenyl-1,3-butadiene;

bis(diisopropylamido)diborane-1,2-bis-$\eta^5$-(2-methyl-4-phenylinden-1-yl)hafnium $\eta^4$-2,4-hexadiene;

bis(diisopropylamido)diborane-1,2-bis-$\eta^5$-(2-methyl-4-phenylinden-1-yl)hafnium $\eta^4$-1,4-dinaphthyl-1,3-butadiene;

bis(diisopropylamido)diborane-1,2-bis-$\eta^5$-(2-methyl-4-phenylinden-1-yl)hafnium $\eta^4$-1-phenyl-1,3-pentadiene;

bis(diisopropylamido)diborane-1,2-bis-$\eta^5$-(2-methyl-4-phenylinden-1-yl)zirconium $\eta^4$-1,3-pentadiene;

($\eta^5$-tetramethylcyclopentadienyl)(tert-butylamido) diisopropylamidoborane titanium dichloride;

($\eta^5$-tetramethylcyclopentadienyl)(tert-butylamido) diisopropylamidoborane titanium dimethyl;

($\eta^5$-tetramethylcyclopentadienyl)(tert-butylamido) diisopropylamidoborane titanium bis-dimethylamide;

($\eta^5$-tetramethylcyclopentadienyl)(tert-butylamido) diisopropylamidoborane titanium 2-methyl-1,3-butadiene;

($\eta^5$-tetramethylcyclopentadienyl)(tert-butylamido) diisopropylamidoborane titanium 2,3-dimethyl-1,3-butadiene;

($\eta^5$-tetramethylcyclopentadienyl)(tert-butylamido) diisopropylamidoborane titanium 2-N,N-dimethylaminobenzyl;

($\eta^5$-tetramethylcyclopentadienyl)(tert-butylamido) diisopropylamidoborane titanium allyl;

($\eta^5$-tetramethylcyclopentadienyl)(tert-butylamido) diisopropylamidoborane titanium $\eta^4$-1,4-diphenyl-1,3-butadiene;

($\eta^5$-tetramethylcyclopentadienyl)(tert-butylamido) diisopropylamidoborane titanium $\eta^4$-2,4-hexadiene;

($\eta^5$-tetramethylcyclopentadienyl)(tert-butylamido) diisopropylamidoborane titanium $\eta^4$-1,4-dinaphthyl-1,3-butadiene;

($\eta^5$-tetramethylcyclopentadienyl)(tert-butylamido) diisopropylamidoborane titanium $\eta^4$-1-phenyl-1,3-pentadiene;

($\eta^5$-tetramethylcyclopentadienyl)(tert-butylamido) diisopropylamidoborane titanium $\eta^4$-1,3-pentadiene;

($\eta^5$-tetramethylcyclopentadienyl)(cyclohexylamido) diisopropylamidoborane titanium dichloride;

($\eta^5$-tetramethylcyclopentadienyl)(cyclohexylamido) diisopropylamidoborane titanium dimethyl;

($\eta^5$-tetramethylcyclopentadienyl)(cyclohexylamido) diisopropylamidoborane titanium bis-dimethylamide;

($\eta^5$-tetramethylcyclopentadienyl)(cyclohexylamido) diisopropylamidoborane titanium 2-methyl-1,3-butadiene;

($\eta^5$-tetramethylcyclopentadienyl)(cyclohexylamido) diisopropylamidoborane titanium 2,3-dimethyl-1,3-butadiene;

($\eta^5$-tetramethylcyclopentadienyl)(cyclohexylamido) diisopropylamidoborane titanium 2-N,N-dimethylaminobenzyl;

($\eta^5$-tetramethylcyclopentadienyl)(cyclohexylamido) diisopropylamidoborane titanium allyl;

($\eta^5$-tetramethylcyclopentadienyl)(cyclohexylamido) diisopropylamidoborane titanium $\eta^4$-1,4-diphenyl-1,3-butadiene;

($\eta^5$-tetramethylcyclopentadienyl)(cyclohexylamido) diisopropylamidoborane titanium $\eta^4$-2,4-hexadiene;

($\eta^5$-tetramethylcyclopentadienyl)(cyclohexylamido) diisopropylamidoborane titanium $\eta^4$-1,4-dinaphthyl-1,3-butadiene;

($\eta^5$-tetramethylcyclopentadienyl)(cyclohexylamido) diisopropylamidoborane titanium $\eta^4$-1-phenyl-1,3-pentadiene;

($\eta^5$-tetramethylcyclopentadienyl)(cyclohexylamido) diisopropylamidoborane titanium $\eta^4$-1,3-pentadiene;

($\eta^5$-tetramethylcyclopentadienyl)(tert-butylamido)bis (diisopropylamide) diborane titanium dichloride;

($\eta^5$-tetramethylcyclopentadienyl)(tert-butylamido)bis (diisopropylamide) diborane titanium dimethyl;

($\eta^5$-tetramethylcyclopentadienyl)(tert-butylamido)bis (diisopropylamide) diborane titanium bis-dimethylamide;

($\eta^5$-tetramethylcyclopentadienyl)(tert-butylamido)bis (diisopropylamide) diborane titanium 2-methyl-1,3-butadiene;

($\eta^5$-tetramethylcyclopentadienyl)(tert-butylamido)bis (diisopropylamide) diborane titanium 2,3-dimethyl-1,3-butadiene;

($\eta^5$-tetramethylcyclopentadienyl)(tert-butylamido)bis (diisopropylamide) diborane titanium 2-N,N-dimethylaminobenzyl;

($\eta^5$-tetramethylcyclopentadienyl)(tert-butylamido)bis (diisopropylamide) diborane titanium allyl;

($\eta^5$-tetramethylcyclopentadienyl)(tert-butylamido)bis (diisopropylamide) diborane titanium $\eta^4$-1,4-diphenyl-1,3-butadiene;

($\eta^5$-tetramethylcyclopentadienyl)(tert-butylamido)bis (diisopropylamide) diborane titanium $\eta^4$-2,4-hexadiene;

($\eta^5$-tetramethylcyclopentadienyl)(tert-butylamido)bis (diisopropylamide) diborane titanium $\eta^4$-1,4-dinaphthyl-1,3-butadiene;

($\eta^5$-tetramethylcyclopentadienyl)(tert-butylamido)bis (diisopropylamide) diborane titanium $\eta^4$-1-phenyl-1,3-pentadiene;

($\eta^5$-tetramethylcyclopentadienyl)(tert-butylamido)bis (diisopropylamide) diborane titanium $\eta^4$-1,3-pentadiene;

($\eta^5$-tetramethylcyclopentadienyl)(phenylamido) diisopropylamidoborane titanium dichloride;

($\eta^5$-tetramethylcyclopentadienyl)(phenylamido) diisopropylamidoborane titanium dimethyl;

($\eta^5$-tetramethylcyclopentadienyl)(phenylamido) diisopropylamidoborane titanium bis-dimethylamide;

($\eta^5$-tetramethylcyclopentadienyl)(phenylamido) diisopropylamidoborane titanium 2-methyl-1,3-butadiene;

($\eta^5$-tetramethylcyclopentadienyl)(phenylamido) diisopropylamidoborane titanium 2,3-dimethyl-1,3-butadiene;

($\eta^5$-tetramethylcyclopentadienyl)(phenylamido) diisopropylamidoborane titanium 2-N,N-dimethylaminobenzyl;

($\eta^5$-tetramethylcyclopentadienyl)(phenylamido) diisopropylamidoborane titanium allyl;

($\eta$5-tetramethylcyclopentadienyl)(phenylamido) diisopropylamidoborane titanium $\eta^4$-1,4-diphenyl-1,3-butadiene;

($\eta^5$-tetramethylcyclopentadienyl)(phenylamido) diisopropylamidoborane titanium $\eta^4$-2,4-hexadiene;

($\eta^5$-tetramethylcyclopentadienyl)(phenylamido) diisopropylamidoborane titanium $\eta^4$-1,4-dinaphthyl-1,3-butadiene;

($\eta^5$-tetramethylcyclopentadienyl)(phenylamido) diisopropylamidoborane titanium $\eta^4$-1-phenyl-1,3-pentadiene;

($\eta^5$-tetramethylcyclopentadienyl)(phenylamido) diisopropylamidoborane titanium $\eta^4$-1,3-pentadiene;

($\eta^5$-tetramethylcyclopentadienyl)(tert-butylamido) dimethylamidoborane titanium dichloride;

($\eta^5$-tetramethylcyclopentadienyl)(tert-butylamido) dimethylamidoborane titanium dimethyl;

($\eta^5$-tetramethylcyclopentadienyl)(tert-butylamido) dimethylamidoborane titanium bis-dimethylamide;

($\eta^5$-tetramethylcyclopentadienyl)(tert-butylamido) dimethylamidoborane titanium 2-methyl-1,3-butadiene;

($\eta^5$-tetramethylcyclopentadienyl)(tert-butylamido) dimethylamidoborane titanium 2,3-dimethyl-1,3-butadiene;

($\eta^5$-tetramethylcyclopentadienyl)(tert-butylamido) dimethylamidoborane titanium 2-N,N-dimethylaminobenzyl;

($\eta^5$-tetramethylcyclopentadienyl)(tert-butylamido) dimethylamidoborane titanium allyl;

($\eta^5$-tetramethylcyclopentadienyl)(tert-butylamido) dimethylamidoborane titanium $\eta^4$-1,4-diphenyl-1,3-butadiene;

($\eta^5$-tetramethylcyclopentadienyl)(tert-butylamido) dimethylamidoborane titanium $\eta^4$-2,4-hexadiene;

($\eta^5$-tetramethylcyclopentadienyl)(tert-butylamido) dimethylamidoborane titanium $\eta^4$-1,4-dinaphthyl-1,3-butadiene;

($\eta^5$-tetramethylcyclopentadienyl)(tert-butylamido) dimethylamidoborane titanium $\eta^4$-1-phenyl-1,3-pentadiene;

($\eta^5$-tetramethylcyclopentadienyl)(tert-butylamido) dimethylamidoborane titanium $\eta^4$-1,3-pentadiene;

($\eta^5$-inden-1-yl)(tert-butylamido)diisopropylamidoborane titanium dichloride;

($\eta^5$-inden-1-yl)(tert-butylamido)diisopropylamidoborane titanium dimethyl;

($\eta^5$-inden-1-yl)(tert-butylamido)diisopropylamidoborane titanium bis-dimethylamide;

($\eta^5$-inden-1-yl)(tert-butylamido)diisopropylamidoborane titanium 2-methyl-1,3-butadiene;

($\eta^5$-inden-1-yl)(tert-butylamido)diisopropylamidoborane titanium 2,3-dimethyl-1,3-butadiene;

($\eta^5$-inden-1-yl)(tert-butylamido)diisopropylamidoborane titanium 2-N,N-dimethylaminobenzyl;

($\eta^5$-inden-1-yl)(tert-butylamido)diisopropylamidoborane titanium allyl;

($\eta^5$-inden-1-yl)(tert-butylamido)diisopropylamidoborane titanium $\eta^4$-1,4-diphenyl-1,3-butadiene;

($\eta^5$-inden-1-yl)(tert-butylamido)diisopropylamidoborane titanium $\eta^4$-2,4-hexadiene;

($\eta^5$-inden-1-yl)(tert-butylamido)diisopropylamidoborane titanium $\eta^4$-1,4-dinaphthyl-1,3-butadiene;

($\eta^5$-inden-1-yl)(tert-butylamido)diisopropylamidoborane titanium $\eta^4$-1-phenyl-1,3-pentadiene;

($\eta^5$-inden-1-yl)(tert-butylamido)diisopropylamidoborane titanium $\eta^4$-1,3-pentadiene;

($\eta^5$-2,3-dimethyl-1-)(tert-butylamido) diisopropylamidoborane titanium dichloride;

($\eta^5$-2,3-dimethylinden-1-yl)(tert-butylamido) diisopropylamidoborane titanium dimethyl;

($\eta^5$-2,3-dimethylinden-1-yl)(tert-butylamido) diisopropylamidoborane titanium bis-dimethylamide;

($\eta^5$-2,3-dimethylinden-1-yl)(tert-butylamido) diisopropylamidoborane titanium 2-methyl-1,3-butadiene;

($\eta^5$-2,3-dimethylinden-1-yl)(tert-butylamido) diisopropylamidoborane titanium 2,3-dimethyl-1,3-butadiene;

($\eta^5$-2,3-dimethylinden-1-yl)(tert-butylamido) diisopropylamidoborane titanium 2-N,N-dimethylaminobenzyl;

($\eta^5$-2,3-dimethylinden-1-yl)(tert-butylamido) diisopropylamidoborane titanium allyl;

($\eta^5$-2,3-dimethylinden-1-yl)(tert-butylamido) diisopropylamidoborane titanium $\eta^4$-1,4-diphenyl-1,3-butadiene;

($\eta^5$-2,3-dimethylinden-1-yl)(tert-butylamido) diisopropylamidoborane titanium $\eta^4$-2,4-hexadiene;

($\eta^5$-2,3-dimethylinden-1-yl)(tert-butylamido) diisopropylamidoborane titanium $\eta^4$-1,4-dinaphthyl-1,3-butadiene;

($\eta^5$-2,3-dimethylinden-1-yl)(tert-butylamido) diisopropylamidoborane titanium $\eta^4$-1-phenyl-1,3-pentadiene;

($\eta^5$-2,3-dimethylinden-1-yl)(tert-butylamido) diisopropylamidoborane titanium $\eta^4$-1,3-pentadiene;

($\eta^5$-2-pyrrolidenylinden-1-yl)(tert-butylamido) diisopropylamidoborane titanium dichloride;

($\eta^5$-2-pyrrolidenylinden-1-yl)(tert-butylamido) diisopropylamidoborane titanium dimethyl;

($\eta^5$-2-pyrrolidenylinden-1-yl)(tert-butylamido) diisopropylamidoborane titanium bis-dimethylamide;

($\eta^5$-2-pyrrolidenylinden-1-yl)(tert-butylamido) diisopropylamidoborane titanium 2-methyl-1,3-butadiene;

($\eta^5$-2-pyrrolidenylinden-1-yl)(tert-butylamido) diisopropylamidoborane titanium 2,3-dimethyl-1,3-butadiene;

($\eta^5$-2-pyrrolidenylinden-1-yl)(tert-butylamido) diisopropylamidoborane titanium 2-N,N-dimethylaminobenzyl;

($\eta^5$-2-pyrrolidenylinden-1-yl)(tert-butylamido) diisopropylamidoborane titanium allyl;

($\eta^5$-2-pyrrolidenylinden-1-yl)(tert-butylamido) diisopropylamidoborane titanium $\eta^4$-1,4-diphenyl-1,3-butadiene;

($\eta^5$-2-pyrrolidenylinden-1-yl)(tert-butylamido) diisopropylamidoborane titanium $\eta^4$-2,4-hexadiene;

($\eta^5$-2-pyrrolidenylinden-1-yl)(tert-butylamido) diisopropylamidoborane titanium $\eta^4$-1,4-dinaphthyl-1,3-butadiene;

($\eta^5$-2-pyrrolidenylinden-1-yl)(tert-butylamido) diisopropylamidoborane titanium $\eta^4$-1-phenyl-1,3-pentadiene;

($\eta^5$-2-pyrrolidenylinden-1-yl)(tert-butylamido) diisopropylamidoborane titanium $\eta^4$-1,3-pentadiene;

bis-phenylamido-bis(diisopropylamido)diborane titanium dichloride;

bis-phenylamido-bis(diisopropylamido)diborane titanium dimethyl;

bis-phenylamido-bis(diisopropylamido)diborane titanium bis-dimethylamide;

bis-phenylamido-bis(diisopropylamido)diborane titanium 2-methyl-1,3-butadiene;

bis-phenylamido-bis(diisopropylamido)diborane titanium 2,3-dimethyl-1,3-butadiene;

bis-phenylamido-bis(diisopropylamido)diborane titanium 2-N,N-dimethylaminobenzyl;

bis-phenylamido-bis(diisopropylamido)diborane titanium allyl;

bis-phenylamido-bis(diisopropylamido)diborane titanium $\eta^4$-1,4-diphenyl-1,3-butadiene;

bis-phenylamido-bis(diisopropylamido)diborane titanium $\eta^4$-2,4-hexadiene;

bis-phenylamido-bis(diisopropylamido)diborane titanium $\eta^4$-1,4-dinaphthyl-1,3-butadiene;

bis-phenylamido-bis(diisopropylamido)diborane titanium $\eta^4$-1-phenyl-1,3-pentadiene;

bis-phenylamido-bis(diisopropylamido)diborane titanium $\eta^4$-1,3-pentadiene;

bis-2,6-disopropylphenylamido-bis(diisopropylamido) diborane titanium dichloride;

bis-2,6-disopropylphenylamido-bis(diisopropylamido) diborane titanium dimethyl;

bis-2,6-disopropylphenylamido-bis(diisopropylamido) diborane titanium bis-dimethylamide;
bis-2,6-disopropylphenylamido-bis(diisopropylamido) diborane titanium 2-methyl-1,3-butadiene;
bis-2,6-disopropylphenylamido-bis(diisopropylamido) diborane titanium 2,3-dimethyl-1,3-butadiene;
bis-2,6-disopropylphenylamido-bis(diisopropylamido) diborane titanium 2-N,N-dimethylaminobenzyl;
bis-2,6-disopropylphenylamido-bis(diisopropylamido) diborane titanium allyl;
bis-2,6-disopropylphenylamido-bis(diisopropylamido) diborane titanium $\eta^4$-1,4-diphenyl-1,3-butadiene;
bis-2,6-disopropylphenylamido-bis(diisopropylamido) diborane titanium $\eta^4$-2,4-hexadiene;
bis-2,6-disopropylphenylamido-bis(diisopropylamido) diborane titanium $\eta^4$-1,4-dinaphthyl-1,3-butadiene;
bis-2,6-disopropylphenylamido-bis(diisopropylamido) diborane titanium $\eta^4$-1-phenyl-1,3-pentadiene;
bis-2,6-disopropylphenylamido-bis(diisopropylamido) diborane titanium $\eta^4$-1,3-pentadiene;
bis-3,5-dimethylbenzylamido-bis(dimethylamido)diborane titanium dichloride;
bis-3,5-dimethylbenzylamido-bis(dimethylamido)diborane titanium dimethyl;
bis-3,5-dimethylbenzylamido-bis(dimethylamido)diborane titanium bis-dimethylamide;
bis-3,5-dimethylbenzylamido-bis(dimethylamido)diborane titanium 2-methyl-1,3-butadiene;
bis-3,5-dimethylbenzylamido-bis(dimethylamido)diborane titanium 2,3-dimethyl-1,3-butadiene;
bis-3,5-dimethylbenzylamido-bis(dimethylamido)diborane titanium 2-N,N-dimethylaminobenzyl;
bis-3,5-dimethylbenzylamido-bis(dimethylamido)diborane titanium allyl;
bis-3,5-dimethylbenzylamido-bis(dimethylamido)diborane titanium $\eta^4$-1,4-diphenyl-1,3-butadiene;
bis-3,5-dimethylbenzylamido-bis(dimethylamido)diborane titanium $\eta^4$-2,4-hexadiene;
bis-3,5-dimethylbenzylamido-bis(dimethylamido)diborane titanium $\eta^4$-1,4-dinaphthyl-1,3-butadiene;
bis-3,5-dimethylbenzylamido-bis(dimethylamido)diborane titanium $\eta^4$-1-phenyl-1,3-pentadiene;
bis-3,5-dimethylbenzylamido-bis(dimethylamido)diborane titanium $\eta^4$-1,3-pentadiene;
bis-2,6-dimethylbenzylamido-bis(dimethylamido)diborane titanium dichloride;
bis-2,6-dimethylbenzylamido-bis(dimethylamido)diborane titanium dimethyl;
bis-2,6-dimethylbenzylamido-bis(dimethylamido)diborane titanium bis-dimethylamide;
bis-2,6-dimethylbenzylamido-bis(dimethylamido)diborane titanium 2-methyl-1,3-butadiene;
bis-2,6-dimethylbenzylamido-bis(dimethylamido)diborane titanium 2,3-dimethyl-1,3-butadiene;
bis-2,6-dimethylbenzylamido-bis(dimethylamido)diborane titanium 2-N,N-dimethylaminobenzyl;
bis-2,6-dimethylbenzylamido-bis(dimethylamido)diborane titanium allyl;
bis-2,6-dimethylbenzylamido-bis(dimethylamido)diborane titanium $\eta^4$-1,4-diphenyl-1,3-butadiene;
bis-2,6-dimethylbenzylamido-bis(dimethylamido)diborane titanium $\eta^4$-2,4-hexadiene;
bis-2,6-dimethylbenzylamido-bis(dimethylamido)diborane titanium $\eta^4$-1,4-dinaphthyl-1,3-butadiene;
bis-2,6-dimethylbenzylamido-bis(dimethylamido)diborane titanium $\eta^4$-1-phenyl-1,3-pentadiene;
bis-2,6-dimethylbenzylamido-bis(dimethylamido)diborane titanium $\eta^4$-1,3-pentadiene;
bis-2,6-diisopropylphenylamido-bis(dimethylamido) diborane titanium dichloride;
bis-2,6-diisopropylphenylamido-bis(dimethylamido) diborane titanium dimethyl;
bis-2,6-diisopropylphenylamido-bis(dimethylamido) diborane titanium bis-dimethylamide;
bis-2,6-diisopropylphenylamido-bis(dimethylamido) diborane titanium 2-methyl-1,3-butadiene;
bis-2,6-diisopropylphenylamido-bis(dimethylamido) diborane titanium 2,3-dimethyl-1,3-butadiene;
bis-2,6-diisopropylphenylamido-bis(dimethylamido) diborane titanium 2-N,N-dimethylaminobenzyl;
bis-2,6-diisopropylphenylamido-bis(dimethylamido) diborane titanium allyl;
bis-2,6-diisopropylphenylamido-bis(dimethylamido) diborane titanium $\eta^4$-1,4-diphenyl-1,3-butadiene;
bis-2,6-diisopropylphenylamido-bis(dimethylamido) diborane titanium $\eta^4$-2,4-hexadiene;
bis-2,6-diisopropylphenylamido-bis(dimethylamido) diborane titanium $\eta^4$-1,4-dinaphthyl-1,3-butadiene;
bis-2,6-diisopropylphenylamido-bis(dimethylamido) diborane titanium $\eta^4$-1-phenyl-1,3-pentadiene;
bis-2,6-diisopropylphenylamido-bis(dimethylamido) diborane titanium $\eta^4$-1,3-pentadiene;
bis-2,6-diisopropylphenylamido-bis(bis(trimethylsilyl) amido)diborane titanium dichloride;
bis-2,6-diisopropylphenylamido-bis(bis(trimethylsilyl) amido)diborane titanium dimethyl;
bis-2,6-diisopropylphenylamido-bis(bis(trimethylsilyl) amido)diborane titanium bis-dimethylamide;
bis-2,6-diisopropylphenylamido-bis(bis(trimethylsilyl) amido)diborane titanium 2-methyl-1,3-butadiene;
bis-2,6-diisopropylphenylamido-bis(bis(trimethylsilyl) amido)diborane titanium 2,3-dimethyl-1,3-butadiene;
bis-2,6-diisopropylphenylamido-bis(bis(trimethylsilyl) amido)diborane titanium 2-N,N-dimethylaminobenzyl;
bis-2,6-diisopropylphenylamido-bis(bis(trimethylsilyl) amido)diborane titanium allyl;
bis-2,6-diisopropylphenylamido-bis(bis(trimethylsilyl) amido)diborane titanium $\eta^4$-1,4-diphenyl-1,3-butadiene;
bis-2,6-diisopropylphenylamido-bis(bis(trimethylsilyl) amido)diborane titanium $\eta^4$-2,4-hexadiene;
bis-2,6-diisopropylphenylamido-bis(bis(trimethylsilyl) amido)diborane titanium $\eta^4$-1,4-dinaphthyl-1,3-butadiene;
bis-2,6-diisopropylphenylamido-bis(bis(trimethylsilyl) amido)diborane titanium $\eta^4$-1-phenyl-1,3-pentadiene;
bis-2,6-diisopropylphenylamido-bis(bis(trimethylsilyl) amido)diborane titanium $\eta^4$-1,3-pentadiene;
bis-2,6-diisopropylphenylamido-bis(diisopropylamido) diborane zirconium dichloride;
bis-2,6-diisopropylphenylamido-bis(diisopropylamido) diborane zirconium dimethyl;
bis-2,6-diisopropylphenylamido-bis(diisopropylamido) diborane zirconium bis-dimethylamide;
bis-2,6-diisopropylphenylamido-bis(diisopropylamido) diborane zirconium 2-methyl-1,3-butadiene;
bis-2,6-diisopropylphenylamido-bis(diisopropylamido) diborane zirconium 2,3-dimethyl-1,3-butadiene;
bis-2,6-diisopropylphenylamido-bis(diisopropylamido) diborane zirconium 2-N,N-dimethylaminobenzyl;
bis-2,6-diisopropylphenylamido-bis(diisopropylamido) diborane zirconium allyl;
bis-2,6-diisopropylphenylamido-bis(diisopropylamido) diborane zirconium $\eta^4$-1,4-diphenyl-1,3-butadiene;
bis-2,6-diisopropylphenylamido-bis(diisopropylamido) diborane zirconium $\eta^4$-2,4-hexadiene;

bis-2,6-diisopropylphenylamido-bis(diisopropylamido) diborane zirconium $\eta^4$-1,4-dinaphthyl-1,3-butadiene;
bis-2,6-diisopropylphenylamido-bis(diisopropylamido) diborane zirconium $\eta^4$-1-phenyl-1,3-pentadiene;
bis-2,6-diisopropylphenylamido-bis(diisopropylamido) diborane zirconium $\eta^4$-1,3-pentadiene;
bis-2-tert-butylphenylamido-bis(diisopropylamido)diborane titanium dichloride;
bis-2-tert-butylphenylamido-bis(diisopropylamido)diborane titanium dimethyl;
bis-2-tert-butylphenylamido-bis(diisopropylamido)diborane titanium bis-dimethylamide;
bis-2-tert-butylphenylamido-bis(diisopropylamido)diborane titanium 2-methyl-1,3-butadiene;
bis-2-tert-butylphenylamido-bis(diisopropylamido)diborane titanium 2,3-dimethyl-1,3-butadiene;
bis-2-tert-butylphenylamido-bis(diisopropylamido)diborane titanium 2-N,N-dimethylaminobenzyl;
bis-2-tert-butylphenylamido-bis(diisopropylamido)diborane titanium allyl;
bis-2-tert-butylphenylamido-bis(diisopropylamido)diborane titanium $\eta^4$-1,4-diphenyl-1,3-butadiene;
bis-2-tert-butylphenylamido-bis(diisopropylamido)diborane titanium $\eta^4$-2,4-hexadiene;
bis-2-tert-butylphenylamido-bis(diisopropylamido)diborane titanium $\eta^4$-1,4-dinaphthyl-1,3-butadiene;
bis-2-tert-butylphenylamido-bis(diisopropylamido)diborane titanium $\eta^4$-1-phenyl-1,3-pentadiene; and
bis-2-tert-butylphenylamido-bis(diisopropylamido)diborane titanium $\eta^4$-1,3-pentadiene.

A further preferred class of Group 4 transition metal complexes of the present invention are represented in previously defined formulas 4–9 wherein T is:

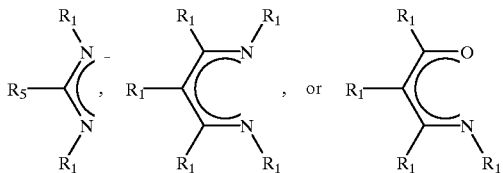

including such structures where two $R^1$ groups and $R^5$ are linked such as in 1,3,4,6,7,8, hexahydro-pyrimido[1,2-a] pyrimidinate, shown below:

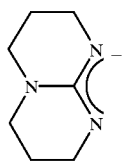

In the foregoing species, it is believed, without wishing to be bound by such belief, that the ligand group, T, is connected to Z via the heteroatoms thereof.

Specific, but not limiting, examples of the foregoing metal complexes included within the invention are:
N,N'-disopropyl-phenyl-amidinate borane-bis-$\eta^5$-cyclopentadienylzirconium dichloride;
N,N'-disopropyl-phenyl-amidinate borane-bis-$\eta^5$-cyclopentadienylzirconium dimethyl;
N,N'-disopropyl-phenyl-amidinate borane-bis-$\eta^5$-cyclopentadienylzirconium bis-dimethylamide;
N,N'-disopropyl-phenyl-amidinate borane-bis-$\eta^5$-cyclopentadienylzirconium 2-methyl-1,3-butadiene;
N,N'-disopropyl-phenyl-amidinate borane-bis-$\eta^5$-cyclopentadienylzirconium 2,3-dimethyl-1,3-butadiene;
N,N'-disopropyl-phenyl-amidinate borane-bis-$\eta^5$-cyclopentadienylzirconium 2-N,N-dimethylaminobenzyl;
N,N'-disopropyl-phenyl-amidinate borane-bis-$\eta^5$-cyclopentadienylzirconium allyl;
N,N'-disopropyl-phenyl-amidinate borane-bis-$\eta^5$-cyclopentadienylzirconium $\eta^4$-1,4-diphenyl-1,3-butadiene;
N,N'-disopropyl-phenyl-amidinate borane-bis-$\eta^5$-cyclopentadienylzirconium $\eta^4$-2,4-hexadiene;
N,N'-disopropyl-phenyl-amidinate borane-bis-$\eta^5$-cyclopentadienylzirconium $\eta^4$-1,4-dinaphthyl-1,3-butadiene;
N,N'-disopropyl-phenyl-amidinate borane-bis-$\eta^5$-cyclopentadienylzirconium $\eta^4$-1-phenyl-1,3-pentadiene;
N,N'-disopropyl-phenyl-amidinate borane-bis-$\eta^5$-cyclopentadienylzirconium $\eta^4$-1,3-pentadiene;
N,N'-disopropyl-3-phenyl-1,3-diketimine borane-bis-$\eta^5$-cyclopentadienylzirconium dichloride;
N,N'-disopropyl-3-phenyl-1,3-diketimine borane-bis-$\eta^5$-cyclopentadienylzirconium dimethyl;
N,N'-disopropyl-3-phenyl-1,3-diketimine borane-bis-$\eta^5$-cyclopentadienylzirconium bis-dimethylamide;
N,N'-disopropyl-3-phenyl-1,3-diketimine borane-bis-$\eta^5$-cyclopentadienylzirconium 2-methyl-1,3-butadiene;
N,N'-disopropyl-3-phenyl-1,3-diketimine borane-bis-$\eta^5$-cyclopentadienylzirconium 2,3-dimethyl-1,3-butadiene;
N,N'-disopropyl-3-phenyl-1,3-diketimine borane-bis-$\eta^5$-cyclopentadienylzirconium 2-N,N-dimethylaminobenzyl;
N,N'-disopropyl-3-phenyl-1,3-diketimine borane-bis-$\eta^5$-cyclopentadienylzirconium allyl;
N,N'-disopropyl-3-phenyl-1,3-diketimine borane-bis-$\eta^5$-cyclopentadienylzirconium $\eta^4$-1,4-diphenyl-1,3-butadiene;
N,N'-disopropyl-3-phenyl-1,3-diketimine borane-bis-$\eta^5$-cyclopentadienylzirconium $\eta^4$-2,4-hexadiene;
N,N'-disopropyl-3-phenyl-1,3-diketimine borane-bis-$\eta^5$-cyclopentadienylzirconium $\eta^4$-1,4-dinaphthyl-1,3-butadiene;
N,N'-disopropyl-3-phenyl-1,3-diketimine borane-bis-$\eta^5$-cyclopentadienylzirconium $\eta^4$-1-phenyl-1,3-pentadiene;
N,N'-disopropyl-3-phenyl-1,3-diketimine borane-bis-$\eta^5$-cyclopentadienylzirconium $\eta^4$-1,3-pentadiene;
N,N'-disopropyl-dimethylguanidinate borane-bis-$\eta^5$-cyclopentadienylzirconium dichloride;
N,N'-disopropyl-dimethylguanidinate borane-bis-$\eta^5$-cyclopentadienylzirconium dimethyl;
N,N'-disopropyl-dimethylguanidinate borane-bis-$\eta^5$-cyclopentadienylzirconium bis-dimethylamide;
N,N'-disopropyl-dimethylguanidinate borane-bis-$\eta^5$-cyclopentadienylzirconium 2-methyl-1,3-butadiene;
N,N'-disopropyl-dimethylguanidinate borane-bis-$\eta^5$-cyclopentadienylzirconium 2,3-dimethyl-1,3-butadiene;
N,N'-disopropyl-dimethylguanidinate borane-bis-$\eta^5$-cyclopentadienylzirconium 2-N,N-dimethylaminobenzyl;
N,N'-disopropyl-dimethylguanidinate borane-bis-$\eta^5$-cyclopentadienylzirconium allyl;
N,N'-disopropyl-dimethylguanidinate borane-bis-$\eta^5$-cyclopentadienylzirconium $\eta^4$-1,4-diphenyl-1,3-butadiene;
N,N'-disopropyl-dimethylguanidinate borane-bis-$\eta^5$-cyclopentadienylzirconium $\eta^4$-2,4-hexadiene;
N,N'-disopropyl-dimethylguanidinate borane-bis-$\eta^5$-cyclopentadienylzirconium $\eta^4$-1,4-dinaphthyl-1,3-butadiene;
N,N'-disopropyl-dimethylguanidinate borane-bis-$\eta^5$-cyclopentadienylzirconium $\eta^4$-1-phenyl-1,3-pentadiene;

N,N'-disopropyl-dimethylguanidinate borane-bis-η$^5$-cyclopentadienylzirconium η$^4$-1,3-pentadiene;
1,3,4,6,7,8-hexahydro-pyrimido[1,2-a]pyrimidinate borane-bis-η$^5$-inden-1-ylzirconium dichloride;
1,3,4,6,7,8-hexahydro-pyrimido[1,2-a]pyrimidinate borane-bis-η$^5$-inden-1-ylzirconium dimethyl;
1,3,4,6,7,8-hexahydro-pyrimido[1,2-a]pyrimidinate borane-bis-η$^5$-inden-1-ylzirconium bis-dimethylamide;
1,3,4,6,7,8-hexahydro-pyrimido[1,2-a]pyrimidinate borane-bis-η$^5$-inden-1-ylzirconium 2-methyl-1,3-butadiene;
1,3,4,6,7,8-hexahydro-pyrimido[1,2-a]pyrimidinate borane-bis-η$^5$-inden-1-ylzirconium 2,3-dimethyl-1,3-butadiene;
1,3,4,6,7,8-hexahydro-pyrimido[1,2-a]pyrimidinate borane-bis-η$^5$-inden-1-ylzirconium 2-N,N-dimethylaminobenzyl;
1,3,4,6,7,8-hexahydro-pyrimido[1,2-a]pyrimidinate borane-bis-η$^5$-inden-1-ylzirconium allyl;
1,3,4,6,7,8-hexahydro-pyrimido[1,2-a]pyrimidinate borane-bis-η$^5$-inden-1-ylzirconium η$^4$-1,4-diphenyl-1,3-butadiene;
1,3,4,6,7,8-hexahydro-pyrimido[1,2-a]pyrimidinate borane-bis-η$^5$-inden-1-ylzirconium η$^4$-2,4-hexadiene;
1,3,4,6,7,8-hexahydro-pyrimido[1,2-a]pyrimidinate borane-bis-η$^5$-inden-1-ylzirconium η$^4$-1,4-dinaphthyl-1,3-butadiene;
1,3,4,6,7,8-hexahydro-pyrimido[1,2-a]pyrimidinate borane-bis-η$^5$-inden-1-ylzirconium η$^4$-1-phenyl-1,3-pentadiene;
1,3,4,6,7,8-hexahydro-pyrimido[1,2-a]pyrimidinate borane-bis-η$^5$-inden-1-ylzirconium η$^4$-1,3-pentadiene;
N,N'-diisopropyl-phenyl-amidinate borane-bis-η$^5$-(2-methylinden-1-yl)zirconium dichloride;
N,N'-diisopropyl-phenyl-amidinate borane-bis-η$^5$-(2-methylinden-1-yl)zirconium dimethyl;
N,N'-diisopropyl-phenyl-amidinate borane-bis-η$^5$-(2-methylinden-1-yl)zirconium bis-dimethylamide;
N,N'-diisopropyl-phenyl-amidinate borane-bis-η$^5$-(2-methylinden-1-yl)zirconium 2-methyl-1,3-butadiene;
N,N'-diisopropyl-phenyl-amidinate borane-bis-η$^5$-(2-methylinden-1-yl)zirconium 2,3-dimethyl-1,3-butadiene;
N,N'-diisopropyl-phenyl-amidinate borane-bis-η$^5$-(2-methylinden-1-yl)zirconium 2-N,N-dimethylaminobenzyl;
N,N'-diisopropyl-phenyl-amidinate borane-bis-η$^5$-(2-methylinden-1-yl)zirconium allyl;
N,N'-diisopropyl-phenyl-amidinate borane-bis-η$^5$-(2-methylinden-1-yl)zirconium η$^4$-1,4-diphenyl-1,3-butadiene;
N,N'-diisopropyl-phenyl-amidinate borane-bis-η$^5$-(2-methylinden-1-yl)zirconium η$^4$-2,4-hexadiene;
N,N'-diisopropyl-phenyl-amidinate borane-bis-η$^5$-(2-methylinden-1-yl)zirconium η$^4$-1,4-dinaphthyl-1,3-butadiene;
N,N'-diisopropyl-phenyl-amidinate borane-bis-η$^5$-(2-methylinden-1-yl)zirconium η$^4$-1-phenyl-1,3-pentadiene;
N,N'-diisopropyl-phenyl-amidinate borane-bis-η$^5$-(2-methylinden-1-yl)zirconium η$^4$-1,3-pentadiene;
N,N'-bis-2,6-diisopropylphenyl-phenyl-amidinate borane-bis-η$^5$-(2-methyl-4-phenylinden-1-yl)zirconium dichloride;
N,N'-bis-2,6-diisopropylphenyl-phenyl-amidinate borane-bis-η$^5$-(2-methyl-4-phenylinden-1-yl)zirconium dimethyl;
N,N'-bis-2,6-diisopropylphenyl-phenyl-amidinate borane-bis-η$^5$-(2-methyl-4-phenylinden-1-yl)zirconium bis-dimethylamide;
N,N'-bis-2,6-diisopropylphenyl-phenyl-amidinate borane-bis-η$^5$-(2-methyl-4-phenylinden-1-yl)zirconium 2-methyl-1,3-butadiene;
N,N'-bis-2,6-diisopropylphenyl-phenyl-amidinate borane-bis-η$^5$-(2-methyl-4-phenylinden-1-yl)zirconium 2,3-dimethyl-1,3-butadiene;
N,N'-bis-2,6-diisopropylphenyl-phenyl-amidinate borane-bis-η$^5$-(2-methyl-4-phenylinden-1-yl)zirconium 2-N,N-dimethylaminobenzyl;
N,N'-bis-2,6-diisopropylphenyl-phenyl-amidinate borane-bis-η$^5$-(2-methyl-4-phenylinden-1-yl)zirconium allyl;
N,N'-bis-2,6-diisopropylphenyl-phenyl-amidinate borane-bis-η$^5$-(2-methyl-4-phenylinden-1-yl)zirconium η$^4$-1,4-diphenyl-1,3-butadiene;
N,N'-bis-2,6-diisopropylphenyl-phenyl-amidinate borane-bis-η$^5$-(2-methyl-4-phenylinden-1-yl)zirconium η$^4$-2,4-hexadiene;
N,N'-bis-2,6-diisopropylphenyl-phenyl-amidinate borane-bis-η$^5$-(2-methyl-4-phenylinden-1-yl)zirconium η$^4$-1,4-dinaphthyl-1,3-butadiene
N,N'-bis-2,6-diisopropylphenyl-phenyl-amidinate borane-bis-η$^5$-(2-methyl-4-phenylinden-1-yl)zirconium η$^4$-1-phenyl-1,3-pentadiene;
N,N'-bis-2,6-diisopropylphenyl-phenyl-amidinate borane-bis-η$^5$-(2-methyl-4-phenylinden-1-yl)zirconium η$^4$-1,3-pentadiene;
N,N'-bis-2,6-diisopropylphenyl-3-methyl-1,3-diketimine borane-bis-η$^5$-(2-methyl-4-phenylinden-1-yl)zirconium dichloride;
N,N'-bis-2,6-diisopropylphenyl-3-methyl-1,3-diketimine borane-bis-η$^5$-(2-methyl-4-phenylinden-1-yl)zirconium dimethyl;
N,N'-bis-2,6-diisopropylphenyl-3-methyl-1,3-diketimine borane-bis-η$^5$-(2-methyl-4-phenylinden-1-yl)zirconium bis-dimethylamide;
N,N'-bis-2,6-diisopropylphenyl-3-methyl-1,3-diketimine borane-bis-η$^5$-(2-methyl-4-phenylinden-1-yl)zirconium 2-methyl-1,3-butadiene;
N,N'-bis-2,6-diisopropylphenyl-3-methyl-1,3-diketimine borane-bis-η$^5$-(2-methyl-4-phenylinden-1-yl)zirconium 2,3-dimethyl-1,3-butadiene;
N,N'-bis-2,6-diisopropylphenyl-3-methyl-1,3-diketimine borane-bis-η$^5$-(2-methyl-4-phenylinden-1-yl)zirconium 2-N,N-dimethylaminobenzyl;
N,N'-bis-2,6-diisopropylphenyl-3-methyl-1,3-diketimine borane-bis-η$^5$-(2-methyl-4-phenylinden-1-yl)zirconium allyl;
N,N'-bis-2,6-diisopropylphenyl-3-methyl-1,3-diketimine borane-bis-η$^5$-(2-methyl-4-phenylinden-1-yl)zirconium η$^4$-1,4-diphenyl-1,3-butadiene;
N,N'-bis-2,6-diisopropylphenyl-3-methyl-1,3-diketimine borane-bis-η$^5$-(2-methyl-4-phenylinden-1-yl)zirconium η$^4$-2,4-hexadiene;
N,N'-bis-2,6-diisopropylphenyl-3-methyl-1,3-diketimine borane-bis-η$^5$-(2-methyl-4-phenylinden-1-yl)zirconium η$^4$-1,4-dinaphthyl-1,3-butadiene;
N,N'-bis-2,6-diisopropylphenyl-3-methyl-1,3-diketimine borane-bis-η$^5$-(2-methyl-4-phenylinden-1-yl)zirconium η$^4$-1-phenyl-1,3-pentadiene;
N,N'-bis-2,6-diisopropylphenyl-3-methyl-1,3-diketimine borane-bis-η$^5$-(2-methyl-4-phenylinden-1-yl)zirconium η$^4$-1,3-pentadiene;
bis(N,N'-diisopropyl-phenyl-amidinate)diborane-1,2-bis-η$^5$-(2-methyl-4-phenylinden-1-yl)zirconium dichloride;
bis(N,N'-diisopropyl-phenyl-amidinate)diborane-1,2-bis-η$^5$-(2-methyl-4-phenylinden-1-yl)zirconium dimethyl;
bis(N,N'-diisopropyl-phenyl-amidinate)diborane-1,2-bis-η$^5$-(2-methyl-4-phenylinden-1-yl)zirconium bis-dimethylamide;
bis(N,N'-diisopropyl-phenyl-amidinate)diborane-1,2-bis-η$^5$-(2-methyl-4-phenylinden-1-yl)zirconium 2-methyl-1,3-butadiene;

bis(N,N'-diisopropyl-phenyl-amidinate)diborane-1,2-bis-$\eta^5$-(2-methyl-4-phenylinden-1-yl)zirconium 2,3-dimethyl-1,3-butadiene;
bis(N,N'-diisopropyl-phenyl-amidinate)diborane-1,2-bis-$\eta^5$-(2-methyl-4-phenylinden-1-yl)zirconium 2-N,N-dimethylaminobenzyl;
bis(N,N'-diisopropyl-phenyl-amidinate)diborane-1,2-bis-$\eta^5$-(2-methyl-4-phenylinden-1-yl)zirconium allyl;
bis(N,N'-diisopropyl-phenyl-amidinate)diborane-1,2-bis-$\eta^5$-(2-methyl-4-phenylinden-1-yl)zirconium $\eta^4$-1,4-diphenyl-1,3-butadiene;
bis(N,N'-diisopropyl-phenyl-amidinate)diborane-1,2-bis-$\eta^5$-(2-methyl-4-phenylinden-1-yl)zirconium $\eta^4$-2,4-hexadiene;
bis(N,N'-diisopropyl-phenyl-amidinate)diborane-1,2-bis-$\eta^5$-(2-methyl-4-phenylinden-1-yl)zirconium $\eta^4$-1,4-dinaphthyl-1,3-butadiene;
bis(N,N'-diisopropyl-phenyl-amidinate)diborane-1,2-bis-$\eta^5$-(2-methyl-4-phenylinden-1-yl)zirconium $\eta^4$-1-phenyl-1,3-pentadiene;
bis(N,N'-diisopropyl-phenyl-amidinate)diborane-1,2-bis-$\eta^5$-(2-methyl-4-phenylinden-1-yl)zirconium $\eta^4$-1,3-pentadiene;
bis(N,N'-diisopropyl-3-phenyl-1,3-diketimine)diborane-1,2-bis-$\eta^5$-(2-methyl-4-phenylinden-1-yl)zirconium dichloride;
bis(N,N'-diisopropyl-3-phenyl-1,3-diketimine)diborane-1,2-bis-$\eta^5$-(2-methyl-4-phenylinden-1-yl)zirconium dimethyl;
bis(N,N'-diisopropyl-3-phenyl-1,3-diketimine)diborane-1,2-bis-$\eta^5$-(2-methyl-4-phenylinden-1-yl)zirconium bis-dimethylamide;
bis(N,N'-diisopropyl-3-phenyl-1,3-diketimine)diborane-1,2-bis-$\eta^5$-(2-methyl-4-phenylinden-1-yl)zirconium 2-methyl-1,3-butadiene;
bis(N,N'-diisopropyl-3-phenyl-1,3-diketimine)diborane-1,2-bis-$\eta^5$-(2-methyl-4-phenylinden-1-yl)zirconium 2,3-dimethyl-1,3-butadiene;
bis(N,N'-diisopropyl-3-phenyl-1,3-diketimine)diborane-1,2-bis-$\eta^5$-(2-methyl-4-phenylinden-1-yl)zirconium 2-N,N-dimethylaminobenzyl;
bis(N,N'-diisopropyl-3-phenyl-1,3-diketimine)diborane-1,2-bis-$\eta^5$-(2-methyl-4-phenylinden-1-yl)zirconium allyl;
bis(N,N'-diisopropyl-3-phenyl-1,3-diketimine)diborane-1,2-bis-$\eta^5$-(2-methyl-4-phenylinden-1-yl)zirconium $\eta^4$-1,4-diphenyl-1,3-butadiene;
bis(N,N'-diisopropyl-3-phenyl-1,3-diketimine)diborane-1,2-bis-$\eta^5$-(2-methyl-4-phenylinden-1-yl)zirconium $\eta^4$-2,4-hexadiene;
bis(N,N'-diisopropyl-3-phenyl-1,3-diketimine)diborane-1,2-bis-$\eta^5$-(2-methyl-4-phenylinden-1-yl)zirconium $\eta^4$-1,4-dinaphthyl-1,3-butadiene;
bis(N,N'-diisopropyl-3-phenyl-1,3-diketimine)diborane-1,2-bis-$\eta^5$-(2-methyl-4-phenylinden-1-yl)zirconium $\eta^4$-1-phenyl-1,3-pentadiene;
bis(N,N'-diisopropyl-3-phenyl-1,3-diketimine)diborane-1,2-bis-$\eta^5$-(2-methyl-4-phenylinden-1-yl)zirconium $\eta^4$-1,3-pentadiene;
N,N'-diisopropyl-phenyl-amidinate borane-bis-$\eta^5$-(2-methyl-4-naphthylinden-1-yl)zirconium dichloride;
N,N'-diisopropyl-phenyl-amidinate borane-bis-$\eta^5$-(2-methyl-4-naphthylinden-1-yl)zirconium dimethyl;
N,N'-diisopropyl-phenyl-amidinate borane-bis-$\eta^5$-(2-methyl-4-naphthylinden-1-yl)zirconium bis-dimethylamide;
N,N'-diisopropyl-phenyl-amidinate borane-bis-$\eta^5$-(2-methyl-4-naphthylinden-1-yl)zirconium 2-methyl-1,3-butadiene;
N,N'-diisopropyl-phenyl-amidinate borane-bis-$\eta^5$-(2-methyl-4-naphthylinden-1-yl)zirconium 2,3-dimethyl-1,3-butadiene;
N,N'-diisopropyl-phenyl-amidinate borane-bis-$\eta^5$-(2-methyl-4-naphthylinden-1-yl)zirconium 2-N,N-dimethylaminobenzyl;
N,N'-diisopropyl-phenyl-amidinate borane-bis-$\eta^5$-(2-methyl-4-naphthylinden-1-yl)zirconium allyl;
N,N'-diisopropyl-phenyl-amidinate borane-bis-$\eta^5$-(2-methyl-4-naphthylinden-1-yl)zirconium $\eta^4$-1,4-diphenyl-1,3-butadiene;
N,N'-diisopropyl-phenyl-amidinate borane-bis-$\eta^5$-(2-methyl-4-naphthylinden-1-yl)zirconium $\eta^4$-2,4-hexadiene;
N,N'-diisopropyl-phenyl-amidinate borane-bis-$\eta^5$-(2-methyl-4-naphthylinden-1-yl)zirconium $\eta^4$-1,4-dinaphthyl-1,3-butadiene;
N,N'-diisopropyl-phenyl-amidinate borane-bis-$\eta^5$-(2-methyl-4-naphthylinden-1-yl)zirconium $\eta^4$-1-phenyl-1,3-pentadiene;
N,N'-diisopropyl-phenyl-amidinate borane-bis-$\eta^5$-(2-methyl-4-naphthylinden-1-yl)zirconium $\eta^4$-1,3-pentadiene;
N,N'-diisopropyl-3-phenyl-1,3-diketimine borane-bis-$\eta^5$-(2-methyl-4-naphthylinden-1-yl)zirconium dichloride;
N,N'-diisopropyl-3-phenyl-1,3-diketimine borane-bis-$\eta^5$-(2-methyl-4-naphthylinden-1-yl)zirconium dimethyl;
N,N'-diisopropyl-3-phenyl-1,3-diketimine borane-bis-$\eta^5$-(2-methyl-4-naphthylinden-1-yl)zirconium bis-dimethylamide;
N,N'-diisopropyl-3-phenyl-1,3-diketimine borane-bis-$\eta^5$-(2-methyl-4-naphthylinden-1-yl)zirconium 2-methyl-1,3-butadiene;
N,N'-diisopropyl-3-phenyl-1,3-diketimine borane-bis-$\eta^5$-(2-methyl-4-naphthylinden-1-yl)zirconium 2,3-dimethyl-1,3-butadiene;
N,N'-diisopropyl-3-phenyl-1,3-diketimine borane-bis-$\eta^5$-(2-methyl-4-naphthylinden-1-yl)zirconium 2-N,N-dimethylaminobenzyl;
N,N'-diisopropyl-3-phenyl-1,3-diketimine borane-bis-$\eta^5$-(2-methyl-4-naphthylinden-1-yl)zirconium allyl;
N,N'-diisopropyl-3-phenyl-1,3-diketimine borane-bis-$\eta^5$-(2-methyl-4-naphthylinden-1-yl)zirconium $\eta^4$-1,4-diphenyl-1,3-butadiene;
N,N'-diisopropyl-3-phenyl-1,3-diketimine borane-bis-$\eta^5$-(2-methyl-4-naphthylinden-1-yl)zirconium $\eta^4$-2,4-hexadiene;
N,N'-diisopropyl-3-phenyl-1,3-diketimine borane-bis-$\eta^5$-(2-methyl-4-naphthylinden-1-yl)zirconium $\eta^4$-1,4-dinaphthyl-1,3-butadiene;
N,N'-diisopropyl-3-phenyl-1,3-diketimine borane-bis-$\eta^5$-(2-methyl-4-naphthylinden-1-yl)zirconium $\eta^4$-1-phenyl-1,3-pentadiene;
N,N'-diisopropyl-3-phenyl-1,3-diketimine borane-bis-$\eta^5$-(2-methyl-4-naphthylinden-1-yl)zirconium $\eta^4$-1,3-pentadiene;
bis-2,6-diisopropylphenylamido-bis(N,N'-diisopropyl-phenyl-amidinate)diborane titanium dichloride;
bis-2,6-diisopropylphenylamido-bis(N,N'-diisopropyl-phenyl-amidinate)diborane titanium dimethyl;
bis-2,6-diisopropylphenylamido-bis(N,N'-diisopropyl-phenyl-amidinate)diborane titanium bis-dimethylamide;
bis-2,6-diisopropylphenylamido-bis(N,N'-diisopropyl-phenyl-amidinate)diborane titanium 2-methyl-1,3-butadiene;
bis-2,6-diisopropylphenylamido-bis(N,N'-diisopropyl-phenyl-amidinate)diborane titanium 2,3-dimethyl-1,3-butadiene;

bis-2,6-diisopropylphenylamido-bis(N,N'-diisopropyl-phenyl-amidinate)diborane titanium 2-N,N-dimethylaminobenzyl;

bis-2,6-diisopropylphenylamido-bis(N,N'-diisopropyl-phenyl-amidinate)diborane titanium allyl;

bis-2,6-diisopropylphenylamido-bis(N,N'-diisopropyl-phenyl-amidinate)diborane titanium $\eta^4$-1,4-diphenyl-1,3-butadiene;

bis-2,6-diisopropylphenylamido-bis(N,N'-diisopropyl-phenyl-amidinate)diborane titanium $\eta^4$-2,4-hexadiene;

bis-2,6-diisopropylphenylamido-bis(N,N'-diisopropyl-phenyl-amidinate)diborane titanium $\eta^4$-1,4-dinaphthyl-1,3-butadiene;

bis-2,6-diisopropylphenylamido-bis(N,N'-diisopropyl-phenyl-amidinate)diborane titanium $\eta^4$-1-phenyl-1,3-pentadiene;

bis-2,6-diisopropylphenylamido-bis(N,N'-diisopropyl-phenyl-amidinate)diborane titanium $\eta^4$-1,3-pentadiene;

bis-2,6-diisopropylphenylamido-bis(N,N'-diisopropyl-3-phenyl-1,3-diketimine)diborane titanium dichloride;

bis-2,6-diisopropylphenylamido-bis(N,N'-diisopropyl-3-phenyl-1,3-diketimine)diborane titanium dimethyl;

bis-2,6-diisopropylphenylamido-bis(N,N'-diisopropyl-3-phenyl-1,3-diketimine)diborane titanium bis-dimethylamide;

bis-2,6-diisopropylphenylamido-bis(N,N'-diisopropyl-3-phenyl-1,3-diketimine)diborane titanium 2-methyl-1,3-butadiene;

bis-2,6-diisopropylphenylamido-bis(N,N'-diisopropyl-3-phenyl-1,3-diketimine)diborane titanium 2,3-dimethyl-1,3-butadiene;

bis-2,6-diisopropylphenylamido-bis(N,N'-diisopropyl-3-phenyl-1,3-diketimine)diborane titanium 2-N,N-dimethylaminobenzyl;

bis-2,6-diisopropylphenylamido-bis(N,N'-diisopropyl-3-phenyl-1,3-diketimine)diborane titanium allyl;

bis-2,6-diisopropylphenylamido-bis(N,N'-diisopropyl-3-phenyl-1,3-diketimine)diborane titanium $\eta^4$-1,4-diphenyl-1,3-butadiene;

bis-2,6-diisopropylphenylamido-bis(N,N'-diisopropyl-3-phenyl-1,3-diketimine)diborane titanium $\eta^4$-2,4-hexadiene;

bis-2,6-diisopropylphenylamido-bis(N,N'-diisopropyl-3-phenyl-1,3-diketimine)diborane titanium $\eta^4$-4-dinaphthyl-1,3-butadiene;

bis-2,6-diisopropylphenylamido-bis(N,N'-diisopropyl-3-phenyl-1,3-diketimine)diborane titanium $\eta^4$-1-phenyl-1,3-pentadiene; and bis-2,6-diisopropylphenylamido-bis(N,N'-diisopropyl-3-phenyl-1,3-diketimine)diborane titanium $\eta^4$-1,3-pentadiene.

The skilled artisan will recognize that additional members of the foregoing list, such as those wherein boron is replaced by aluminum are also included within the invention. Moreover, it should also be recognized that the terms $\eta^5$ or $\eta^4$ may not accurately reflect the actual electronic distribution of the molecule under use conditions, and that molecules including lesser numbers of contributing atoms to the electronic delocation are intended to be included within such descriptions as well.

The most highly preferred metal complexes are dimethylamidoborane-bis($\eta^5$-cyclopentadienyl)zirconium dichloride, dimethylamidoboranebis($\eta^5$-inden-1-yl)zirconium dichloride, dimethylamidoborane-bis($\eta^5$-2-methyl-4-phenylinden-1-yl)zirconium dichloride, dimethylamidoborane-bis($\eta^5$-2-ethyl-4-phenylinden-1-yl)zirconium dichloride, dimethylamidoborane-bis($\eta^5$-2-isopropyl-4-phenylinden-1-yl)zirconium dichloride, dimethylamidoborane-bis($\eta^5$-2-methyl-4-bis(3,5-trifluoromethyl)phenylinden-1-yl)zirconium dichloride, dimethylamidoborane-bis($\eta^5$-3-t-butylinden-1-yl)zirconium dichloride, diisopropylamidoborane-bis($\eta^5$-cyclopentadienyl)zirconium dichloride, diisopropylamidoboranebis($\eta^5$-inden-1-yl)zirconium dichloride, diisopropylamidoborane-bis($\eta^5$-2-methyl-4-phenylinden-1-yl)zirconium dichloride, diisopropylamidoborane-bis($\eta^5$-2-ethyl-4-phenylinden-1-yl)zirconium dichloride, diisopropylamidoborane-bis($\eta^5$-2-isopropyl-4-phenylinden-1-yl)zirconium dichloride, diisopropylamidoborane-bis($\eta^5$-2-methyl-4-bis(3,5-trifluoromethyl)phenylinden-1-yl)zirconium dichloride, diisopropylamidoborane-bis($\eta^5$-3-t-butylinden-1-yl)zirconium dichloride, diphenylamidoborane-bis($\eta^5$-cyclopentadienyl)zirconium dichloride, diphenylamidoboranebis($\eta^5$-inden-1-yl)zirconium dichloride, diphenylamidoborane-bis($\eta^5$-2-methyl-4-phenylinden-1-yl)zirconium dichloride, diphenylamidoborane-bis($\eta^5$-2-ethyl-4-phenylinden-1-yl)zirconium dichloride, diphenylamidoborane-bis($\eta^5$-2-isopropyl-4-phenylinden-1-yl)zirconium dichloride, diphenylamidoborane-bis($\eta^5$-2-methyl-4-bis(3,5-trifluoromethyl)phenylinden-1-yl)zirconium dichloride, diphenylamidoborane-bis($\eta^5$-3-t-butylinden-1-yl)zirconium dichloride, dimethylamidoborane-bis($\eta^5$-cyclopentadienyl)zirconium 1,4-diphenyl-1,3-butadiene, dimethylamidoboranebis($\eta^5$-inden-1-yl)zirconium 1,4-diphenyl-1,3-butadiene, dimethylamidoborane-bis($\eta^5$-2-methyl-4-phenylinden-1-yl)zirconium 1,4-diphenyl-1,3-butadiene, dimethylamidoborane-bis($\eta^5$-2-ethyl-4-phenylinden-1-yl)zirconium 1,4-diphenyl-1,3-butadiene, dimethylamidoborane-bis($\eta^5$-2-isopropyl-4-phenylinden-1-yl)zirconium 1,4-diphenyl-1,3-butadiene, dimethylamidoborane-bis ($\eta^5$-2-methyl-4-bis(3,5-trifluoromethyl)phenylinden-1-yl)zirconium 1,4-diphenyl-1,3-butadiene, dimethylamidoborane-bis($\eta^5$-3-t-butylinden-1-yl)zirconium 1,4-diphenyl-1,3-butadiene, diisopropylamidoborane-bis($\eta^5$-cyclopentadienyl)zirconium 1,4-diphenyl-1,3-butadiene, diisopropylamidoboranebis($\eta^5$-inden-1-yl)zirconium 1,4-diphenyl-1,3-butadiene, diisopropylamidoborane-bis($\eta^5$-2-methyl-4-phenylinden-1-yl)zirconium 1,4-diphenyl-1,3-butadiene, diisopropylamidoborane-bis($\eta^5$-2-ethyl-4-phenylinden-1-yl)zirconium 1,4-diphenyl-1,3-butadiene, diisopropylamidoborane-bis($\eta^5$-2-isopropyl-4-phenylinden-1-yl)zirconium 1,4-diphenyl-1,3-butadiene, diisopropylamidoborane-bis($\eta^5$-2-methyl-4-bis(3,5-trifluoromethyl)phenylinden-1-yl)zirconium 1,4-diphenyl-1,3-butadiene, diisopropylamidoborane-bis($\eta^5$-3-t-butylinden-1-yl)zirconium 1,4-diphenyl-1,3-butadiene, diphenylamidoborane-bis($\eta^5$-cyclopentadienyl)zirconium 1,4-diphenyl-1,3-butadiene, diphenylamidoboranebis($\eta^5$-inden-1-yl)zirconium 1,4-diphenyl-1,3-butadiene, diphenylamidoborane-bis($\eta^5$-2-methyl-4-phenylinden-1-yl)zirconium 1,4-diphenyl-1,3-butadiene, diphenylamidoborane-bis($\eta^5$-2-ethyl-4-phenylinden-1-yl)zirconium 1,4-diphenyl-1,3-butadiene, diphenylamidoborane-bis($\eta^5$-2-isopropyl-4-phenylinden-1-yl)zirconium 1,4-diphenyl-1,3-butadiene, diphenylamidoborane-bis($\eta^5$-2-methyl-4-bis(3,5-trifluoromethyl)phenylinden-1-yl)zirconium 1,4-diphenyl-1,3-butadiene, and diphenylamidoborane-bis($\eta^5$-3-t-butylinden-1-yl)zirconium 1,4-diphenyl-1,3-butadiene.

In general the complexes of the current invention can be prepared by first converting the ligands represented in formulas 1a and 2a to a dianionic salt (where $R^4$ is H) via reaction with a metal amide such as sodium bis (trimethylsilyl)amide or lithium bis(trimethylsilyl)amide. The dianionic ligand derivative is then reacted with a metal complex precursor such as $MY^3_4$, $MY^3_3$, or $MY^3_2$ (and the corresponding Lewis base adducts), where $Y^3$ is defined as above. Alternatively, reactions employing the neutral ligand, where $R^4$ is hydrogen, in combination with the metal precursors $M(NR^3_2)_4$ or $MR^3_4$ can be employed. (Preparation of the ligands of formula 2a where $Y^{1'}$ and $Y^{2'}$ are each an $NR^1$ group can be readily accomplished by contacting a diboron tetrahydrocarbyloxide compound of the formula $((R^7O)_2B)_2$, where $R^7$ is C1-10 hydrocarbyl, or two $R^7$ groups together are $C_{2-20}$ dihydrocarbyl, especially bis (catecholato)diboron with an alkali metal $C_{1-4}$ dihydrocarbylamide, especially lithium dimethylamide.) All of the foregoing reactions are conducted in an inert solvent such as a hydrocarbon solvent or an etheral solvent in the temperature range of $-100°$ C. to $150°$ C.

An especially useful metal complex precursor reagent corresponds to the formula 3:

Formula 3

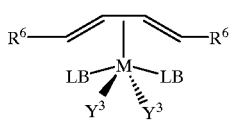

wherein M is zirconium, $R^1$ and LB are as previously defined and $Y^3$ each occurrence is chloride. Employment of this precursor in the reaction with ligands of this invention renders the resulting metal complex in high racemic purity, which is especially useful in the stereospecific polymerization of a-olefins.

Alternatively, where $R^4$ in structures of formula 1a and 2a is a trimethylsilyl group the ligand can be reacted directly with any of the above metal complex precursors of formula 3, employing similar reaction conditions.

The recovery of the desired Group 4 transition metal complex is accomplished by separation of the product from any alkali metal or alkaline earth metal salts and devolatilization of the reaction medium. Extraction into a secondary solvent may be employed if desired. Alternatively, if the desired product is an insoluble precipitate, filtration or other separation techniques may be employed. Final purification, if required, may be accomplished by recrystallization from an inert solvent, employing low temperatures if needed.

The complexes are rendered catalytically active by combination with activating cocatalysts or use of activating techniques that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri (hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. Nos. 5,153,157, 5,064,802, 5,321, 106, 5,721,185, 5,350,723, 5,425,872, 5,625,087, 5,883,204, 5,919,983, 5,783,512, WO 99/15534, and U.S. Ser. No. 09/251,664, filed Feb. 17,1999.

Combinations of neutral Lewis acids, especially the combination of a trialkylaluminum compound having from 1 to 4 carbons in each alkyl group and a halogenated tri (hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

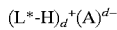

wherein:
L* is a neutral Lewis base;
$(L*-H)^+$ is a conjugate Bronsted acid of L*;

A$^{d-}$ is a noncoordinating, compatible anion having a charge of d−, and d is an integer from 1 to 3.

More preferably A$^{d-}$ corresponds to the formula: [M'Q$_4$]$^-$; wherein:

M' is boron or aluminum in the +3 formal oxidation state; and

Q independently each occurrence is selected from hydride, dialkylamido, halide, hydrocarbyl, hydrocarbyloxide, halo-substituted hydrocarbyl, halo-substituted hydrocarbyloxy, and halo- substituted silyl-hydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, that is, the counter ion has a single negative charge and is A$^-$. Activating cocatalysts comprising boron which are particularly useful in the preparation of catalysts of this invention may be represented by the following general formula:

(L*-H)$^+$(BQ$_4$)$^-$;

wherein:

L* is as previously defined;

B is boron in a formal oxidation state of 3; and

Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl- group of up to 20 nonhydrogen atoms, with the proviso that in not more than one occasion is Q hydrocarbyl.

Preferred Lewis base salts are ammonium salts, more preferably trialkylammonium salts containing one or more C$_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:

trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyltetradecylammonium tetrakis(pentafluorophenyl)borate,
dimethylhexadecylammonium tetrakis(pentafluorophenyl)borate,
dimethyloctadecylammonium tetrakis(pentafluorophenyl)borate,
methylditetradecylammonium tetrakis(pentafluorophenyl)borate,
methylditetradecylammonium (hydroxyphenyl)tris(pentafluorophenyl)borate,
methylditetradecylammonium (diethylaluminoxyphenyl)tris(pentafluorophenyl)borate,
methyldihexadecylammonium tetrakis(pentafluorophenyl)borate,
methyldihexadecylammonium (hydroxyphenyl)tris(pentafluorophenyl)borate,
methyldihexadecylammonium (diethylaluminoxyphenyl)tris(pentafluorophenyl)borate,
methyldioctadecylammonium tetrakis(pentafluorophenyl)borate,
methyldioctadecylammonium (hydroxyphenyl)tris(pentafluorophenyl)borate,
methyldioctadecylammonium (diethylaluminoxyphenyl)tris(pentafluorophenyl)borate,
mixtures of the foregoing,
dialkyl ammonium salts such as:
di-(i-propyl)ammonium tetrakis(pentafluorophenyl)borate,
methyloctadecylammonium tetrakis(pentafluorophenyl)borate,
methyloctadodecylammonium tetrakis(pentafluorophenyl)borate, and
dioctadecylammonium tetrakis(pentafluorophenyl)borate;
tri-substituted phosphonium salts such as:
triphenylphosphonium tetrakis(pentafluorophenyl)borate,
methyldioctadecylphosphonium tetrakis(pentafluorophenyl)borate, and
tri(2,6-dimethylphenyl)phosphonium tetrakis(pentafluorophenyl)borate;
di-substituted oxonium salts such as:
diphenyloxonium tetrakis(pentafluorophenyl)borate,
di(o-tolyl)oxonium tetrakis(pentafluorophenyl)borate, and
di(octadecyl)oxonium tetrakis(pentafluorophenyl)borate;
di-substituted sulfonium salts such as:
di(o-tolyl)sulfonium tetrakis(pentafluorophenyl)borate, and
methylcotadecylsulfonium tetrakis(pentafluorophenyl)borate.

Preferred (L*-H)$^+$ cations are methyldioctadecylammonium and dimethyloctadecylammonium.

Another suitable ion forming, activating cocatalyst comprises a salt of a cationic oxidizing agent and a noncoordinating, compatible anion represented by the formula:

(Ox$^{e+}$)$_d$(A$^{d-}$)$_e$.

wherein:

Ox$^{e+}$ is a cationic oxidizing agent having a charge of e+;

e is an integer from 1 to 3; and

A$^{d-}$ and d are as previously defined.

Examples of cationic oxidizing agents include: ferrocenium, hydrocarbyl-substituted ferrocenium, Ag$^+$, or Pb$^{+2}$. Preferred embodiments of A$^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

©$^+$A$^-$ wherein:

⊙⁺ is a $C_{1-20}$ carbenium ion; and

A⁻ is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

$$R_3Si(X')_q{}^+A^-$$

wherein:

R is $C_{1-10}$ hydrocarbyl, and X', q and A⁻ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., Organometallics, 1994, 13, 2430–2443. The use of the above silylium salts as activating cocatalysts for addition polymerization catalysts is disclosed in U.S. Ser. No. 304,314, filed Sep. 12, 1994, published in equivalent form as WO96/08519 on Mar. 21, 1996, the teachings of which are herein incorporated by reference.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

Another class of suitable catalyst activators are expanded anionic compounds corresponding to the formula:

$$(A^{1+a^1})_b{}^1(Z^1J^1{}_j)^{-c^1}{}_d{}^1,$$

wherein:

$A^1$ is a cation of charge $+a^1$, $Z^1$ is an anion group of from 1 to 50, preferably 1 to 30 atoms, not counting hydrogen atoms, further containing two or more Lewis base sites;

$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1$, $b^1$, $c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

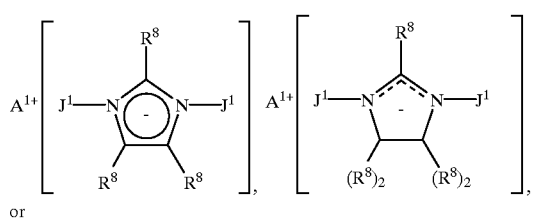

or

-continued

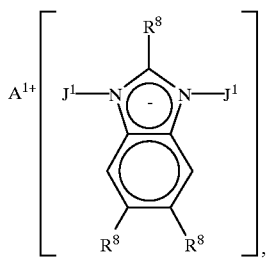

wherein:

$A^{1+}$ is a monovalent cation as previously defined, and preferably is a trihydrocarbyl ammonium cation, containing one or two $C_{10-40}$ alkyl groups, especially the methylbis(tetradecyl)ammonium- or methylbis(octadecyl)ammonium- cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris(pentafluorophenyl)aluminane.

Examples of these catalyst activators include the trihydrocarbylammonium-, especially, methylbis(tetradecyl)ammonium- or methylbis(octadecyl)ammonium- salts of:
bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide,
bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl)imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-2-heptadecylimidazolinide,
bis(tris(pentafluorophenyl)alumane)-4,5-bis(undecyl)imidazolinide,
bis(tris(pentafluorophenyl)alumane)-4,5-bis(heptadecyl)imidazolinide,
bis(tris(pentafluorophenyl)alumane)-5,6-dimethylbenzimidazolide, and bis(tris(pentafluorophenyl)alumane)-5,6-bis(undecyl) benzimidazolide.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, A−. Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium- cations.

During activation of the complexes of the present invention by bulk electrolysis the cation of the supporting electrolyte passes to the counter electrode and A− migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl)borates having from 1 to 10 carbons in each hydrocarbyl or perfluoroaryl group, especially tetra(n-butylammonium)tetrakis(pentafluorophenyl) borate.

A further recently discovered electrochemical technique for generation of activating cocatalysts is the electrolysis of a disilane compound in the presence of a source of a noncoordinating compatible anion. This technique is more fully disclosed and claimed in the previously mentioned U.S. patent application Ser. No. 304,314, published in eqauivalent form as WO96/08519.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any of the foregoing methods, may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres.

Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents use for solution polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings or which are hereby incorporated by reference herein.

Utilizing the present catalysts, (α-olefin homopolymers and copolymers having densities from 0.85 g/cm$^3$ to 0.96 g/cm$^3$, and melt flow rates from 0.001 to 1000.0 dg/min are readily attained in a highly efficient process.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inert inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In an preferred embodiment, a heterogeneous catalyst is prepared by reacting an inorganic compound, preferably a tri($C_{1-4}$ alkyl aluminum compound, with an activating cocatalyst, especially an ammonium salt of a hydroxyaryl(trispentafluorophenyl)borate, such as an ammonium salt of (4-hydroxy-3,5-ditertiarybutylphenyl)tris-(pentafluorophenyl)borate or (4-hydroxyphenyl)-tris(pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably at least a major part of the diluent comprises the α-olefin monomer or monomers to be polymerized.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

The polymerization may be carried out as a batchwise or a continuous polymerization process A continuous process is preferred, in which event catalyst, ethylene, comonomer, and optionally solvent are continuously supplied to the reaction zone and polymer product continuously removed therefrom.

Without limiting in any way the scope of the invention, one means for carrying out such a polymerization process is as follows: In a stirred-tank reactor, the monomers to be polymerized are introduced continuously together with solvent and an optional chain transfer agent. The reactor contains a liquid phase composed substantially of monomers together with any solvent or additional diluent and dissolved polymer. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours. By using a catalyst that incorporates large amounts of hindered monovinyl monomer, hindered monovinyl homopolymer formed from residual quantities of the monomer are substantially reduced Ethylene homopolymers and ethylene/α-olefin copolymers are particularly suited for preparation according to the invention. Generally such polymers have densities from 0.88 to 0.96 g/ml. Typically the molar ratio of α-olefin comonomer to ethylene used in the polymerization may be varied in order to adjust the density of the resulting polymer. When producing materials with a density range of from about 0.91 to about 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than about 0.5, preferably less than 0.2, more preferably less than 0.05, even more preferably less than 0.02 and may even be less than 0.01.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. The term "overnight", if used, refers to a time of approximately 16–18 hours, the term "room temperature", refers to a temperature of about 20–25° C., and the term "mixed alkanes" refers to a commercially obtained mixture of $C_{6-8}$ aliphatic hydrocarbons available under the trade designation Isopar E®, from Exxon Chemicals Inc.

$^1$H (300 MHz) and $^{13}$C NMR (75 MHz) spectra were recorded on a Varian XL-300 spectrometer. $^1$H and $^{13}$C NMR spectra are referenced to the residual solvent peaks and are reported in ppm relative to tetramethylsilane. All J values are given in Hz. Tetrahydrofuran (THF), diethylether, toluene, and hexane were used following passage through double columns charged with activated alumina and a purifying catalyst (Q-5® available from Englehardt Chemicals Inc.) The compounds $BCl_3$—$SMe_2$, $BBr_3$—$SMe_2$, $B(NMe_2)_3$, n-BuLi were all used as purchased from Aldrich. The compound $TiCl_3(THF)_3$ was prepared as described in the literature. All syntheses were performed under dry nitrogen or argon atmospheres using a combination of glove box and high vacuum techniques.

Example 1

Dichloro-[1,2-Bis(2,6-diisopropylanilide)-1,2-bis(dimethylamido)diborane]titanium

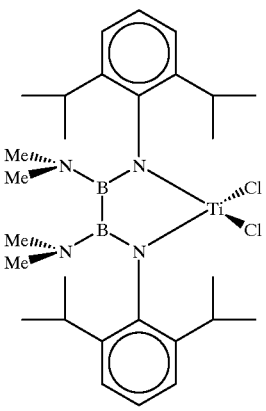

1A) Preparation of Chlorobis(dimethylamido)borane, (modification of Chavant, P. Y.; Vaultier, M. *J. Organomet. Chem.* 1993, 455, 37–46)

$BCl_3$—$SMe_2$ (62.000 g, 345.78 mmol) and $B(NMe_2)_3$ (98.921 g, 691.56 mmole) were stirred together at room temperature overnight under a nitrogen bubbler. The mixture was then heated to reflux for one hour to drive off any residual $SMe_2$. Allowing the pale yellow liquid to stir to room temperature resulted in the isolation of the desired product cleanly (44.979 g, 99.9 percent yield).

$^1$H NMR ($C_6D_6$): δ2.49 (s, 12 H). $^{13}$C NMR ($C_6D_6$): δ39.86.

1B) Preparation of Tetrakis(dimethylamido)diborane (modification of Noth, H; Meister, W. *Z. Naturforsch., Teil B* 1962, 17, 714)

Chlorobis(dimethylamido)borane (30.000 g, 223.19 mmol) was refluxed in hexane (200 ml) as Na/K alloy [Na (1.539 g, 66.96 mmol)/8.726 g K (8.726 g, 223.19 mmol)] was added dropwise to the solution. After the first several drops the reaction initiated as evidenced by a sudden increase in the reflux. The heat was then turned off and the alloy added slowly so as to maintain a reflux. After the addition was complete, the reaction mixture was heated to reflux for an additional hour and then stirred at room temperature for three hours. The mixture was then filtered through a pad of diatomaceous earth and the volatiles removed resulting in the isolation of a yellow liquid. Fractional vacuum distillation resulted in the isolation of the desired compound as a pale yellow liquid (7.756 g, 35.1 percent yield).

$^1$H NMR ($C_6D_6$): δ2.74 (s, 24 H). $^{13}$C NMR ($C_6D_6$): δ41.34.

1C) Preparation of Bis(dimethylamido)diborondichloride (modification of Noth, H; Meister, W. *Z. Naturforsch., Teil B* 1962, 17, 714)

Tetrakis(dimethylamido)diborane (7.76 g, 39.29 mmol) was stirred in diethylether (100 ml) at −78° C. as HCl (157 mmol, 157 ml of 1.0 M solution in diethylether) was added dropwise. This mixture was then allowed to stir for six hours at room temperature. After the reaction period the volatiles were removed and the residue extracted and filtered using hexane. Removal of the hexane resulted in the isolation of a yellow oil. Fractional vacuum distillation resulted in the isolation of the desired compound as a pale yellow liquid (4.72 g, 66.7 percent yield).

¹H NMR (C₆D₆): δ2.40 (s, 6 H), 2.50 (s, 6 H). ¹³C NMR (C₆D₆): δ37.62, 41.78.

1D) Preparation of 2,6-Diisopropylaniline, lithium salt n-BuLi (56.4 mmol, 35.3 ml of 1.60 M solution in hexane) was added dropwise to a solution of 2,6-diisopropylaniline (10.0 g, 56.4 mmol) in hexane (100 ml). This mixture was allowed to stir for 3 hours during which time a white precipitate formed. After the reaction period the mixture was filtered and the white salt washed with hexane and dried under vacuum and used without further purification or analysis (9.99 g, 96.7 percent).

1E) Preparation of 1,2-Bis(2,6-diisopropylanilide)-1,2-bis(dimethylamido)diborane Bis(dimethylamido)diborondichloride (2.35 g, 13.0 mmol) in diethylether (10 ml) was added dropwise to a solution of 2,6-diisopropylaniline, lithium salt (4.77 g, 26.0 mmol) in diethylether (50 ml) at 0° C. This mixture was then allowed to stir overnight at room temperature. After the reaction period the volatiles were removed and the residue extracted and filtered using hexane. Removal of the hexane resulted in the isolation of a the desired product as a white solid (5.32 g, 88.9 percent yield).

¹H NMR (C₆D₆, RT): δ0.9–1.4 (br m, 24 H), 2.3 (s, 6 H), 2.8 (s, 6 H), 3.7 (s, 2 H), 7.0 (br s, 6 H).

1F) Preparation of 1,2-Bis(2,6-diisopropylanilide)-1,2-bis(dimethylamido)diborane, dilithium salt 1,2-Bis(2,6-diisopropylanilide)-1,2-bis(dimethylamido)diborane (1.82 g, 3.95 mmol) was stirred in hexane (75 ml) as n-BuLi (7.91 mmol, 4.94 ml of 1.60 M solution in hexane) was added dropwise. This mixture was then allowed to stir overnight. After the reaction period the mixture was filtered and the salt washed well with hexane and dried under vacuum resulting in the isolation of the desired product as a white powder (1.69 g, 90.4 percent yield).

1G) Preparation of Dichloro-[1,2-Bis(2,6-diisopropylanilide)-1,2-bis(dimethylamido)diborane]titanium 1,2-Bis(2,6-diisopropylanilide)-1,2-bis(dimethylamido)diborane, dilithium salt (0.60 g, 1.27 mmol) in THF (20 ml) was added dropwise to a slurry of TiCl₃(THF)₃ (0.47 g, 1.27 mmol) in THF (50 ml) at 0° C. This mixture was then allowed to stir at room temperature for 45 minutes. PbCl₂ (0.177 g, 0.640 mmol) was then added as a solid and the mixture allowed to stir for an additional 30 minutes. After the reaction period the volatiles were removed and the residue extracted and filtered using hexane. Concentration of the hexane and cooling to −10° C. overnight resulted in the formation of orange X-ray quality crystals (0.156 g, 21.3 percent yield).

¹H NMR (C₆D₆): δ1.23 (d, ³J$_{HH}$=6.6 Hz, 6 H), 1.45 (d, ³J$_{HH}$=6.6 Hz, 6 H), 2.17 (s, 6 H), 2.76 (s, 6 H), 3.53 (septet, ³J$_{HH}$=6.6 Hz, 4 H), 7.11 (s, 6 H)

Example 2

Dichloro [1,2-Bis(2,6-diisopropylanilide)-1,2-bis(dimethylamido)diborane]titanium (alternated preparation)

2A) Preparation of Chlorobis(dimethylamido)borane

BCl₃—SMe₂ (62.000 g, 345.78 mmol) and B(NMe₂)₃ (98.921 g, 691.56 mmol) were stirred together at room temperature overnight under a nitrogen bubbler. The mixture was then heated to reflux for one hour to drive off any residual SMe₂. Allowing the pale yellow liquid to stir to room temperature resulted in the isolation of the desired product (139.436 g, 93.3 percent yield).

¹H NMR (C₆D₆): δ2.49 (s, 12 H). ¹³C NMR (C₆D₆): δ39.86.

2B) Preparation of Tetrakis(dimethylamido)diborane via ClB(NMe)₂

Chlorobis(dimethylamido)borane (30.000 g, 223.19 mmol) was refluxed in hexane (200 ml) as Na/K alloy [Na (1.539 g 66.96 mmol)/8.726 g K (8.726 g, 223.19 mmol)] was added dropwise to the solution. After the first several drops the reaction initiated as evidenced by a sudden increase in the reflux. The heat was then turned off and the alloy added slowly so as to maintain a reflux. After the addition was complete, the reaction mixture was heated to reflux for an additional hour and then stirred at room temperature for three hours. The mixture was then filtered through a diatomaceous earth pad and the volatile components were removed resulting in the isolation of a yellow liquid. Fractional vacuum distillation resulted in the isolation of the desired compound as a pale yellow liquid (7.756 g, 35.1 percent yield).

¹H NMR (C₆D₆): δ2.73 (s, 24 H). ¹³C NMR (C₆D₆): δ41.37.

2C) Preparation of Tetrakis(dimethylamido)diborane via Bis(catecholato)diboron

Lithium dimethylamide (10.70 g, 210.0 mmol) was added slowly as a solid to a solution of bis(catecholato)diboron (10.00 g, 42.00 mmol) in diethylether (200 ml) at −20° C. This mixture was then allowed to stir for an additional 40 hours at room temperature. After the reaction period the ether was removed under vacuum and the residue extracted and filtered using hexane. Removal of the hexane resulted in the isolation of a yellow oil. Fractional vacuum distillation resulted in the isolation of the desired compound as a pale yellow liquid (5.493 g, 66.0 percent yield).

2D) Preparation of Bis(dimethylamido)diborondichloride

Tetrakis(dimethylamido)diborane (7.756 g, 39.19 mmol) was stirred in diethylether (100 ml) at −78° C. as HCl (156.75 mmol, 156.75 ml of 1.0 M solution in diethylether) was added dropwise. This mixture was then allowed to stir for six hours at room temperature. After the reaction period the volatile components were removed and the residue extracted and filtered using hexane. Removal of the hexane resulted in the isolation of a yellow oil. Fractional vacuum distillation resulted in the isolation of the desired compound as a pale yellow liquid (4.722 g, 66.7 percent yield).

¹H NMR (C₆D₆): δ2.40 (s, 6 H), 2.50 (s, 6 H). ¹³C NMR (C₆D₆): δ37.62, 41.78.

2E) Preparation of 2,6-Diisopropylaniline, lithium salt n-BuLi (56.40 mmol, 35.25 ml of 1.6 M solution in hexane) was added dropwise to a solution of 2,6-diisopropylaniline (10.00 g, 56.40 mmol) in hexane (100 ml). This mixture was allowed to stir for 3 hours during which time a white precipitate formed. After the reaction period the mixture was filtered and the white salt washed with hexane and dried under vacuum and used without further purification or analysis (9.988 g, 96.7 percent yield).

2F) Preparation of 1,2-Bis(2,6-diisopropylanilide)-1,2-bis(dimethylamido)diborane Bis(dimethylamido)diborondichloride (2.350 g, 13.00 mmol) in diethylether (10 ml) was added dropwise to a solution of 2,6-diisopropylaniline, lithium salt (4.765 g, 26.01 mmol) in diethylether (50 ml) at 0° C. This mixture was then allowed to stir overnight at room temperature. After the reaction period the volatiles were removed and the residue was extracted and filtered using hexane. Removal of the hexane resulted in the isolation of a the desired product as a white solid (5.322 g, 88.9 percent yield).

¹H NMR (toluene-d₈): δ0.9–1.4 (br m, 24 H), 2.3 (s, 6 H), 2.8 (s, 6 H), 3.7 (s, 2 H), 7.0 (br s, 6 H). ¹³C NMR (toluene-d₈): δ22.51, 24.03 (br), 28.17, 36.82, 42.67, 123.19, 124.78, 140.71, 145.02 (br). MS(EI): m/z 460.4025 (M−H)⁺, calcd. (M−H)⁺ 460.4026.

2G) Preparation of 1,2-Bis(2,6-diisopropylanilide)-1,2-bis(dimethylamido)diborane, dilithium salt 1,2-Bis(2,6-diisopropylanilide)-1,2-bis(dimethylamido) diborane (1.820 g, 3.950 mmol) was stirred in hexane (75 ml) as n-BuLi (7.91 mmol, 4.94 ml of 1.6 M solution in hexane) was added dropwise. This mixture was then allowed to stir overnight. After the reaction period the mixture was filtered and the salt washed well with hexane and dried under vacuum resulting in the isolation of the desired product as a white powder (1.6878 g, 90.4 percent yield).

$^1$H NMR (THF-d$_8$): δ1.04 (d, $^3J_{HH}$=6.9 Hz, 6 H), 1.18 (d, $^3J_{HH}$=6.9 Hz, 6H), 2.45 (s, 12 H), 3.66 (septet, $^3J_{HH}$=6.9 Hz, 4 H), 6.29 (t, $^3J_{HH}$=7.5 Hz, 2 H), 6.73 (d, $^3J_{HH}$=7.5 Hz, 4 H). $^{13}$C NMR (THF-d$_8$): δ24.88, 25.34, 28.00, 40.91, 114.40, 121.95, 137.21, 158.76.

2H) Preparation of Dichloro-[1,2-Bis(2,6-diisopropylanilide)-1,2-bis(dimethylamido)diborane]titanium 1,2-Bis(2,6-diisopropylanilide)-1,2-bis(dimethylamido) diborane, dilithium salt (0.600 g, 1.27 mmol) in THF (20 ml) was added dropwise to a slurry of TiCl$_3$(THF)$_3$ (0.471 g, 1.27 mmol) in THF (50 ml) at 0° C. This mixture was then allowed to stir at room temperature for 45 minutes. PbCl$_2$ (0.177 g, 0.640 mmol) was then added as a solid and the mixture allowed to stir for an additional 30 minutes. After the reaction period the volatile components were removed and the residue was extracted and filtered using hexane. Concentration of the hexane fractions and cooling to −10° C. overnight resulted in the formation of orange X-ray quality crystals (0.156 g, 21.3 percent yield). The ORTEP crystal structure (not necessarily to scale) based on X-ray analysis is found in FIG. 1.

$^1$H NMR (toluene-d$_8$): δ1.23 (d, $^3J_{HH}$=6.6 Hz, 6 H), 1.45 (d, $^3J_{HH}$=6.6 Hz, 6 H), 2.17 (s, 6 H), 2.76 (s, 6 H), 3.53 (septet, $^3J_{HH}$=6.6 Hz, 4 H), 7.11 (s, 6 H). $^{13}$C NMR (toluene-d$_8$): δ24.94, 24.67, 29.48, 39.33, 42.93, 124.08 (br), 17.23, 150.64. MS(EI): m/z 578.2789 (M)⁺, calcd. (M)⁺ 578.2781. Anal. Calcd. For C$_{28}$H$_{46}$B$_2$N$_2$TiCl$_2$: C, 58.07; H, 8.01; N, 9.67. Found: C, 8.28; H, 8.20; N, 9.42.

Example 3

Dimethyl[1,2-Bis(2,6-diisopropylanilide)-1,2-bis(dimethylamido)diborane]titanium Dichloro-[1,2-Bis(2,6-diisopropylanilide)-1,2-bis(dimethylamido)diborane]titanium (Example 2) (0.272 g, 0.470 mmol) was stirred in diethylether (40 ml) as MeMgBr (0.940 mmol, 0.313 ml of 3.0 M solution in diethylether) was added dropwise. This mixture was allowed to stir for one hour. After the reaction period the volatiles were removed and the residue extracted and filtered using hexane. Removal of the hexane resulted in the isolation of the desired product as a dark yellow oil (0.209 g, 82.5 percent yield).

$^1$H NMR (C$_6$D$_6$): δ1.05 (s, 6 H), 1.21 (d, $^3J_{HH}$=6.9 Hz, 16 H), 1.32 (d, $^3J_{HH}$=6.3 Hz, 16 H), 2.19 (s, 6 H), 2.69 (s, 6 H), 3.58 (br, 2 H), 7.0–7.2 (m, 6 H). $^{13}$C NMR (C$_6$D$_6$): δ24.06, 24.83, 29.31, 39.58, 42.93, 57.38, 123.97, 125.18, 139.5 (br), 149.45.

Example 4

Dibenzyl[1,2-Bis(2,6-diisopropylanilide)-1,2-bis(dimethylamido)diborane]zirconium Zirconium tetrachloride (0.100 g, 0.440 mmol) and zirconium tetrabenzyl (0.192 g, 0.440 mmol) were stirred together in diethylether (30 ml) for 1 hour. 1,2-Bis(2,6-diisopropylanilide)-1,2-bis(dimethylamido)diborane, dilithium salt (Example 2G) (0.400 g, 0.842 mmol) in diethylether (30 ml) was then added dropwise and the mixture allowed to stir for 3 hours. After the reaction period the volatiles were removed under vacuum and the residue extracted and filtered using hexane. The filtrate was then concentrated and cooled to −10° C. overnight during which time a white powder precipitated. The mixture was again filtered and the volatile components removed resulting in the isolation of the desired product as a yellow oil (0.123 g, 19.8 percent yield).

$^1$H NMR (toluene-d$_8$): δ1.14 (d, $^3J_{HH}$=6.6 Hz, 6 H), 1.22 (br, 6 H), 1.70 (d, $^3J_{HH}$=9.0 Hz, 2 H), 1.83 (d, $^3J_{HH}$=9.6 Hz, 2 H), 2.10 (s, 6 H) 2.71 (s, 6 H), 3.0–3.2 (br, 2 H), 3.3–3.5 (br, 2 H), 6.59 (d, $^3J_{HH}$=7.2 Hz, 4 H), 6.77 (t, $^3J_{HH}$=7.2 Hz, 2 H), 6.9–7.1 (m, 10 H). $^{13}$C NMR (toluene-d$_8$): δ23.96 (br), 24.22 (br), 24.36 (br), 25.23 (br), 29.47, 39.72, 43.05, 62.23, 122.70, 123.73 (br), 124.08 (br), 124.33, 127.23, 130.82, 139.26 (br), 140.16 (br), 144.90, 144.92, 149.03.

Example 5 rac-diisopropylamidoborane-bis-η$^5$-(2-methyl-4-phenylinden-1-yl)zirconium η$^4$-1,4-diphenyl-1,3-butadiene

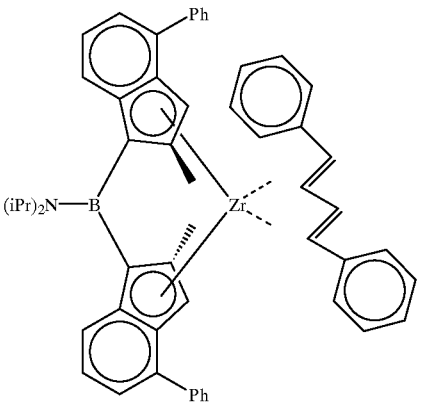

5A) Preparation of Diisopropylaminoboron dichloride

To a methylene chloride solution of trichloroborane (1.0 M, 100 ml, 0.10 mole) was added dropwise at −78° C. diisopropylamine (13.108 ml, 0.100 mole) over a 30 minute period. The solution was allowed to stir for 1 hour, during which a white precipitate formed. The mixture was allowed to warm to room temperature, and solvent was removed under reduced pressure. The residue was dissolved in 100 ml of dry toluene, triethylamine (13.94 ml, 0.10 mole) was added and the solution was stirred overnight at room temperature. The mixture was filtered, the residue was washed with 20 ml of toluene. Solvent was removed under reduced pressure from the combined filtrates, and the resulting oil was purified by vacuum distillation (25–28° C., 13 Pa, 0.1 mm) to give 9.2 g (51 percent) of product as a colorless liquid.

$^1$H NMR (C$_6$D$_6$): δ0.95 (d, 12 H), 3.63 (broad multiplet, 2 H).

5B) Preparation of N,N-diisopropylamino bis(2-methyl-4-phenylindenyl)borane

To 25 ml THF solution of N,N-diisopropylaminoboron dichloride (0.858 g, 4.72 mmole) at room temperature was added drop wise lithium (2-methyl-4-phenyl)indenide (2.00 g, 9.44 mmole in 20 ml THF). The mixture was stirred for 24 hours. Solvent was removed under reduced pressure. The residue was extracted with toluene (2×50 ml), filtered through a medium frit, and solvent was removed under reduced pressure to give a light yellow solid (2.4 g, 97 percent).

Figure 2:
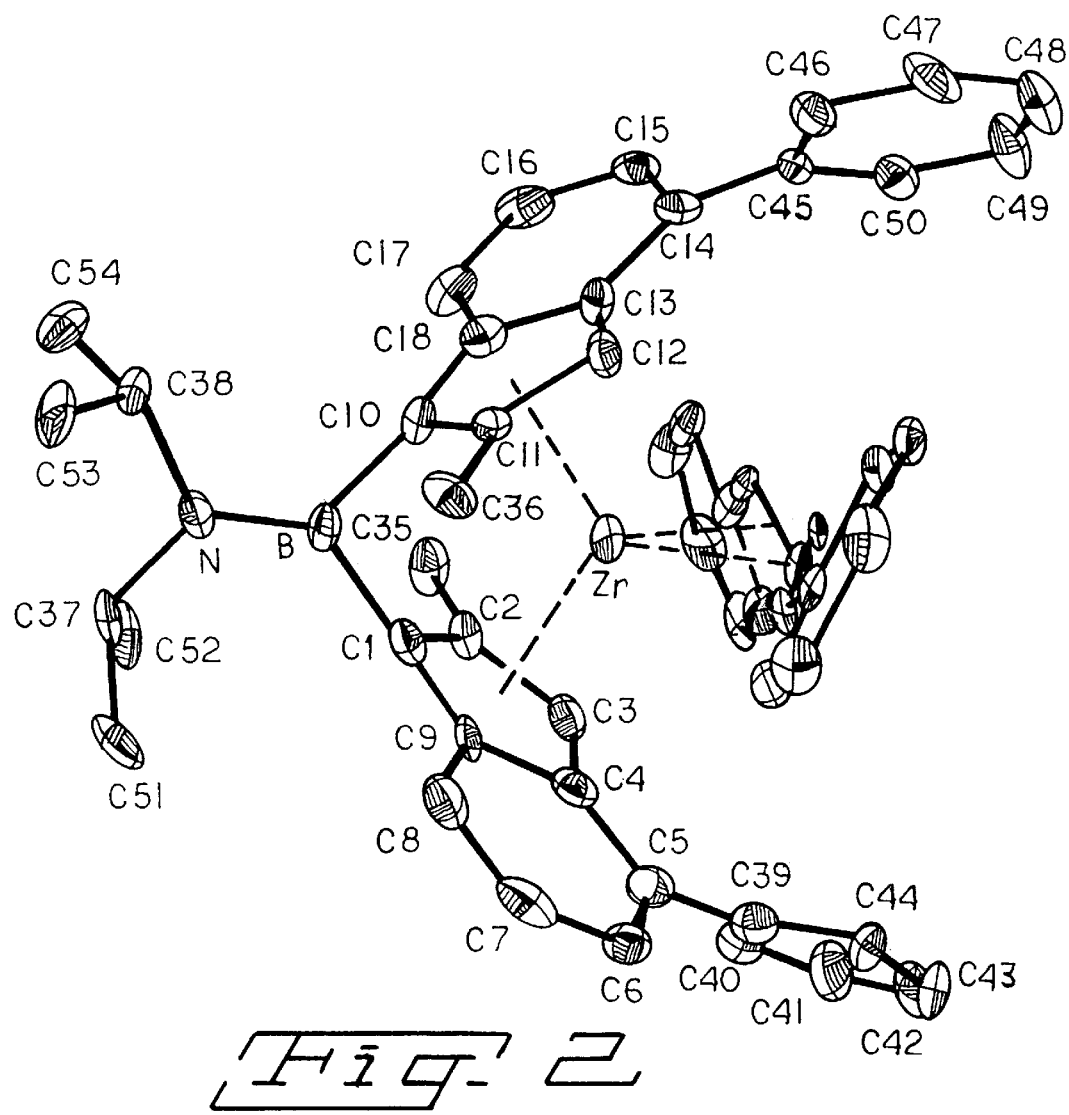

5C) Preparation of rac-diisopropylaminoborane-bis-$\eta^5$-(2-methyl-4-phenylindenyl)zirconium $\eta^4$-diphenyl-1,3-butadiene N,N-diisopropylamino bis(2-methyl-4-phenylindenyl) borane (1.20 g, 2.3 mole) was dissolved in 40 ml of toluene, 2.1 equivalents of potassium is(trimethylsilyl)amide (0.964 g, 4.8 mmole ) was added and the resulting mixture as stirred at room temperature for 24 hours. Volatile components were removed under reduced pressure, and the resulting orange solid washed with 10 ml of hexane, filtered and pumped dry. The dipotassium salt residue (1.3 g, 95 percent, 2.18 mmole) was redissolved in 25 ml of toluene. (1,4-diphenyl-1,3-butadiene)-bis(triethylphosphine)zirconium dichloride (1.318 g, 2.18 mmole) was added and the solution stirred for 12 h at room temperature. The product mixture was filtered through diatomaceous earth filter aid and the solvent of the filtrate was removed under reduced pressure. Further purification was carried out by recrystallization from hexane to yield 0.85 g (48 percent) of the desired product as a dark red solid. The ORTEP crystal structure (not necessarily to scale) based on X-ray analysis is found in FIG. 2.

$^1$H NMR ($C_6D_6$): $\delta$7.6(d, 2H); 7.42–7.00, (m, 18 H); 6.9 (d, 2H); 6.82 (d, 4H); 5.57 (s, 2H); 4.03, m, 2H); 3.45–3.57 (dd, 2H); 1.8(s,6H); 1.28–1.33 (m, 12H).

Example 6

Preparation of diisopropylamidoboranebis-(cyclopentadienyl)zirconium dichloride

6A) Diisopropylamidoboron dichloride

To a solution of $BCl_3$ (17 g, 145 mmol) in $CH_2Cl_2$ (25 ml) at –78° C. was slowly added diisopropylamine (18.49 ml, 132 mmol). A white precipitate formed during addition. The mixture was warmed to room temperature to give a colorless solution. Solvent was removed under high vacuum at room temperature, the residue was then dissolved in benzene (45 ml). Triethylamine (18.8 ml, 134.6 mmol) was added to the solution at room temperature, the mixture was then stirred overnight at room temperature, then filtered to give a red solution. Vacuum distillation (27–28° C., 4 Pa) gave the product (15 g, 57 percent) as a colorless liquid:

$^1$H NMR (500 MHz, $CDCl_3$) d 1.26 (d, 12H, J=5.8 Hz), 3.95 (br, 2H, NCH) $^{13}$C NMR (100 MHz, $CDCl_3$) d 22.1, 49.2 (br). $^{11}$B NMR (115 MHz, $CDCl_3$) 29.4. MS (EI, m/e (intensity)): 181 (M+, 5), 166 (43), 124 (61), 43 (100)

6B) Diisopropylamidobis(cyclopentadienyl)borane

To a solution of the above product (0.39 g, 2.1 mmol) in THF (5 ml) at –78° C. was added dropwise a solution of lithium cyclopentadienide (0.31 g, 2.1 mmol) in THF (10 ml) at –78° C. The mixture was slowly warmed to room temperature and stirred overnight at room temperature to give a red solution. After solvent removal, the residue was extracted with pentane (3x), filtered, pentane was then removed to give the product (0.55 g, 100 percent) as an yellow syrup.

$^{13}$B NMR (115 MHz, C6D,) d 39.8 (major), 30.4 (minor). MS (EI, m/e (intensity)): 241 (M+, 47), 226 (40), 176 (16), 93 (100)

GC-MS was also recorded on the reaction mixture shortly after mixing the two reagents at –78° C., from which only cyclopentadienyldiisopropylboron chloride was detected: MS (EI, m/e (intensity)): 211 (M+, 24), 196 (100), 154 (22).

6C) Dilithium diisopropylamidoboryldicyclopentadienide

To a solution of the above product (0.61 g, 2.53 mmol) in THF (7 ml) at –78° C. was added lithium diisopropylamide (5.57 mmol, prepared in situ from diisopropylamine (0.780 ml, 5.57 mmol) and BuLi (2.50 M, 2.23 ml, 5.57 mmol). The mixture was warmed to room temperature and stirred for 2 hr. Solvent was then removed, residue was washed with pentane to give the product (0.58 g, 91 percent) as a white solid:

$^1$H NMR (360 MHz, THF-$d_8$) d 1.24 (d, 12H, J=6.8 Hz, NCHCH$_3$), 4.54 (m, 2H, NCH), 5.74 (t, 4H, J=2.4 Hz), 5.83 (t, 4H, J=2.4 Hz)

$^{13}$C NMR (100 MHz, THF-$d_8$) d 23.9 (NCHCH$_3$), 25.9 (NCHCH$_3$), 49.3 (NCH), 104.4, 111.9

$^1$B NMR (115 MHz, THF-$d_8$) d 44.6

6D) Diisopropylamidoboranebis(cyclopentadienyl) zirconium dichloride

To a solution of diisopropylamidobis(cyclopentadienyl) borane (0.71 g, 2.95 mmol) in $Et_2O$ (15 ml) at –78° C. was added lithium diisopropylamide (6.93 mmol). The mixture was stirred for 2 hr at room temperature to give a slightly turbid solution. The solution was then added to a suspension of $ZrCl_4$ (0.69 g, 2.95 mmol) in $Et_2O$ (15 ml) at –78° C. The resulting mixture was stirred overnight at room temperature to give an yellowish suspension. Solvent was partially removed and the residue concentrated and cooled to –78° C. to give the product (0.50 g, 38 percent) as colorless crystals.

$^1$H NMR (400 MHz, $CDCl_3$) d 1.32 (d, 12H, J=7.0 Hz), 2.92 (m, 2H), 5.65 (t, 4H, J=2.4 Hz), 6.80 (t, 4H, J=2.4 Hz). $^{13}$C NMR (100 MHz, $CDCl_3$) d 24.6, 49.6, 111.4, 125.7. $^{11}$B NMR (115 MHz, $CDCl_3$) 5 37.6. HRMS (EI), calculated for $C_{16}H_{22}BNC_{12}Zr$: 399.0269, found: 399.0272.

Example 7

Preparation of meso-diisopropylamidoboranebis (inden-1-yl)zirconium dichloride

7A) Diisopropylamidobis(inden-1-yl)borane

To a solution of diisopropylamidoboron dichloride (Example 3, step A)) (1.10 g, 6.0 mmol) in THF (10 ml) at –78° C. was added dropwise a solution of lithium indenide (1.50 g, 12.3 mmol) in THF (40 ml) at –78° C. The mixture was slowly warmed to room temperature and stirred overnight at room temperature to give a red solution. After solvent removal, the residue was extracted with $CH_2Cl_2$ (3x), filtered and the solvent removed to give the desired product (2.12 g, 100 percent) as a white solid:

$^{11}$B NMR (115 MHz, $C_6D$,) d 41.4. MS (EI, m/e (intensity)): 341 (M+, 8), 226 (100). HRMS (EI), calculated for $C_{24}H_{28}BN$ $C_{24}H_{28}BN$: 341.2315, found: 341.2310

7B) Meso-Diisopropylamidoboranebis(inden-1-yl) zirconium dichloride

To a suspension of the above product (0.39 g, 1.41 mmol) in $Et_2O$ (10 ml) at –78° C. was added lithium diisopropy-lamide (in situ prepared from $iPr_2NH$ (2.62 mmol) and BuLi (2.50 M, 2.62 mmol). The mixture was stirred over night at room temperature to give an orange suspension. Solvent was removed and the residue extracted with toluene, and filtered. Toluene was then removed to give an orange solid composed of a mixture of the two stereoisomers (rac/meso, about 6:4). Repeated recrystallization (3x) from toluene at –78° C. gave the pure meso isomer (0.08 g, 14 percent) as an orange solid. M.p.=250–254° C. (dec.).

$^1$HNMR (500 MHz, $CDCl_3$) 1.54(d, 6H, J=6.6 Hz), 1.57 (d, 6H, J=6.8 Hz), 4.27 (m, 2H, NCH), 5.91 (d, 2H, J3.0 Hz), 6.9 (m, 4H), 7.17 (t, 2H, J=7.6 Hz), 7.31 (dd, 2H, J=8.3, 3.6 Hz), 7.53 (d, 2H, J=8.6 Hz). $^{13}$C NMR (75 MHz, $CDCl_3$) d 24.7, 25.0 (NCHCH$_3$), 49.7, 100.2 (BC), 115.7, 117.2, 125.2, 125.3, 125.6, 125.9, 126.5, 131.4. $^{11}$B NMR (115

MHz, CDCl$_3$) 8 39.5. HRMS (EI), calculated for C$_{24}$H$_{26}$BNCl$_2$Zr: 499.0582, found, 499.0606. MS (EI, m/e (intensity)): 501 (M+, 20), 458 (7), 341 (18), 226 (93), 143 (80), 115 (99)

Example 8

Preparation of rac-diisopropylamidoboranebis (inden-1-yl)zirconium bis(dimethylamide)

To a mixture of diisopropylamidobis(inden-1-yl)borane (Example 4, step A)) (1.01 g, 2.96 mmol) and Zr(NMe$_2$)$_4$ (0.79 g, 0.96 mmol) was added toluene (15 ml). The resulting solution was heated to 65° C. and stirred for 2 hr to give a bright red solution. The product consisted of two isomers with a ratio of 6.7:1. The solution was filtered, concentrated, and cooled to −78° C. to give the pure rac isomer (0.50 g, 33 percent) as red crystals. The structure was confirmed by X-ray diffraction analysis on single crystals grown from toluene/hexane at −20° C. M.p.=220° C. (dec.).

$^1$H NMR (500 MHz, C$_6$D$_6$) d 1.20 (d, 6H, J=6.8 Hz), 1.27 (d, 6H, J=6.6 Hz), 2.61 (s, 12H), 3.86 (in, 2H), 6.04 (d, 2H, J=2.9 Hz), 6.74 (m, 4H), 7.00 (t, 2H, J=7.6 Hz), 7.3 7 (dd, 2H, J=8.5, 0.9 Hz), 7.52 (d, 2H, J=8.5 Hz). $^{13}$C NMR (90 MHz, C$_6$D$_6$) 5 24.6, 24.9, 47.9 (NCH$_3$), 49.6, 105.6, 112.4, 123.1, 123.2, 124.0, 124.2, 126.3, 129.1. $^{11}$B NMR (115 MHz, C$_6$D$_6$) d 40.8. HRMS (EI), calculated for C$_{28}$H$_{38}$BN$_3$Zr: 517.2206, found, 517.2217. MS (EI, m/e (intensity)): 517 (M+, 20), 471 (45), 429 (100), 330 (24), 226 (70)

Example 9

Rac-Diisopropylamidoboranebis(inden-1-yl) zirconium dichloride

To a solution of rac-diisopropylamidoboranebis(inden-1-yl)zirconium bis(dimethylamide) (0.50 g, 0.96 mmol) in toluene (35 ml) at room temperature was added trimethyhl-silyl chloride (2.0 ml, 15.76 mmol). The solution was stirred for 8 h at room temperature to give an orange suspension. Solvent was removed, residue was washed with pentane (2×) to give the desired product (0.40 g, 83 percent) as an orange powder. Single crystals suitable for X-ray structural analysis were grown from mixed solvents of CH$_2$Cl$_2$ and hexane at −20° C. M.p.=242° C. (dec.).

$^1$H NMR (500 MHz, CDCl$_3$) d 1.50 (d, 6H, J=6.8 Hz), 1.55 (d, 6H, J=6.6 Hz), 4.24 (heptet, 2H, J=7.7 Hz), 5.79 (d, 2H, J=3.0 Hz), 6.80 (dd, 2H, J=3.2, 0.7 Hz), 7.07 (t, 2H, J=7.6 Hz), 7.28 (dd, 2H, J=7.0, 0.7 Hz), 7.3 8 (t, 2H, J=8.0 Hz), 7.58 9d, 2H, J=8.8 Hz). $^{13}$C NMR (75 MHz, CDCl$_3$) d 24.7, 25.0, 49.6, 98.4 (BC), 113.1, 114.1, 122.0, 123.0, 125.8, 126.4, 127.2, 131.9. $^{11}$B NMR (115 MHz, CDCl$_3$) d 39.2. HRMS (EI), calculated for C$_{24}$H$_{26}$BNCl$_2$Zr: 499.0582, found, 499.0606. MS (EI, m/e (intensity)): 501 (M+, 20), 458 (7), 341 (18), 226 (93), 143 (80), 115 (99). Anal. Calculated for C$_{24}$H$_{26}$BNCl$_2$Zr: C, 57.48; H, 5.19; N, 2.79. Found: C, 57.46; H, 5.32; N, 2.68.

Example 10

Preparation of rac-(diisopropylamidoborane)bis (tetrahydroinden-1-yl)zirconium dichloride A solution of diisopropylamidoboranebis(inden-1-yl) zirconium dichloride (Example 6) (0.16 g, 0.32 mmol) in CH$_2$Cl$_2$ (7 ml) was added to an autoclave reactor containing PtO$_2$ (0.0105 g). The mixture was flushed four times with H$_2$ (200 psi, 1.4 MPa), then charged with H$_2$ (1500 psi, 10.4 MPa) and stirred for 15 h at room temperature to give a greenish suspension. CH$_2$Cl$_2$ (25 ml) was added the mixture which was then filtered. Solvent was removed under reduced pressure and the residue was washed with pentane (2×) to give diisopropylamidoboranebis(tetrahydro-inden-1-yl) zirconium dichloride (0.15 g, 92 percent) as a slightly greenish solid.

$^1$H NMR (400 MHz, C$_6$D$_6$) d 1.06 (d, 12H, J=6.6 Hz), 1.33 (m, 2H), 1.47 (m, 2H), 1.92 (m, 4H), 2.05 (t, 1H, J=4.8 Hz), 2.09 (d, 1H, J=5.0 Hz), 2.34 (m, 2h), 2.53 (t, 1H, J=5.3 Hz), 2.56 (t, 1H, J=5.0 Hz), 3.20 (m, 2H), 3.60 (hept, 2H, J=6.6 Hz), 5.01 (d, 2H, J=2.9 Hz), 6.53 (d, 2H, J=2.6 Hz). $^{13}$C NMR (100 MHz, C$_6$D$_6$) d 23.0, 23.6, 24.4, 24.7, 24.8, 27.0, 49.6, 109.7, 121.6, 124.2, 136.1. $^{11}$B NMR (115 MHz, C$_6$D$_6$) d 39.2 ppm. HRMS (EI) Calculated for C$_{24}$H$_{34}$$^{11}$BNCl$_2$Zr 507.1208, found 507.1198

Example 11

Preparation of rac-N,N-diisopropylamidoborane-bis-η$^5$-(2-methyl-4-naphthyl indenyl) zirconium η$^4$-1,4-diphenyl-1,3-butadiene

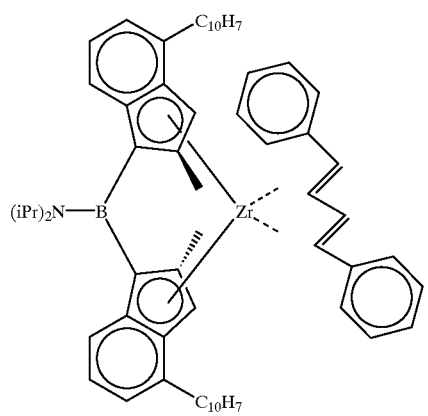

11A) Preparation of potassium (2-methyl-4-naphthyl) indenide

2-Methyl-4-naphthylindene (1.00 g, 3.27 mmole) was dissolved in 20 ml of toluene, potassium bis(trimethylsilyl) amide (1.05 equivalent, 3.43 mmole, 0.684 g) was added and the reaction mixture was stirred at room temperature for 24 hours, during which a yellow solid precipitated. Hexane was added (20 ml) and the mixture was stirred for 2 h. The solid product was isolated by vacuum filtration through a medium porosity frit. The solid was pumped dry giving 1.10 g, 98 percent of the desired product.

11B) Preparation of N,N-diisopropylamino bis(2-methyl-4-naphthylindenyl)borane

To a solution of N,N-diisopropylaminoboron dichloride (0.309 g, 1.70 mmole) in 25 ml of THF at room temperature was slowly added dropwise a 10 ml THF solution of potassium (2-methyl-4-naphthyl)indenide (1.00 g, 3.40 mmole). The mixture was stirred for 24 hours at room temperature, solvent was removed, and the residue was extracted with toluene (2×25 ml). The combined extracts were filtered through a medium frit, and solvent was removed under reduced pressure to give a light yellow solid (1.0 g, 95 percent).

11C) Preparation of rac-N,N-diisopropylaminoborane-bis-η⁵-(2-methyl-4-naphthylindenyl)zirconium η⁴-1,4-diphenyl-1,3-butadiene N,N-diisopropylamino bis(2-methyl-4-naphthylindenyl)borane (0.860 g, 1.38 mmole) was dissolved in 20 ml of toluene, 2.05 equivalents of potassium bis(trimethylsilyl)amide (0.566 g, 2.84 mmole) was added and the reaction mixture was stirred at room temperature for 24 hours. Volatile components were removed under reduced pressure, and the residue was redissolved in 25 ml of toluene. While stirring at room temperature, (1,4-diphenyl-1,3-butadiene)bis(triethylphosphine)-zirconium dichloride (0.835 g, 1.38 mmol) was added and the solution was stirred for 12 h at room temperature. The product mixture was filtered through diatomaceous earth filter aid and the solvent of the filtrate was removed under reduced pressure. Further purification was carried out by recrystallization from hexane to yield 0.27 g (21 percent) of the desired product as a dark red solid.

¹H NMR ($C_6D_6$): δ7.75–7.00, (mm, 30 H); 4.82 (s, 2H); 3.85–3.95(m, 2H); 3.62–3.70 (dd, 2H); 1.82–1.9 (dd, 2H) 1.6 (s, 6H); 1.10–1.33 (m, 12H).

Example 12 rac-1,2-bis(dimethylamidodiborane)bis(2-methyl-4-phenylinden-1-yl)zirconium η⁴-1,4-diphenyl-1,3-butadiene

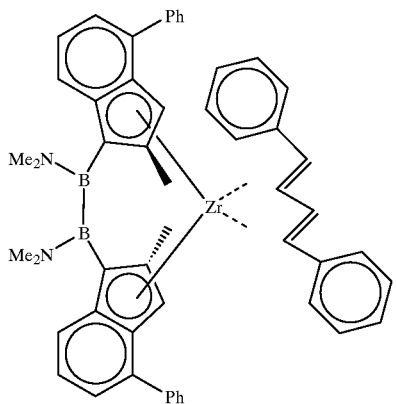

12A) Preparation of 1,2-Bis(2-methyl-4-phenylinden-1-yl)-1,2-bis(dimethylamido)diborane Bis(dimethylamido)diborondichloride (0.500 g, 2.77 mmol) in diethylether (10 ml) was added dropwise to a solution of 2-methyl-4-phenylinden, lithium salt (1.407 g, 11.07 mmol) in diethylether (50 ml) at 0° C. This mixture was stirred overnight at room temperature and the volatiles were removed. The residue was extracted using $CH_2Cl_2$. Filtration and removal of the $CH_2Cl_2$ resulted in the isolation of a the desired product as a pale yellow solid (0.902 g, 62.6 percent yield).

12B) Preparation of 1,2-Bis(dimethylamido)-1,2-bis(2-methyl-4-phenylinden)diborane, dipotassium salt 1,2-Bis(dimethylamido)-1,2-bis(2-methyl-4-phenylinden)diborane (0.791 g, 1.52 mmol) and $KN(TMS)_2$ (0.607 g, 3.04 mmol) were stirred together in toluene (50 ml) overnight. The reaction mixture was then refluxed for one hour, cooled to room temperature, and dried under vacuum. The residue was then slurried in hexane and filtered and the gold microcrystalline solid dried under vacuum (0.881 g, 97.1 percent yield).

12B) Preparation of rac-[1,2-Bis(dimethylamido)-1,2-bis(2-methyl-4-phenylinden)diborane]zirconium(trans, trans-1,4-diphenyl-1,3-butadiene)

1,2-Bis(dimethylamido)-1,2-bis(2-methyl-4-phenylinden)-diborane, dipotassiium salt (0.808 g, 1.35 mmol) was added slowly as a solid to a solution of (1,4-diphenylbutadiene)$ZrCl_2(PEt_3)_2$ (0.819 g, 1.35 mmol) in toluene (75 ml). This mixture was allowed to stir overnight. After the reaction period the mixture was filtered and the volatiles removed resulting in the isolation of a deep red residue. The residue was then slurried in cold hexane, filtered, and dried under vacuum resulting in the isolation of the desired product as a dark red microcrystalline solid (0.501 g, 45.3 percent yield).

¹H NMR ($C_6D_6$): δ1.1–1.2 (m, 2 H), 2.02 (s, 6 H), 2.66 (s, 6 H), 2.90 (s, 6 H), 3.3–3.4 (m, 2 H), 5.28 (s, 2 H), 6.82 (d, ³$J_{HH}$=6.6 Hz, 2 H), 6.9–7.3 (m,5 14 H), 7.35 (d, ³$J_{HH}$=8.4 Hz, 2 H). ¹³C NMR ($C_6D_6$): δ15.10, 42.17, 44.36, 86.78, 93.34, 106.54, 119.17, 123.12, 123.39, 123.71, 124.26, 127.88, 128.51, 128.90, 129.34, 135.76, 140.85, 145.80.

Example 13 rac-diisopropylamidoborane-bis-η⁵-(2-methyl-4-phenylinden-1-yl)hafnium η⁴-1,4-diphenyl-1,3-butadiene

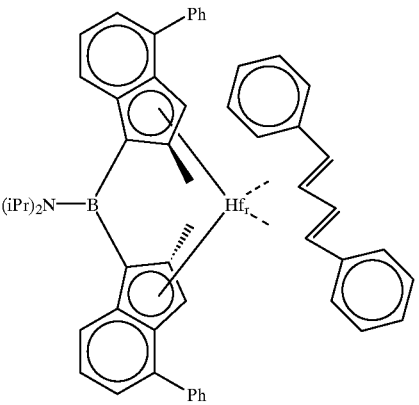

Hafnium tetrachloride (0.375 g, 1.17 mmol) was slurried into 40 ml of toluene. To this slurry were added triethylphosphine (0.346 ml, 2.34 mmol, via syringe), Li powder (Aldrich, low sodium, 0.081 g, 11.7 mmol), and 1,4-diphenyl-1,3-butadiene (0.242 g, 1.17 mmol). The reaction mixture was stirred overnight at room temperature then filtered using a medium porosity frit and diatomaceous earth pad to remove the unreacted Li metal. To the filtrate was added dipotassium diisopropylamidobis(1-(2-methyl-4-phenylindenide))borane, $K_2$[$^i Pr_2$NB(2-Me-4-Ph-indenide)$_2$], (0.700 g, 1.17 mmol) using 10 ml of toluene to aid in the transfer. The reaction mixture was stirred for 1 hour at room temperature. The toluene was removed under reduced pressure and the reaction product was extracted with hexane (twice) and filtered (medium porosity frit with diatomaceous earth pad). Additional product was obtained by extracting the salt byproduct using toluene and refiltering using a medium porosity frit and diatomaceous earth pad.

¹H NMR spectroscopic analysis indicated that the desired rac-$^i Pr_2$NB(2-Me-4-Ph-inden-1-yl)$_2$Hf(1,4-diphenyl-1,3-butadiene) isomer was largely insoluble in hexane and that the undesired meso-isomer could be separated by repeated extraction with hexane. Final isolation and purification of rac-$^i Pr_2$NB(2-Me-4-Ph-inden-1-yl)$_2$Hf(1,4-diphenyl-1,3-butadiene) was accomplished by soxhlet extraction using hexane. After the hexane extract becomes colorless the thimble was removed and dried, yielding 0.042 g of pure rac-$^iPr_2$NB(2-Me-4-Ph-inden-1-yl)$_2$Hf(1,4-diphenyl-1,3-butadiene) as determined by $^1$H and $^{13}$C NMR spectroscopic analysis.

$^1$H NMR (C$_6$D$_6$): δ7.6(d, 2H); 7.42–7.00, (m, 18 H); 6.9 (d, 2H); 6.82 (d, 4H); 5.57 (s, 2H); 4.03, m, 2H); 3.45–3.57 (dd, 2H); 1.8(s,6H); 1.28–1.33 (m, 12H).

Example 14 rac-diisopropylamidoborane-bis-η$^5$-(2-methyl-4-phenylinden-1-yl)zirconium η$^4$-1,4-diphenyl-1,3-butadiene

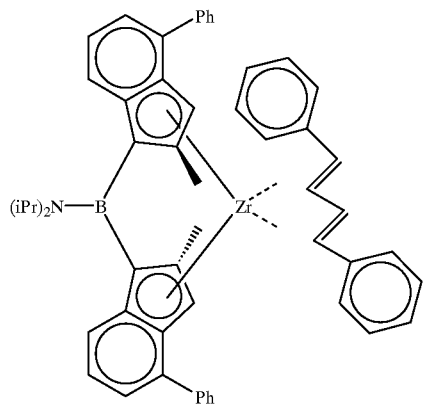

In a glove box, diisopropylamidobis(2-methyl-4-phenylinden-1-yl)borane (0.125 g, 0.240 mmole) was dissolved in 20 ml of dry THF, and 2 equivalents of potassium bis(trimethylsilyl)amide (0.500 molar solution, 0.960 ml, 0.480 mmole) was added dropwise over 10 minute period at room temperature, after which the solution was stirred for 4 hours. Volatile components were removed under reduced pressure and the remaining solids were redissolved in 25 ml of toluene. While stirring at room temperature, (1,4-diphenyl-1,3-butadiene)bis(triethylphosphine)zirconium dichloride (0.145 g, 0.240 mmole) was added and the resulting solution was stirred for 4 hours. The product was recovered by filtering the mixture through diatomaceous earth and removing the solvent of the filtrate under reduced pressure. Further purification was carried out by recrystallization from hexane to yield the product as a dark red solid.

Example 15

Preparation of rac-{$^iPr_2$NC(N$^i$Pr)$_2$}borane-bis-η$^5$-(2-methyl-4-phenylindenyl)zirconium η$^4$-1,4-diphenyl-1,3-butadiene

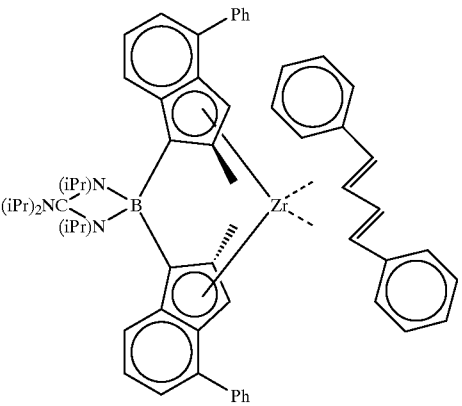

15A) Preparation of $^iPr_2$NC(N$^i$Pr)$_2$}boron dichloride

Diisopropylcarbodiimide (1.178 g, 9.33 mmole) was dissolved in 20 ml of toluene, cooled to 0° C., and solid lithium diisopropylamide (1.00 g, 9.33 mmole) was added slowly to the solution over a 5 minute period. The solution was was allowed to warm to room temperature while stirring for 3 hours. This solution was subsequently added dropwise over a 30 minute period to a 1 molar heptane solution (0° C.) of boron trichloride (9.33 ml, 9.33 mmole) and allowed to warm to room temperature overnight. The solution was filtered, and solvents were removed under reduced pressure to yield 2.3 g (97 percent) of light yellow oil.

$^1$H NMR (C$_6$D$_6$): δ3.6–3.4 (m, 2H); 3.4–3.25 (septet, 2H); 1.43 (d, 12H); 0.8 (d, 12 H).

15B) Preparation of bis(2-methyl-4-phenylindenyl){$^iPr_2$NC(N$^i$Pr)$_2$}borane $^iPr_2$NC(N$^i$Pr)$_2$}boron dichloride (0.30 g, 0.97 mmole) was dissolved in 30 ml of THF, and potassium (2-methyl-4-phenyl)indenide (0.476 g, 1.95 mmole) was added. The mixture was stirred for 24 hours at room temperature, followed by heating at reflux for 4 hours. The product mixture was allowed to cool to room temperature, and solvent was removed under reduced pressure. The residue was extracted with toluene (2×50 ml), filtered through a medium frit, and solvent was removed in vacuo to give a light yellow solid (0.533 g, 85 percent).

15C) Preparation of rac-{$^iPr_2$NC(N$^i$Pr)$_2$}borane-bis-η$^5$-(2-methyl-4-naphthyl indenyl) zirconium η$^4$-1,4-diphenyl-1,3-butadiene Bis(2-methyl-4-phenylindenyl){$^iPr_2$NC(N$^i$Pr)$_2$}borane (0.533 g, 0.82 mmole) was dissolved in 20 ml of toluene, 2.00 equivalents of potassium bis(trimethylsilyl)amide (0.0.328 g, 1.65 mmole) was added and the reaction mixture was stirred at room temperature for 24 hours. Volatile components were removed under reduced pressure, and the residue was washed with 2×25 mL of hexane. Volatile components were removed under reduced pressure to yield 0.382 g (64 percent) of the orange solid dipotassium salt. A portion of this solid (0.100 g, 0.14 mmole) was dissolved in 15 mL of toluene. While stirring at room temperature, (1,4-diphenyl-1,3-butadiene)bis(triethylphosphine) zirconium dichloride (0.084 g, 0.14 mmole) was added and the solution was stirred for 12 h at room temperature. The product mixture was filtered through diatomaceous earth filter aid and the solvent of the filtrate was removed under reduced pressure to give 0.115 g (88 percent) of crude product which existed as a rac/meso mixture. Further purification was carried out by recrystallization from hexanes to yield 0.015g (12 percent) of rac-product as a dark red solid.

$^1$H NMR (C$_6$D$_6$): δ7.6–6.7, (mm, 26 H); 5.55 (s, 2H); 4.05–3.90(m, 2H); 3.5 (dd, 2H); 2.7–2.4 (m, 2H); 1.78 (s, 6H); 1.55 (dd, 2H); 1.25 (m, 12 H); 0.95 (m, 12 H).

Example 16 rac-dimethylamidoborane-bis-η$^5$-(2-methyl-4-phenylinden-1-yl)zirconium η$^4$-1,4-diphenyl-1,3-butadiene

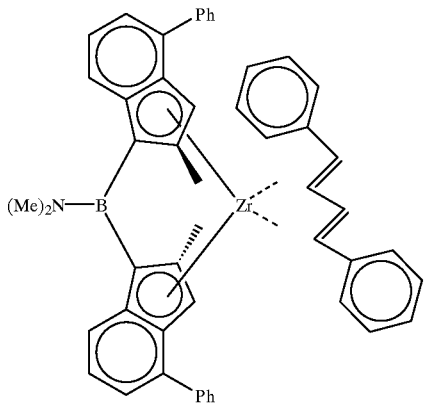

16A) Preparation of Dimethylamidodibromoborane

B(NMe$_2$)$_3$ was added to BBr$_3$ dropwise. The reaction was immediate and exothermic. This mixture was allowed to stir for 2 hours at which time NMR analysis showed the reaction to be essentially quantitative and complete (22.510 g, 99.9 percent yield).

$^1$H NMR (C$_6$D$_6$): δ2.31 (6 H). $^{13}$C NMR (C$_6$D$_6$): δ41.45.

16B) Preparation of Dimethylamido-bis(2-methyl-4-phenylindinyl)borane

A solution of dimethyamidodibromoborane (0.511 g, 2.38 mmol) in toluene (10 ml) was cooled to 0° C. and diethyl-ether (2 equivelents) added. This mixture was then added dropwise to a solution of 2-methyl-4-phenylindene, lithium salt (1.011 g, 4.76 mmol) in THF (50 ml) at 0° C. This mixture was then allowed to stir for overnight at room temperature. After the reaction period the volatile components were removed and the residue extracted and filtered using hexane. Removal of the hexane resulted in the isolation of a yellow oil (1.103 g, 99.9 percent yield).

16C) Preparation of Dimethylamido-bis(2-methyl-4-phenylindenyl)borane, dipotassium salt Dimethylamido-bis(2-methyl-4-phenylindenyl)borane (1.010 g, 2.17 mmol) and KN(TMS)$_2$ (0.866 g, 4.34 mmol) were stirred together in toluene (50 ml) overnight. The reaction mixture was then refluxed for one hour, cooled to room temperature, and dried under vacuum. The residue was then slurried in hexane and filtered and the orange microcrystalline solid dried under vacuum (1.246 g,>100% yield due to residual solvent still present as observed by NMR).

16D) Preparation of rac-[Dimethylamido-bis(2-methyl-4-phenylindene)borane]-zirconium (trans,trans-1,4-diphenyl-1,3-butadiene)

Dimethylamido-bis(2-methyl-4-pheny-lindenyl)borane, dipotassium salt (1.246 g, 2.30 mmol) was added slowly as a solid to a solution of (1,4-diphenylbutadiene)ZrCl$_2$(PEt$_3$)$_2$ (1.391, 2.30 mmol) in toluene (75 ml) and allowed to stir overnight. After the reaction period the mixture was filtered and the volatiles removed resulting in the isolation of a dark residue. This residue was slurried in hexane and filtered. Red crystals grew over a 2-hour period of time from the sitting hexane filtrate (0.222 g). The solid on the frit was washed through the frit using toluene and a second crop of crystals was grown from this mixture by allowing the solution to slowly concentrate over a period of one week by slow evaporation of the toluene (0.100 g). Combining the crystals obtained resulted in the isolation of a total of 0.322 g (18.4 percent yield) of highly pure product.

$^1$H NMR (C$_6$D$_6$): δ1.71 (s, 3 H), 1.7–1.8 (m, 2 H), 2.89 (s, 3 H), 3.4–3.5 (m, 2 H), 5.52 (s, 2 H), 6.76 (d, $^3J_{HH}$=7.2 Hz, 4 H), 6.8–7.4 (m, 12 H), 7.43 (d, $^3J_{HH}$=8.4 Hz, 2 H). $^{13}$C NMR (C$_6$D$_6$): δ15.95, 39.52, 85.43, 90.93, 104.13, 117.32, 12.49, 121.65, 122.3 (br), 123.32, 124.19, 124.32, 127.81, 127.83, 128.68, 128.74, 128.81, 136.06, 140.55, 143.86. MS(EI): m/z 759.2635 (M–H)$^+$, calcd. (M–H)$^+$759.2610.

Example 17 bis(trimethylsilyl)amido(η-fluoren-9-yl)(η-cyclopentadienyl)borane-zirconium dichloride.

17A) Preparation of bistrimethylsilylamido(9-fluorenyl) boron chloride n-Butyllithium (2.5 M hexane, 4.20 ml, 10.50 mmol) was added to a solution of fluorene (1.66 g, 10.00 mmol) in THF (15 ml) at −78° C. The resulting mixture was slowly warmed up and stirred at room temperature for 5 h to give a red solution. The solution was cooled to −78° C. and added dropwise to a solution of bis(trimethylsilyl)amidoboron dichloride (TMS)$_2$NBCl$_2$ (2.42 g, 10.00 mmol) in THF (25 ml) at −78° C. to give a light yellow solution. The solution was stirred overnight at room temperature. Volatile components were removed, and the residue was extracted with pentane and filtered. The pentane was removed to give the desired product (3.70 g, 100 percent yield) as a white solid.

$^1$H NMR (400 MHz, CDCl$_3$): δ0.45 (s, 18H), 4.41 (s, 1H), 7.34 (dt, 2H, J=7.4, 1.1 Hz), 7.42 (t, 2H, J=7.3 Hz), 7.49 (d, 2H, J=7.6 Hz), 7.87 (d, 2H, J=7.4 Hz). $^{13}$C NMR (100 MHz, CDCl$_3$) δ4.6, 121.0, 125.4, 127.2, 127.3, 143.0, 145.9. $^{11}$B NMR (115.5 MHz, CDCl$_3$,) δ46.6.

17B) Preparation of bis(trimethylsilyl)amido(9-fluorenyl)(cyclopentadienyl)borane A solution of CpNa/THF (0.24 g, 2.40 mmol) in THF (15 ml) at −78° C. was added dropwise to a solution of bistrimethylsilyamido(9-fluorenyl)boron chloride (0.89 g, 2.40 mmol) THF (15 ml) at −78° C. The resulting yellow solution was slowly warmed to room temperature with stirring and stirred over night. Volatile components were removed under reduced pressure, and the residue was extracted with pentane and filtered. The pentane solution was concentrated and cooled to −78° C. to give the desired product (0.57 g, 59 percent) as a white solid.

$^1$H NMR (400 MHz,C$_6$D$_6$): δ0.20 (s, 18 H), 1.71 (t, 2H, J=1.4 Hz), 4.33 (s, 1 H), 5.93 (m, 1 H), 6.13 (m, 1 H), 6.69 (dd, 1 H, J=7.4, 1.5 Hz), 7.09 (dt, 2H, J=7.2, 1.5 Hz), 7. 19 (dt, 2 H, J=7.4, 1.7 Hz), 7.46 (dd, 2H, J=7.4, 1.1 Hz), 7.70 (dd, 2H, J=7.6, 0.8 Hz). $^{13}$C NMR (100 MHz, C$_6$D$_6$) δ5.1, 43.4, 120.6, 125.8, 126.7, 127.2, 132.2, 139.5, 142.9, 143.1, 147.4. $^{11}$B NMR (115.5 MHz, C$_6$D$_6$) δ51.6. HRMS (EI) calculated for C$_{23}$H$_{29}$BNSi, (M-CH$_3$), 386.1932; found, 386.1945.

17C)) bis(trimethylsilyl)amidoborane(η-cyclopentadienyl)(η-fluoren-9-yl)zirconium dichloride A solution of lithium diisopropylamide (prepared in situ from iPr$_2$NH (0.54 ml, 3.84 mmol) and BuLi (2.5 M hexane, 1.61 mil, 4.03 mmol)) in THF (10 ml) was added to a solution of bis(trimethylsilyl)amido(9-fluorenyl) (cyclopentadienyl)borane (0.77 g, 1.92 mmol) in THF (10 ml) at −78° C. The resulting mixture was slowly warmed to room temperature and stirred overnight to give a dark red solution. Volatile components were removed to give an orange solid which was then dissolved in toluene (15 ml). The toluene solution was added to a suspension of ZrCl$_4$ (0.40 g, 1.9 mmol) in toluene (8 ml) at −78° C. The mixture was warmed to room temperature and stirred overnight to give a dark red suspension. Volatile components were removed under reduced pressure, and the residue was extracted with toluene and then filtered. The volatile components were removed under reduced pressure, and the residue was washed with pentane (3×) to give the product as red solid.

mp=252–254 (dec.). $^1$H NMR (400 MHz, CDCl$_3$): δ0.26 (s, 9H), 0.50 (s, 9H), 5.44 (t, 2H, J=2.4 Hz), 6.45 (t, 2H, J=2.4 Hz), 7.19 (d, 2H, J=8.4 Hz), 7.31 (t, 2H, J=7.5 Hz), 7.62 (t, 2H, J=7.8 Hz), 8.12 (d, 2H, J=8.4 Hz). $^{13}$C NMR (75 MHz, CDCl$_3$) δ4.8, 5.9, 105.3, 121.4, 122.9, 124.4, 125.4, 125.7, 129.1, 143,0. $^{11}$B NMR (115.5 MHz, CDCl$_3$) δ48.2. HRMS (EI) calculated for C$_{24}$H$_{30}$BNSi$_2$Cl$_2$Zr: 559.0434; found, 559.0443.

Example 18 diisopropylamidoborane(η-cyclopentadienyl)(η-fluoren-9-yl)zirconium dichloride

18A) Preparation of Diisopropylamido(9-fluorenyl)boron chloride

The reaction conditions of Example 17A) were substantially repeated excepting that diisopropylamidodichloroboron was used in place of bis(trimethylsilyl)amido-dichloroboron. At the end of the reaction, solvent was removed, residue was extracted with CH$_2$Cl$_2$ and filtered. Volatile components were removed to give the product (0.91 g, 98 percent) as a yellowish solid.

$^1$H NMR (400 MHz, CDCl$_3$): δ1.36 (br, 6H), 1.79 (br, 6H), 4.41 (br, 1H), 7.35 (t, 2H, J=7.7 Hz), 7.42 (t, 2H, J=7.5 Hz), 7.50 (br, d, 2H, J=4.7 Hz), 7.88 (d, 2H, J=7.3 Hz). $^{13}$C NMR (100 MHz, CDCl$_3$) δ24.5 (br), 43.2 (br), 48.5 (br), 120.2, 124.4, 126.4, 126.9, 141.1 (br), 146.9. $^{11}$B NMR (115.5 MHz, CDCl$_3$) δ37.2. HRMS (EI) Calculated for C$_{19}$H$_{23}$BNCl, 311.1612; found, 311.1613.

18B) Diisopropylamido(cyclopentadienyl)(9-fluorenyl)borane

The reaction conditions of Example 17 B were substantially repeated excepting that diisopropylamido(9-fluorenyl) boron was used in place of bis(trimethylsilyl)amido(9-fluorenyl)boron chloride. Reaction of CpNa/THF (0.96 g, 9.60 mmol) and diisopropylamido(9-fluorenyl)boron chloride (2.98 g, 10.00 mmol) gave a reaction mixture which was extracted with hexane and flittered. Volatiles were removed to give the product (2.11 g, 62 percent) as a yellow solid.

HRMS (EI), Calculated for C$_{24}$H$_{28}$BN, 341.2315, found, 341.2329.

18C) Preparation of diisopropylamidoborane(η-cyclopentadienyl)(η-fluoren-9-yl)zirconium dichloride The reaction conditions of Example 17C) were substantially repeated excepting that diisopropylamido(9-fluorenyl)boron (1,39 g, 4.08 mmol) was used in place of bis (trimethylsilyl)amido(9-fluorenyl)boron. The crude reaction mixture from this reaction was extracted with toluene and filtered. The solution was concentrated, pentane was added and cooled to −78° C. to give the product (0.75 g, 36 percent yield) as a red solid.

mp=280–282° C. $^1$H NMR (500 MHz. C$_6$D$_6$): δ1.01 (d, 6H, J=6.6 Hz), 1.22 (d, 6H, J=6.9 Hz), 3.67 (pent, IH, J=6.6 Hz), 3.80 (pent, 1H, J=6.6 Hz), 5.30 (t, 2H, J=2.4 Hz), 6.38 (t, 2H, J=2.4 Hz), 7.05 (d, 2H, J=8.1 Hz), 7.12 (t, 2H, J=7.5 Hz), 7.46 (t. 2H, J=7.5 Hz), 7.92 (d, 2H, J=8.5 Hz). $^{13}$C NNIR (90 MHz, CDC13) δ24.2, 25.4, 49.1, 49.8, 106.9, 122.2, 123.2, 125.4, 125.8, 129.0, 147.9, 157. 1. $^{11}$B NMR (115.5 MHz, C6D6) δ39.4. EA, calculated for C$_{24}$H$_{28}$BNZrCl$_2$: C, 57.25, H, 5.57, N, 2.78. Found: C, 55.44; H, 5.30; N, 2.62.

Example 19 bis(trimethylsilyl)amidoborane bis(η-inden-1-yl) zirconium bis(dimethylamide)

Bis(trimethylsilyl)amidoboronbis(inden-1-yl) was prepared by reacting lithium indenide (0.50 g, 4.10 mmol) and bis(trimethylsilyl)amidoboron dichloride, (0.48 g, 2.00 mmol) in THF to give the product (0.75 g, 94 percent) as a yellowish solid.

$^1$H NMR (400 MHz, C$_6$D$_6$, major isomer): δ0.32 (s, 18H), 3.64 (s, 2H), 6.08 (dd, 2H, J=5.5, 1.8.Hz), 6.48 (dd, 2H, J=5.2Hz), 6.82 (d., 2H, J=7.3Hz), 0.93 (dt, 2H, J=7.1, 1.2 Hz), 7.20 (m, 4H). $^{11}$B NMR (115.5 MHz, C$_6$D$_6$) δ56.8. HRMS (EI) calculated for C$_{24}$H$_{32}$BNSi$_2$, 401.2166; found, 401.2182. EA, Calculated for C$_{24}$H$_{32}$BNSi$_2$, C, 71.82; H, 7.98; N, 3.49. Found: C, 70.06; H, 8.06; N, 3.36.

The bis(trimethylsilyl)amidoboron bis(inden-1-yl) (0.27 g, 0.67 mmol) and Zr(NMe$_2$)$_4$ (0.18 g, 0.67 mmol) were then combined in toluene (10 ml) 2 hours at 65° C. to give a red solution. Volatile components were removed under reduced pressure to afford the product as a red foam.

$^1$H NMR (400 MHz, C$_6$D$_6$): δ0.26 (s. 18H), 2.53 (s, 12H), 5.95 (d, 2H, J=2.9 Hz), 6.64 (d, 2H, J=2.9 Hz), 6.68 (t, 2H, J=7.5 Hz), 6.95 (t, 2H, J=7.6 Hz), 7.30 (d, 2H, J=8.5 Hz), 7.45 (d, 2H, J=8.8 Hz). $^{13}$C NMR (100 MHz, C$_6$D$_6$) δ5.6, 47.9, 105.1, 111.5, 122.2, 122.9, 124.2, 126.4, 128.5. $^{11}$B NMR (115.5 MHz, C$_6$D$_6$) δ50.3. HRMS (EI) calculated for C$_{28}$H$_{42}$BN$_3$Si$_2$Zr, 577.2057; found, 577.2061.

Example 20

Bis(trimethyl)silylamidobis(η-inden-1-yl) boranezirconium dichloride

Bis(trimethylsilyl)amidoboron bis(inden-1-yl) (0.45 g, 1.12 mmol) and Zr(NMe$_2$)$_4$ (0.30 g, 1.12 mmol) were combined in THF to give an intermediate which was not further purified. Volatile components were removed under reduced pressure and replaced with CH$_2$Cl$_2$ (10 ml). The mixture was stirred with trimethylsilane chloride (1.42 ml, 11.20 mmol) overnight at room temperature. Volatile components were again removed under reduced pressure and the residue was extracted with CH$_2$Cl$_2$ and filtered. The solution was concentrated, layered with pentane, and cooled to −78° C. to give the desired product (0.54 g, 86 percent) as an orange solid.

$^1$H NMR (500 MHz, C$_6$D$_6$): δ0.20 (s, 18H), 5.54 (d, 2H, J=3.3 Hz), 6.68 (dd, 2H, J=2.1, 0.9 Hz), 6.85 (t. 2H, J=7.0 Hz), 7.04 (dd, 2H, J=8.1, 1.1 Hz), 7.17 (m, 2H, overlapped with solvent residue peak), 7.33 (d, 2H, J=8.4 Hz). $^{13}$C NMR (100 MHz, C$_6$D$_6$) δ5.3, 112.8, 113.0, 123.6, 126.5, 127.1, 127.8, 132.1. $^{11}$B NMR (115.5 MHz, C$_6$D$_6$) δ48.5. HRMS (EI) calculated for C$_{24}$H$_{30}$BNSi$_2$Cl$_2$Zr, 559.0434; found, 559.0432.

Example 21

Preparation of rac-diisopropylamidoborane-bis-$\eta^5$-(2-isopropyl-4-phenyl indenyl)zirconium $\eta^4$-1,4-diphenyl-1,3-butadiene

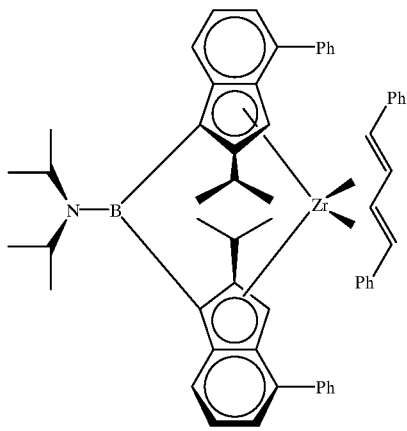

21A) 2-Isopropyl-4-phenyl indene

Sodium hydride (2.1 g, 60 percent dispersion in oil) was placed in 500 ml flask under nitrogen atmosphere. Hexane (about 20 ml) was added to remove the oil, the mixture was stirred briefly. After stirring stopped the NaH was allowed to settle and the the liquids were removed by syringe. This procedure was repeated once more, then THF (200 ml) was added to the NaH and the suspension was cooled with an ice bath. Diethyl isopropylmalonate (10.10 g, 50.00 mmol) in THF (100 ml) was added via an addition funnel over 30 min. After addition of the malonate was complete, the solution was stirred for an additional 40 min. A THF solution (30 ml) of 2-phenylbenzyl bromide (12.5 g, 50.5 mmol) was added via addition funnel and the mixture was stirred overnight. The next morning 100 ml of 1 N ammonium chloride was added. The solution was diluted with ether (200 ml) and the organic layer was washed with brine, dried over $Na_2SO_4$, and stripped of solvent under reduced pressure. The orange red oil was used without further purification.

The crude alkylation product was dissolved in ethanol (300 ml) and water (75 ml). Potassium hydroxide (20 g) was added and the mixture was refluxed overnight. After cooling, ethanol was stripped under reduced pressure. Hexane was added and stirred for 1 hour to dissolve any undesired organic materials. The hexane was decanted and water was added (about 150 ml). The solution was made acidic (to pH 1) by adding concentrated HCl. The desired carboxylic product was extracted with ether, dried over $Na_2SO_4$, and stripped under reduced pressure. NMR spectra of the crude product (10.74 g, 80 percent) indicated that ester hydrolysis and decarboxylation were complete. The crude product, which solidified to a tan solid, was used without further purification.

Thionyl chloride (50 ml) was added to the carboxylic acid and the mixture was stirred overnight at room temperature to dissolve the acid. The excess thionyl chloride was removed under reduced pressure and the remaining acid chloride was dissolved in methylene chloride (75 ml). This solution was added dropwise via an addition funnel to a suspension of aluminum chloride (5.70 g, 42.5 mmol) in methylene chloride (25 ml) and cooled with an ice bath. The reaction was allowed to warm slowly to room temperature and stirred overnight. The solution was poured onto ice (about 100 ml) and stirred vigorously for 1 hour. The organic layer was separated, the aqueous layer was washed once with ether and the combined organic layers were washed with brine, dried over $Na_2SO_4$, and stripped under reduced pressure. The crude 2-isopropyl-4-phenylindanone (10.0 g) as an orange-brown oil was used without further purification.

2-Isopropyl-4-phenylindanone (12.1 g, 48 mmol) was stirred in a mixture of THF and methanol (100 ml; 2/1) while sodium borohydride (1.5 g, 40 mmol) was added in small portions over 30 min. After stirring overnight, ice (about 50 ml) was added and the mixture was stirred for 0.5 h. The THF and MeOH were removed under reduced pressure. Ether (about 250 ml) was added, the pH was adjusted to pH 1 by the addition of aqueous HCl and the ether layer was separated. The ether was washed with saturated sodium bicarbonate solution, then brine, dried over $Na_2SO_4$, and evaporated under reduced pressure. The mixture of alcohol isomers (11.0 g, 43.5 mmol, 90 percent) was obtained as a waxy tan solid. It was used without purification.

The crude mix of isomeric alcohols was dissolved in toluene (150 ml) to which p-toluene sulfonic acid (0.5 g) was added. The solution was refluxed in a flask equipped with a Dean-Stark trap for 1.5 h then cooled. Solid sodium bicarbonate was added and the mixture was stored overnight in a refrigerator. The next morning water (100 ml) was added and the organic layer was separated, dried over $Na_2SO_4$, and stripped under reduced pressure. The product, 2-isopropyl-4-phenylindene (10.4 g) was obtained as a brown oil. Analysis by GC indicated a purity of >96 area percent. This material was stored cold under an inert atmosphere until ready for further conversion.

$^1$H-NMR (CDCl$_3$): δ1.18 (d, 6H), 2.74 (sept, 1H), 3.39 (s, 2H), 6.53 (s, 1H), 7.09–7.55 (m, 8H).

21B) Lithium 2-isopropyl-4-phenylindenide

To a toluene solution (25 ml) of 2-isopropyl-4-phenylindene (3.34 g, 14.25 mmol), in a glovebox filled with argon, was added n-butyl lithium (5.500 ml, 13.75 mmol). The mixture was stirred at room temperature overnight. The toluene was removed under reduced pressure. Hexane (20 ml) was added and removed under reduced pressure then added again (50 ml). The mixture was stirred for 1 h then filtered, washed with about 15 ml hexane and the filtrate dried under vacuum. The lithium indenide product (3.09 g) was obtained as an orange-brown powder. This material was stored in the glovebox until needed.

$^1$H-NMR (d$_8$-THF): δ1.27 (d, 6H), 3.02 (sept, 1H), 5.84 (s, 1H), 6.06 (s, 1H), 6.42–6.51 (m, 2H), 7.15 (t, 1H), 7.18 (d, 1H), 7.26 (t, 2H), 7.82 (d, 2H). $^{13}$C-NMR (d$_8$-THF): ppm 147.00, 141.54, 130.59, 130.40, 129.20, 128.16, 126.70, 125.02, 118.68, 113.92, 113.40, 91.01, 89.77, 30.62, 25.78.

21C) N,N-diisopropylamido bis(2-isopropyl-4-phenylindenyl)borane

To 25 ml toluene solution of N,N-diisopropylamidoboron dichloride (0.501 g, 2.75 mmole) at room temperature was added drop wise potassium (2-isopropyl-4-phenyl)indenide (1.50 g, 5.51 mmole in 20 ml toluene). The mixture was heated to reflux and stirred for 6 hours. The solution was cooled to room temperature, filtered through a medium frit, and solvent was removed under reduced pressure to give a light yellow solid (1.57 g, 99 percent). This material was further purified by column chromatography (silica gel/hexane) to yield 0.6 g (38 percent) of a light yellow solid (96 percent pure by GC).

21D) rac-diisopropylamidoborane-bis-$\eta^5$-(2-isopropyl-4-phenyl indenyl)zirconium $\eta^4$-1,4-diphenyl-1,3-butadiene In a glove box, N,N-diisopropylamino bis(2-isopropyl-4-phenylindenyl)borane (0.380 g, 0.660 mmole) was dissolved in 20 ml of toluene, 2.1 equivalents of potassium bis (trimethylsilyl)amide (0.276, 1.38 mmole) was added and the resulting mixture was stirred at room temperature for 24 hours. Removed volatiles under reduced pressure and washed. The resulting orange solid was combined with 10 ml of hexane, filtered and pumped dry. The dipotassium salt residue (0.415 g, 97 percent, 0.635 mmole) was redissolved in 20 ml of toluene, and (1,4-diphenyl-1,3-butadiene)bis (triethylphosphine)zirconium dichloride (0.384 g, 0.635 mmole) was added. The solution was stirred for 2 h at room temperature, followed by heating at 80° C. for 6 hours. The product mixture was cooled to room temperature, filtered through diatomaceous earth and the solvent of the filtrate was removed under reduced pressure. Further purification was carried out by recrystallization from hexane to yield 0.21 g (36 percent) of product as a dark red solid.

$^1$H NMR ($C_6D_6$): δ7.62(d, 2H); 7.42–6.7, (mm, 24 H); 5.79 (s, 2H); 4.5, sept, 2H); 3.45–3.57 (dd, 2H); 2.8–2.9 (sept, 2H)1.65–1.72 (dd, 2H); 1.35(d, 12H); 1.2–1.3 (m, 12H).

Example 22

Supported rac-diisopropylamidoborane-bis-$\eta^5$-(2-methyl-4-phenylinden-1-yl)zirconium $\eta^4$-1,4-diphenyl-1,3-butadiene In a glass flask, 0.922 ml of a toluene solution of methyldi(octyl)ammonium hydroxyphenyltris(pentafluorophenyl) borate (amounting to 0.070 mmoles based on boron) and 0.110 ml of a 1.9 M toluene solution of triethyl aluminum (0.058 mmoles) were added along with 0.290 ml additional toluene. The mixture was stirred for 5 minutes on a mechanical shaker. About one half (0.550 ml) of the resulting solution was added to a flask containing 0.500 g of thoroughly dried silica (Grace-Davison 948 silica, heated 250° C., 4 h). The mixture was shaken by hand to break-up clumps and then mechanically agitated for an additional 10 minutes. Next 8 ml of mixed hexanes was added to form a slurry, which was mechanically stirred for an additional 15 minutes. To this mixture, 3.5 ml of a 0.005 M toluene solution of rac-diisopropylamidoborane-bis-$\eta^5$-(2-methyl-4-phenylinden-1-yl)zirconium $\eta^4$-1,4-diphenyl-1,3-butadiene (Example 14) was added. The mixture was agitated 2 h on the mechanical shaker, filtered on a glass frit, washed (3×) with 10 ml mixed hexanes and dried under reduced pressure.

The resulting blue colored, dried, supported catalyst was analyzed by neutron activation for zirconium content and found to contain 31.8 μmole zirconium/g formulated supported catalyst.

Solution Polyethylene Polymerization

Mixed hexanes and 1-octene were purified by sparging with purified nitrogen followed by passage through columns containing alumina (A-2, available from LaRoche Inc.) and Q5 reactant (available from Englehard Chemicals Inc.) at 50 psig using a purified nitrogen pad. All transfers of solvents and solutions described below were accomplished using a gaseous pad of dry, purified nitrogen or argon. Gaseous feeds to the reactor were purified by passage through columns of A-204 alumina (available from LaRoche Inc.) and Q5 reactant. The aluminas were previously activated by treatment at 375° C. with nitrogen and Q5 reactant was activated by treatment at 200° C. with 5 percent hydrogen in nitrogen.

Batch reactor polymerizations were conducted in a two liter Parr reactor equipped with an electrical heating jacket, internal serpentine coil for cooling, and a bottom drain valve. Pressures, temperatures and block valves were computer monitored and controlled. Mixed alkanes solvent (about 740 g) and 1-octene (118 g) were measured in a solvent shot tank fitted with a differential pressure transducer or weigh cell. These liquids were then added to the reactor from the solvent shot tank. The contents of the reactor were stirred at 1200 rpm. Hydrogen was added by differential expansion (Δ25 psi, 170 kPa) from a 75 ml shot tank initially at 300 psig (2.1 Mpa). The contents of the reactor was then heated to the desired run temperature under 500 psig (3.4 Mpa) of ethylene pressure. The catalyst composition (as a 0.0050 M solution in toluene) and cocatalyst were combined in the desired ratio in the glove box and transferred from the glove box to the catalyst shot tank through 1/16 in (0.16 cm) tubing using toluene to aid in the transfer. The catalyst tank was then pressurized to 700 psig (4.8 Mpa) using nitrogen. After the contents of the reactor had stabilized at the desired run temperature of 140° C., the catalyst was injected into the reactor via a dip tube. The temperature was maintained by allowing cold ethylene glycol to pass through the internal cooling coils. The reaction was allowed to proceed for 15 minutes with ethylene provided on demand. Additional injections of catalyst composition prepared and injected in the same manner were employed where indicated. The contents of the reactor were then expelled into a 4 liter nitrogen purged vessel and quenched with isopropyl alcohol. Approximately 10 ml of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation) were added. Volatile materials were removed from the polymers in a vacuum oven that gradually heated the polymer to 140° C. overnight and cooled to at least 50° C. prior to removal from the oven. After completion of the polymerizaiton, the reactor was washed with 1200 ml of mixed hexanes solvent at 150° C. before reuse. Results are contained in Table 1.

TABLE 1

| Run | Catalyst | cocatalyst | Catalyst/cocatalyst (μmoles) | T (° C.) | Yield (g) | Density* g/ml | MMI** (dg/min.) |
|---|---|---|---|---|---|---|---|
| 1 | Ex. 2 | MATB$^1$ | 5/5 | 140 | 31.5 | 0.892 | 436 |
| 2 | " | " | " | " | 26.7 | 0.901 | 186 |
| 3 | " | MABU$^2$ | | " | 18.3 | 0.891 | 199 |
| 4 | " | TPB$^3$ | | " | 5.3 | 0.892 | 500+ |
| 5 | " | TPA$^4$ | 5/20 | " | 10.2 | 0.896 | 500+ |
| 6 | Ex. 3 | MATB$^1$ | 5/5 | " | 17.1 | 0.902 | 33 |
| 7 | " | " | " | " | 6.3 | 0.908 | 500+ |
| 8 | " | MABU$^2$ | | " | 0.3 | — | — |

TABLE 1-continued

| Run | Catalyst | cocatalyst | Catalyst/cocatalyst (μmoles) | T (°C.) | Yield (g) | Density* g/ml | MMI** (dg/min.) |
|---|---|---|---|---|---|---|---|
| 9 | " | TPB³ | | " | 4.5 | — | — |
| 10 | " | TPA⁴ | 5/20 | " | 0.7 | — | — |
| 11 | Ex. 17 | MAO⁵ | 1/1000 | " | 142.1 | — | 2.8 |
| 12 | " | " | 0.75/750 | " | 133.4 | — | 1.9 |
| 13 | Ex. 18 | " | 1/1000 | " | 130.8 | 0.90 | 1.8 |
| 14 | " | " | 0.5/500 | " | 120.6 | " | 1.1 |
| 15 | Ex. 20 | " | " | " | 164.9 | " | — |

*density is determined by displacement technique using methylethylketone
**micromelt index technique, calibrated using standards of known melt index.
¹methyldi(octadecyl)ammonium tetrakis(pentafluorophenl)borate (this ammonium cation is derived from a mixture of amines available commercially as methylbistallowamine).
²methylbis(octadecyl)ammonium bis(tris(pentafluorophenyl)aluminane)undecylimidazolide (prepared according to U.S. Ser. No. 09/251,664, filed Feb. 17, 1999)
³tris(pentafluorophenyl)borane, $(C_6F_5)_3B$
⁴tris(pentafluorophenyl)aluminane, $(C_6F_5)_3Al$
⁵methylalumoxane available from Albemarle Corp.

Solution Polypropylene Polymerization

The above reaction conditions were substantially repeated excepting about 625 g of mixed alkanes solvent and either 150 g of propylene (P) for homopolymer formation, or a mixture of 150 g propylene and 7 g ethylene (E) for copolymer formation were used. Hydrogen was added as a molecular weight control agent by differential pressure expansion from a 75 ml addition tank at about 17–25 psi (120–170 kPa). The reactor was heated to the polymerization temperature and the desired metal complex along with a cocatalyst, as dilute solutions in toluene, were mixed at an appropriate molar ratio, transferred to a catalyst addition tank, and injected into the reactor (three injections of 1 μmole, 3 μmole and 5 μmole based on zirconium over about 30 minutes for run 16, two injections of 5 μmole based on zirconium over about 20 minutes for run 17, and a single addition for all other runs. Results are contained in Table 2.

temperature was between 20° C. and 60° C., and no solvent was used. All feeds were passed through columns of alumina and a decontaminant (Q-5® catalyst available from Englehardt Chemicals Inc.) prior to introduction into the reactor. Catalyst and cocatalysts were handled in a glovebox containing an atmosphere of argon or nitrogen. A stirred 2.0 liter reactor was charged with about 500 g of propylene. Hydrogen was added by differential pressure expansion from a 75 ml addition tank at 40 psi (280 kPa). The reactor was adjusted to the initial polymerization temperature (25° C.) and a slurry of the supported catalyst composition (40 μg, 1.27 μmole Zr) in mixed hexanes was injected into the reactor. Temperature was maintained at 25° C. for 20 minutes then increased to 60° C. over 6.5 minutes (2.8 minutes for run 33) and maintained at 60° C. for a total run time of 40 minutes.

Upon completion, the reactor contents were removed and about 10 ml of a toluene solution containing approximately

TABLE 2

| Run | Catalyst | cocatalyst | Catalyst/cocatalyst (μmoles) | monomer | T (°C.) | Time (min.) | Yield (g) | Tm (°C.) | Mw ×10⁻³ |
|---|---|---|---|---|---|---|---|---|---|
| 16 | Ex. 1 | MAO¹ | 9/9000 | P | 70 | 51 | 9.2 | 155.6 | — |
| 17 | Ex. 1 | " | 10/10,000 | E/P | " | 58 | 10.3 | 145.9 | — |
| 18 | Ex. 5 | MDAP² | 1/1.25 | P | " | 7 | 43.5 | 155.8 | — |
| 19 | Ex. 5 | MABU³ | 0.25/0.25 | " | " | " | 29.8 | 155.7 | 357 |
| 20 | Ex. 13 | " | " | " | " | 30 | 33.5 | 157.3 | 330 |
| 21 | Ex. 5 | " | 0.5/0.5 | " | 85 | 5 | 42.2 | 152.2 | 195 |
| 22 | Ex. 13 | " | 0.75/0.75 | " | " | " | 41.3 | 153.9 | 183 |
| 23 | Ex. 5 | " | 0.5/0.5 | " | 100 | " | 12.4 | 151.4 | 136 |
| 24 | Ex. 13 | " | 0.75/0.75 | " | " | " | 16.2 | 150.3 | 117 |
| 25 | Ex. 5 | " | 1.5/1.5 | " | 115 | 12 | 19.8 | 146.7 | 75 |
| 26 | Ex. 13 | " | 1.75/1.75 | " | " | 10 | 19.4 | 147.4 | 69 |
| 27 | Ex. 5 | " | 2.5/25 | " | 130 | 11 | 12.7 | 143.2 | 48 |
| 28 | Ex. 13 | " | 3.75/3.75 | " | " | 17 | 16.4 | 142.0 | 15 |
| 29 | Ex. 17 | MAO | 6/6000 | " | 70 | | 118.9 | 117 | 114 |
| 30 | Ex. 18 | " | " | " | " | | 107.9 | 112 | 111 |
| 31 | Ex. 20 | " | " | " | " | | 126.6 | 108 | — |
| 32 | Ex. 16 | MABU | 0.75/0.75 | " | 90 | 15 | 96.4 | 152.7 | — |

¹methylalumoxane available from Albermarle Corp.
²methyldi(octadecyl)ammoniumtris(pentafluorophenyl)(p-(diethylaluminoxyphenyl) borate (formed by reaction of triethylaluminum and methyldi(octadecyl)ammonium tris(pentafluorophenyl)(hydroxyphenyl) borate)
³methylbis(octadecyl)ammonium bis(tris(pentafluorophenyl)aluminane)undecylimidazolide Slurry Polymerization The previous reaction conditions were substantially repeated excepting a supported catalyst was employed, the 67 mg of a hindered phenol antioxidant (Irganox™ 1010 from Ciba Geigy Corporation) and 133 mg of a phosphorus stabilizer (Irgafos™ 168 from Ciba Geigy Corporation)

were added. The polymer was recovered by drying in a vacuum oven set at 140° C. for about 20 hours. Results are contained in Table 3.

TABLE 3

| Run | Catalyst (mg) | Zr (μmole) | Yield (g) | Tm (° C.) | Mw ×10⁻³ | Mw/Mn |
|---|---|---|---|---|---|---|
| 32 | Ex. 22 (40) | 1.27 | 61.5 | 150 | 283 | 3.0 |
| 33 | Ex. 22 (32) | 1.02 | 47.4 | — | — | — |

What is claimed is:

1. A Group 4 transition metal complex corresponding to the following formula:

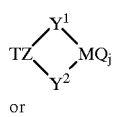

Formula 1 or

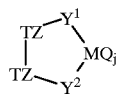

Formula 2 wherein:

M is titanium, zirconium, or hafnium in the +4, +3, or +2 oxidation state;

$Y^1$ and $Y^2$ are independently an anionic, cyclic or non-cyclic, π-bonded group, $NR^1$, $PR^1$; $NR^1{}_2$ or $PR^1{}_2$;

Z is boron or aluminum;

Q is a neutral, anionic or dianionic ligand group depending on the oxidation state of M;

j is 1, 2 or 3 depending on the oxidation state of M and the electronic nature of Q;

T independently each occurrence is:

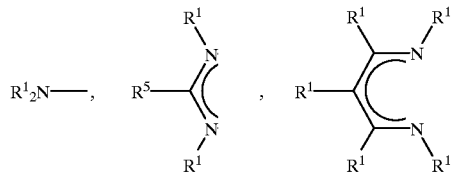

or

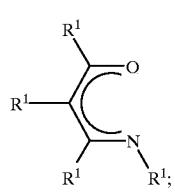

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups together or one or more $R^1$ groups together with $R^5$ may optionally be joined to form a ring structure.

2. A metal complex according to claim 1 corresponding to formula 4, 5, 6, 7, 8 or 9:

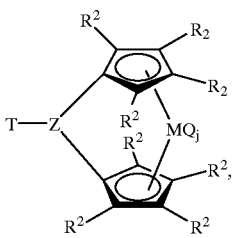

Formula 4

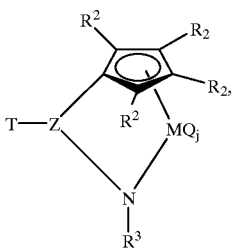

Formula 5

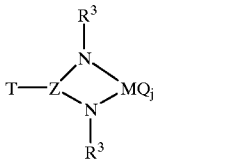

Formula 6

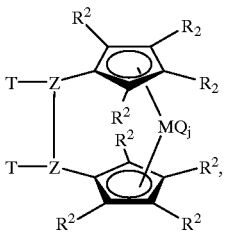

Formula 7

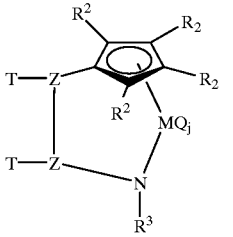

Formula 8 or

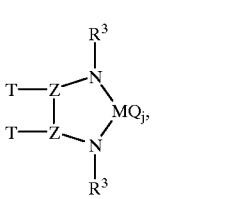

Formula 9 wherein M, Z, T, $R^1$, Q and j are as defined in claim 1;

$R^2$ is hydrogen, or a hydrocarbyl, halohydrocarbyl, dihydrocarbylaminohydrocarbyl, tri(hydrocarbylsilyl)hydrocarbyl, $Si(R^3)_3$, $N(R^3)_2$, or $OR^3$ group of up to 20 carbon or silicon atoms, and optionally two adjacent $R^2$ groups can be joined together, thereby forming a fused ring structure; and $R^3$ is independently hydrogen, a hydrocarbyl group, a trihydrocarbylsilyl group or a trihydrocarbylsilylhydrocarbyl group, said $R^3$ having up to 20 atoms not counting hydrogen.

3. A metal complex according to claim 1 wherein M is zirconium or hafnium.

4. A metal complex according to claim 3 wherein Z is boron.

5. An olefin polymerization process comprising contacting one or more olefin monomers under polymerization conditions with a catalyst composition comprising a metal complex according to any one of claims 1–4.

6. A metal complex according to claim 2 wherein M is in the +4 oxidation state, j=2 and Q independently each occurrence is halide, hydride, hydrocarbyl, silylhydrocarbyl, hydrocarbyloxide, or dihydrocarbylamide, said Q having up to 20 atoms not counting hydrogen, or two Q groups together form an alkanediyl group or a conjugated $C_{4-40}$ diene ligand that together with M form a metallocyclopentene.

7. A metal complex according to claim 6 corresponding to Formula 4a, 5a, 6a, 7a, 8a, or 9a, wherein the definitions of M, Z, $R^1$, $R^2$, and $R^3$ are as defined in claim 6:

Formula 4a
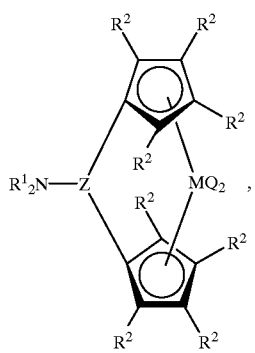

Formula 5a
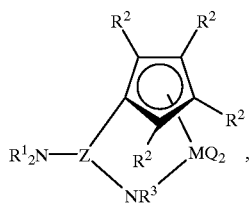

Formula 6a
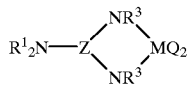

Formula 7a
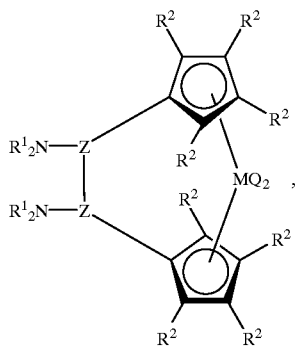

Formula 8a
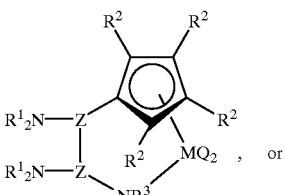
, or

Formula 9a
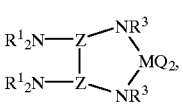

and Q, independently each occurrence is a halide, hydrocarbyl, hydrocarbyloxy, or dihydrocarbylamide group of up to 10 atoms not counting hydrogen, or two Q groups together form a $C_{4-20}$ diene ligand that together with M forms a metallocyclopentene.

8. A Group 4 transition metal complex corresponding to the following formula:

Formula 1
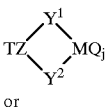

or

Formula 2
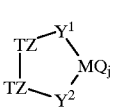

wherein:
M is titanium, zirconium, or hafnium in the +4 oxidation state;
$Y^1$ and $Y^2$ are independently an anionic, cyclic or non-cyclic, π-bonded group, $NR^1$ or $PR^1$;
Z is boron or aluminum;
Q is an anionic or dianionic ligand group;
j is 1 or 2;
T independently each occurrence is:

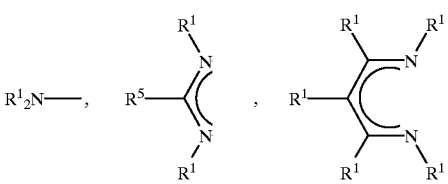

or

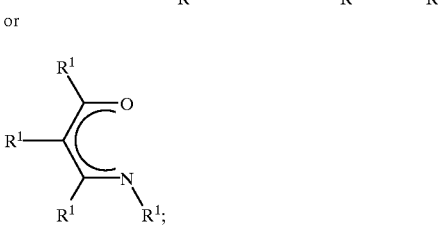

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups in T together or one or more $R^1$ groups in T together with $R^5$ may optionally be joined to form a ring structure.

9. A metal complex according to claim 8 corresponding to formula 4, 5, 6, 7, 8 or 9:

Formula 4

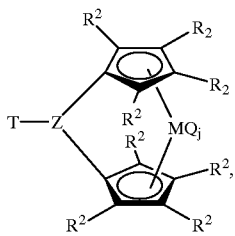

Formula 5

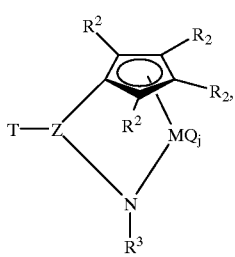

Formula 6

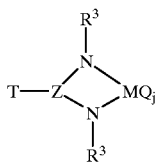

Formula 7

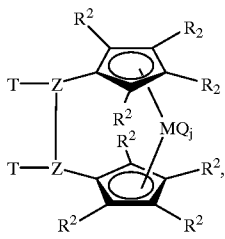

Formula 8

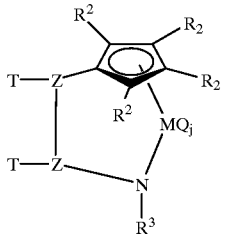

or

Formula 9

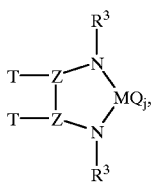

wherein M, Z, T, $R^1$, Q and j are as defined in claim 1;
$R^2$ is hydrogen, or a hydrocarbyl, halohydrocarbyl, dihydrocarbylaminohydrocarbyl, tri(hydrocarbylsilyl) hydrocarbyl, $Si(R^3)_3$, $N(R^3)_2$, or $OR^3$ group of up to 20 carbon or silicon atoms, and optionally two adjacent $R^2$ groups can be joined together, thereby forming a fused ring structure; and $R^3$ is independently hydrogen, a hydrocarbyl group, a trihydrocarbylsilyl group or a trihydrocarbylsilylhydrocarbyl group, said $R^3$ having up to 20 atoms not counting hydrogen.

10. A metal complex according to claim 9 wherein j=2 and Q independently each occurrence is halide, hydride, hydrocarbyl, silylhydrocarbyl, hydrocarbyloxide, or dihydrocarbylamide, said Q having up to 20 atoms not counting hydrogen.

11. A metal complex according to claim 10 wherein T is $R'_2N—$, $R'$ is hydrocarbyl, and Q, independently each occurrence is a halide, hydrocarbyl, hydrocarbyloxy, or dihydrocarbylamide group of up to 10 atoms not counting hydrogen.

12. A metal complex according to claim 8 wherein M is zirconium or hafnium.

13. A metal complex according to claim 8 wherein Z is boron.

14. A metal complex according to claim 8 which is:
dimethylamidoborane-bis($\eta^5$-cyclopentadienyl) zirconium dichloride, dimethylamidoboranebis($\eta^5$-inden-1-yl)zirconium dichloride, dimethylamidoborane-bis($\eta^5$-2-methyl-4-phenylinden-1-yl)zirconium dichloride, dimethylamidoborane-bis($\eta^5$-2-ethyl-4-phenylinden-1-yl)zirconium dichloride, dimethylamidoborane-bis($\eta^5$-2-isopropyl-4-phenylinden-1-yl)zirconium dichloride, dimethylamidoborane-bis($\eta^5$-2-methyl-4-bis(3,5-trifluoromethyl)phenylinden-1-yl)zirconium dichloride, dimethylamidoborane-bis($\eta^5$-3-t-butylinden-1-yl)zirconium dichloride, diisopropylamidoborane-bis($\eta^5$-cyclopentadienyl) zirconium dichloride, diisopropylamidoboranebis($\eta^5$-inden-1-yl)zirconium dichloride, diisopropylamidoborane-bis($\eta5$-2-methyl-4-phenylinden-1-yl)zirconium dichloride, diisopropylamidoborane-bis($\eta^5$-2-ethyl-4-phenylinden-1-yl)zirconium dichloride, diisopropylamidoborane-bis($\eta^5$-2-isopropyl-4-phenylinden-1-yl)zirconium dichloride, diisopropylamidoborane-bis($\eta^5$-2-methyl-4-bis(3,5-trifluoromethyl)phenylinden-1-yl)zirconium dichloride, diisopropylamidoborane-bis($\eta^5$-3-t-butylinden-1-yl)zirconium dichloride, diphenylamidoborane-bis($\eta^5$-cyclopentadienyl) zirconium dichloride, diphenylamidoboranebis($\eta^5$-inden-1-yl)zirconium dichloride, diphenylamidoborane-bis($\eta^5$-2-methyl-4-phenylinden-1-yl)zirconium dichloride, diphenylamidoborane-bis($\eta^5$-2-ethyl-4-phenylinden-1-yl)zirconium dichloride, diphenylamidoborane-bis($\eta^5$-2-isopropyl-4-phenylinden-1-yl)zirconium dichloride, diphenylamidoborane-bis($\eta^5$-2-methyl-4-bis(3,5-trifluoromethyl)phenylinden-1-yl)zirconium dichloride, or diphenylamidoborane-bis($\eta^5$-3-t-butylinden-1-yl)zirconium dichloride.

15. A metal complex according to claim 2 wherein M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, said Q being further substituted with an amine, phosphine, ether, or thioether containing substituent able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$-bond with M.

16. A metal complex according to claim 2 wherein M is in the +2 oxidation state, j=1 and Q is a neutral conjugated diene, optionally substituted with one or more tri(hydrocarbyl)silyl or tri(hydrocarbylsilyl)hydrocarbyl groups, said Q having up to 40 carbon atoms and forming a π-complex with M.

17. A metal complex according to claim 15 corresponding to Formula 4b, 5b, 6b, 7b, 8b, or 9b, wherein the definitions of M, Z, $R^1$, $R^2$, and $R^3$ are as defined in claim 15:

Formula 4b

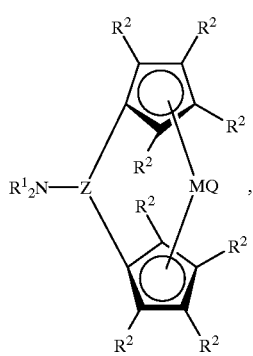

Formula 5b

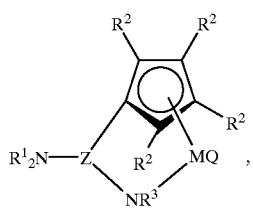

Formula 6b

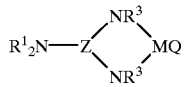

Formula 7b

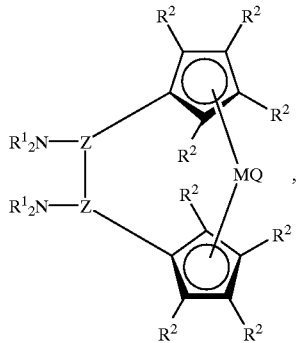

Formula 8b

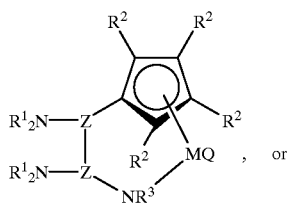

or

Formula 9b

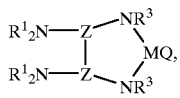

and Q, each occurrence is a monovalent anionic stabilizing ligand selected from the group consisting of alkyl, cycloalkyl, aryl, and silyl groups, said group being further substituted with one or more amine, phosphine, or ether substituents able to form a coordinate-covalent bond or chelating bond with M, and said Q having up to 30 non-hydrogen atoms; or Q is a $C_{3-10}$ hydrocarbyl group comprising an ethylenic unsaturation able to form an $\eta^3$ bond with M.

18. A metal complex according to claim 16 corresponding to Formula 4c, 5c, 6c, 7c, 8c, or 9c, wherein the definitions of M, Z, $R^1$, $R^2$, and $R^3$ are as defined in claim 16:

Formula 4c

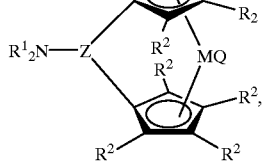

Formula 5c

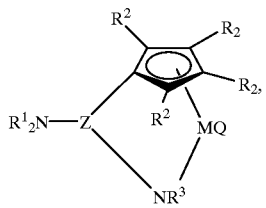

Formula 6c

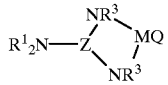

Formula 7c

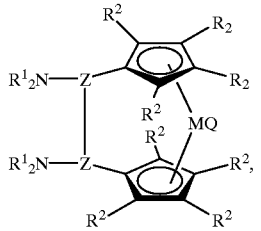

Formula 8c

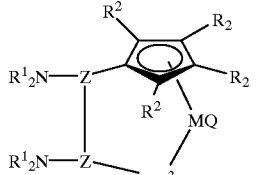

or

-continued

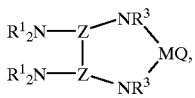
Formula 9c and Q, each occurrence is a neutral conjugated diene, optionally substituted with one or more tri(hydrocarbyl)silyl groups or tri(hydrocarbyl)silylhydrocarbyl groups, said Q having up to 30 atoms not counting hydrogen and forming a π-complex with M.

19. A Group 4 transition metal complex corresponding to the following formula:

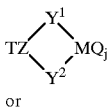
Formula 1 or

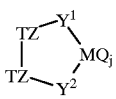
Formula 2 wherein:
M is titanium, zirconium, or hafnium in the +3, or +2 oxidation state;
$Y^1$ and $Y^2$ are independently an anionic, cyclic or non-cyclic, π-bonded group, $NR^1$, $PR^1$; $NR^1_2$ or $PR^1_2$;
Z is boron or aluminum;
Q is a neutral ligand group or an anionic ligand group depending on the oxidation state of M;
j is 1 or 2;
T independently each occurrence is:

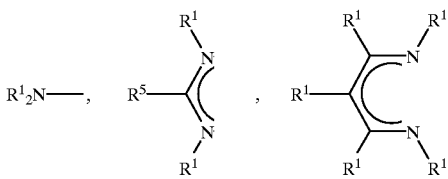

or

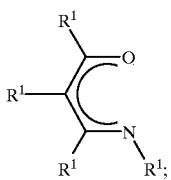

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;
$R^5$ is $R^1$ or $N(R^1)_2$; and
two $R^1$ groups in T together or one or more $R^1$ groups in T together with $R^5$ may optionally be joined to form a ring structure.

20. A metal complex according to claim 19 corresponding to formula 4, 5, 6, 7, 8 or 9:

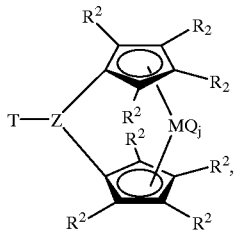
Formula 4

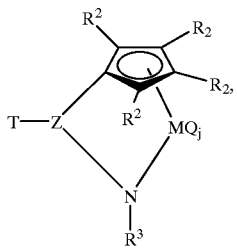
Formula 5

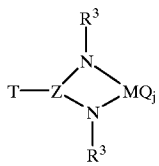
Formula 6

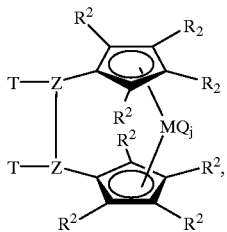
Formula 7

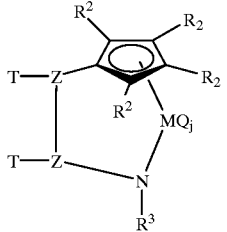
Formula 8 or

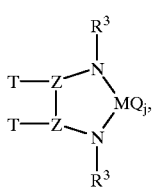
Formula 9 wherein M, Z, T, $R^1$, Q and j are as defined in claim 19;

$R^2$ is hydrogen, or a hydrocarbyl, halohydrocarbyl, dihydrocarbylaminohydrocarbyl, tri(hydrocarbylsilyl)hydrocarbyl, $Si(R^3)_3$, $N(R^3)_2$, or $OR^3$ group of up to 20 carbon or silicon atoms, and optionally two adjacent $R^2$ groups can be joined together, thereby forming a fused ring structure; and R³ is independently hydrogen, a hydrocarbyl group, a trihydrocarbylsilyl group or a trihydrocarbylsilylhydrocarbyl group, said R³ having up to 20 atoms not counting hydrogen.

21. A metal complex according to claim 19 wherein M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, said Q being further substituted with an amine, phosphine, ether, or thioether containing substituent able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$-bond with M.

22. A metal complex according to claim 19 wherein M is in the +2 oxidation state, j=1 and Q is a neutral conjugated diene, optionally substituted with one or more tri(hydrocarbyl)silyl or tri(hydrocarbylsilyl)hydrocarbyl groups, said Q having up to 40 carbon atoms and forming a π-complex with M.

23. A metal complex according to claim 20 corresponding to Formula 4b, 5b, 6b, 7b, 8b, or 9b, wherein the definitions of M, Z, R¹, R², and R³ are as defined in claim 20:

Formula 4b

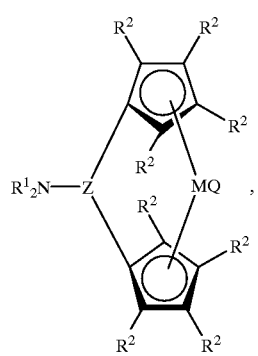

Formula 5b

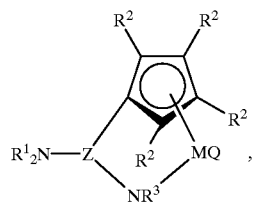

Formula 6b

Formula 7b

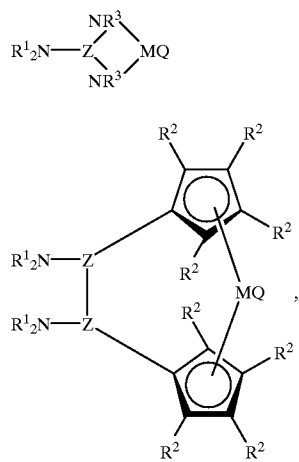

-continued

Formula 8b

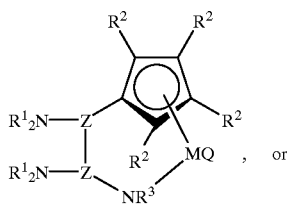

Formula 9b

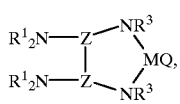

and Q, each occurrence is a monovalent anionic stabilizing ligand selected from the group consisting of alkyl, cycloalkyl, aryl, and silyl groups, said group being further substituted with one or more amine, phosphine, or ether substituents able to form a coordinate-covalent bond or chelating bond with M, and said Q having up to 30 non-hydrogen atoms; or Q is a $C_{3-10}$ hydrocarbyl group comprising an ethylenic unsaturation able to form an $\eta^3$ bond with M.

24. A metal complex according to claim 20 corresponding to Formula 4c, 5c, 6c, 7c, 8c, or 9c, wherein the definitions of M, Z, R¹, R², and R³ are as defined in claim 20:

Formula 4c

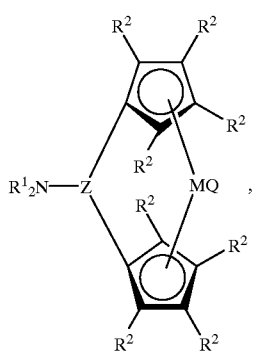

Formula 5c

Formula 6c

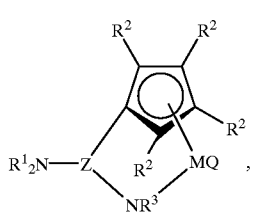

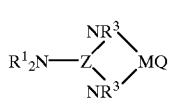

-continued

Formula 7c

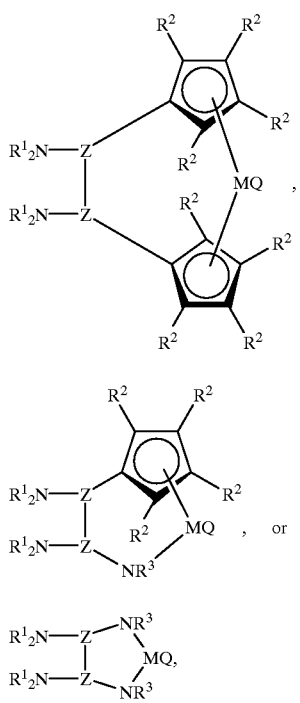

Formula 8c

Formula 9c and Q, each occurrence is a neutral conjugated diene, optionally substituted with one or more tri(hydrocarbyl)silyl groups or tri(hydrocarbyl)silylhydrocarbyl groups, said Q having up to 30 atoms not counting hydrogen and forming a π-complex with M.

25. A metal complex according to claim 19 wherein M is zirconium or hafnium.

26. A metal complex according to claim 19 wherein Z is boron.

27. A metal complex according to claim 19 which is:
dimethylamidoborane-bis($\eta^5$-cyclopentadienyl) zirconium 1,4-diphenyl-1,3-butadiene, dimethylamidoboranebis($\eta^5$-inden-1-yl)zirconium 1,4-diphenyl-1,3-butadiene, dimethylamidoborane-bis($\eta^5$-2-methyl-4-phenylinden-1-yl)zirconium 1,4-diphenyl-1,3-butadiene, dimethylamidoborane-bis($\eta^5$-2-ethyl-4-phenylinden-1-yl)zirconium 1,4-diphenyl-1,3-butadiene, dimethylamidoborane-bis($\eta^5$-2-isopropyl-4-phenylinden-1-yl)zirconium 1,4-diphenyl-1,3-butadiene, dimethylamidoborane-bis($\eta^5$-2-methyl-4-bis(3,5-trifluoromethyl)phenylinden-1-yl)zirconium 1,4-diphenyl-1,3-butadiene, dimethylamidoborane-bis($\eta^5$-3-t-butylinden-1-yl)zirconium 1,4-diphenyl-1,3-butadiene,
diisopropylamidoborane-bis($\eta^5$-cyclopentadienyl) zirconium 1,4-diphenyl-1,3-butadiene, diisopropylamidoboranebis($\eta^5$-inden-1-yl)zirconium 1,4-diphenyl-1,3-butadiene, diisopropylamidoborane-bis($\eta^5$-2-methyl-4-phenylinden-1-yl)zirconium 1,4-diphenyl-1,3-butadiene, diisopropylamidoborane-bis($\eta^5$-2-ethyl-4-phenylinden-1-yl)zirconium 1,4-diphenyl-1,3-butadiene, diisopropylamidoborane-bis($\eta^5$-2-isopropyl-4-phenylinden-1-yl)zirconium 1,4-diphenyl-1,3-butadiene, diisopropylamidoborane-bis($\eta^5$-2-methyl-4-bis(3,5-trifluoromethyl)phenylinden-1-yl)zirconium 1,4-diphenyl-1,3-butadiene, diisopropylamidoborane-bis($\eta^5$-3-t-butylinden-1-yl)zirconium 1,4-diphenyl-1,3-butadiene,
diphenylamidoborane-bis($\eta^5$-cyclopentadienyl) zirconium 1,4-diphenyl-1,3-butadiene, diphenylamidoboranebis($\eta^5$-inden-1-yl)zirconium 1,4-diphenyl-1,3-butadiene, diphenylamidoborane-bis($\eta^5$-2-methyl-4-phenylinden-1-yl)zirconium 1,4-diphenyl-1,3-butadiene, diphenylamidoborane-bis($\eta^5$-2-ethyl-4-phenylinden-1-yl)zirconium 1,4-diphenyl-1,3-butadiene, diphenylamidoborane-bis($\eta^5$-2-isopropyl-4-phenylinden-1-yl)zirconium 1,4-diphenyl-1,3-butadiene, diphenylamidoborane-bis($\eta^5$-2-methyl-4-bis(3,5-trifluoromethyl)phenylinden-1-yl)zirconium 1,4-diphenyl-1,3-butadiene, or diphenylamidoborane-bis($\eta^5$-3-t-butylinden-1-yl)zirconium 1,4-diphenyl-1, 3-butadiene.

28. A Group 4 transition metal complex corresponding to the following formula:

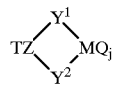

Formula 1 or

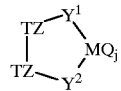

Formula 2 wherein:

M is titanium, zirconium, or hafnium in the +4, +3, or +2 oxidation state;

$Y^1$ and $Y^2$ are independently an anionic, cyclic or non-cyclic, π-bonded group, $NR^1$, $PR^1$; $NR^1{}_2$ or $PR^1{}_2$;

Z is boron or aluminum;

Q is a neutral, anionic or dianionic ligand group depending on the oxidation state of M;

j is 1, 2 or 3 depending on the oxidation state of M and the electronic nature of Q;

T independently each occurrence is:

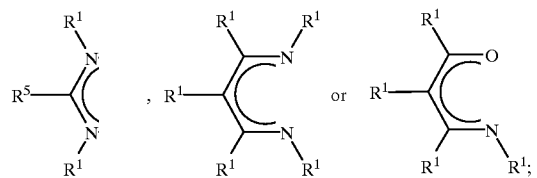

wherein $R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups in T together or one or more $R^1$ groups in T together with $R^5$ may optionally be joined to form a ring structure.

29. A Group 4 transition metal complex corresponding to the following formula:

Formula 2

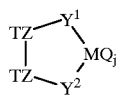

wherein:

M is titanium, zirconium, or hafnium in the +4, +3, or +2 oxidation state;

$Y^1$ and $Y^2$ are independently an anionic, cyclic or non-cyclic, π-bonded group, $NR^1$, $PR^1$; $NR^1_2$ or $PR^1_2$;

Z is boron or aluminum;

Q is a neutral, anionic or dianionic ligand group depending on the oxidation state of M;

j is 1, 2 or 3 depending on the oxidation state of M and the electronic nature of Q;

T independently each occurrence is:

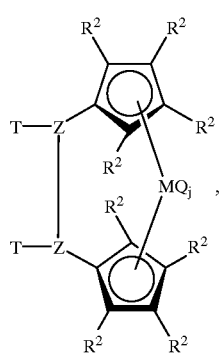

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups in T together or one or more $R^1$ groups in T together with $R^5$ may optionally be joined to form a ring structure.

30. A metal complex according to claim 29 corresponding to formula 7, 8 or 9:

Formula 7

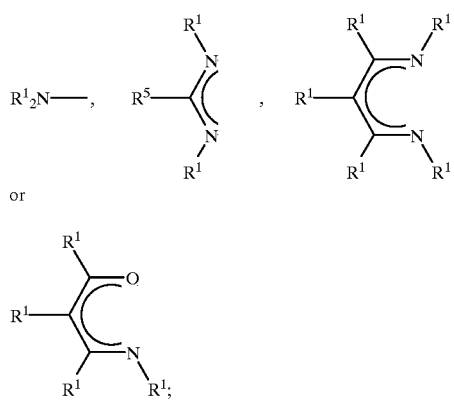

Formula 8

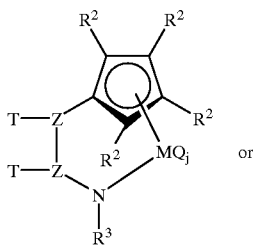

or

Formula 9

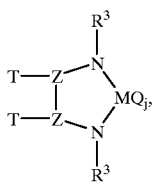

wherein M, Z, T, $R^1$, Q and j are as defined in claim 29;

$R^2$ is hydrogen, or a hydrocarbyl, halohydrocarbyl, dihydrocarbylaminohydrocarbyl, tri(hydrocarbylsilyl)hydrocarbyl, $Si(R^3)_3$, $N(R^3)_2$, or $OR^3$ group of up to 20 carbon or silicon atoms, and optionally two adjacent $R^2$ groups can be joined together, thereby forming a fused ring structure; and $R^3$ is independently hydrogen, a hydrocarbyl group, a trihydrocarbylsilyl group or a trihydrocarbylsilylhydrocarbyl group, said $R^3$ having up to 20 atoms not counting hydrogen.

31. A metal complex according to claim 30 wherein M is in the +4 oxidation state, j=2 and Q independently each occurrence is halide, hydride, hydrocarbyl, silylhydrocarbyl, hydrocarbyloxide, or dihydrocarbylamide, said Q having up to 20 atoms not counting hydrogen, or two Q groups together form an alkanediyl group or a conjugated $C_{4-40}$ diene ligand that together with M form a metallocyclopentene.

32. A metal complex according to claim 30 wherein M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, said Q being further substituted with an amine, phosphine, ether, or thioether containing substituent able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$-bond with M.

33. A metal complex according to claim 30 wherein M is in the +2 oxidation state, j=1 and Q is a neutral conjugated diene, optionally substituted with one or more tri(hydrocarbyl)silyl or tri(hydrocarbylsilyl)hydrocarbyl groups, said Q having up to 40 carbon atoms and forming a π-complex with M.

34. A Group 4 transition metal complex corresponding to the following formula:

Formula 1

$$TZ\underset{Y^2}{\overset{Y^1}{\diagdown}}MQ_j$$

or

Formula 2

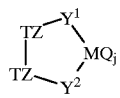

wherein:

M is titanium, zirconium, or hafnium in the +4, +3, or +2 oxidation state;

$Y^1$ and $Y^2$ are independently an anionic, cyclic or non-cyclic, π-bonded group, $NR^1$, $PR^1$; $NR^1_2$ or $PR^1_2$;

Z is boron or aluminum;

Q is a neutral, anionic or dianionic ligand group depending on the oxidation state of M;

j is 1, 2 or 3 depending on the oxidation state of M and the electronic nature of Q; and T each occurrence is $(CH_3)_2N$—.

35. A metal complex according to claim 34 corresponding to formula 4, 5, 6, 7, 8 or 9:

Formula 4

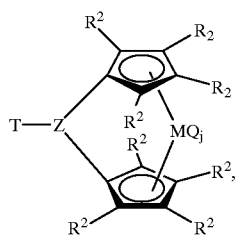

Formula 5

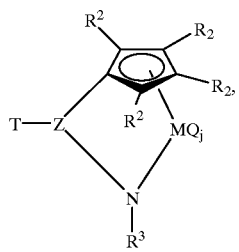

Formula 6

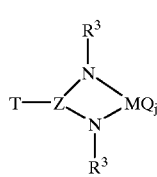

Formula 7

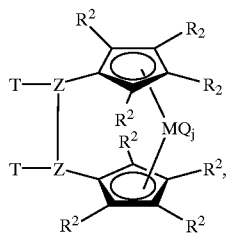

Formula 8

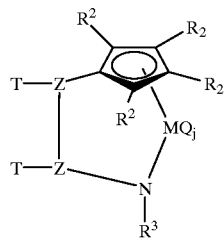

or

Formula 9

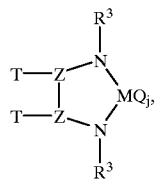

wherein M, Z, T, Q and j are as defined in claim 34;

$R^2$ is hydrogen, or a hydrocarbyl, halohydrocarbyl, dihydrocarbylaminohydrocarbyl, tri(hydrocarbylsilyl)hydrocarbyl, $Si(R^3)_3$, $N(R^3)_2$, or $OR^3$ group of up to 20 carbon or silicon atoms, and optionally two adjacent $R^2$ groups can be joined together, thereby forming a fused ring structure; and $R^3$ is independently hydrogen, a hydrocarbyl group, a trihydrocarbylsilyl group or a trihydrocarbylsilylhydrocarbyl group, said $R^3$ having up to 20 atoms not counting hydrogen.

36. A metal complex according to claim 35 wherein M is in the +4 oxidation state, j=2 and Q independently each occurrence is halide, hydride, hydrocarbyl, silylhydrocarbyl, hydrocarbyloxide, or dihydrocarbylamide, said Q having up to 20 atoms not counting hydrogen, or two Q groups together form an alkanediyl group or a conjugated $C_{4-40}$ diene ligand that together with M form a metallocyclopentene.

37. A metal complex according to claim 35 wherein M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, said Q being further substituted with an amine, phosphine, ether, or thioether containing substituent able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$-bond with M.

38. A metal complex according to claim 35 wherein M is in the +2 oxidation state, j=1 and Q is a neutral conjugated diene, optionally substituted with one or more tri(hydrocarbyl)silyl or tri(hydrocarbylsilyl)hydrocarbyl groups, said having up to 40 carbon atoms and forming a π-complex with M.

39. A metal complex according to claim 35 corresponding to Formula 4a, 5a, 6a, 7a, 8a, or 9a, wherein the definitions of M, Z, $R^2$, and $R^3$ are as defined in claim 35:

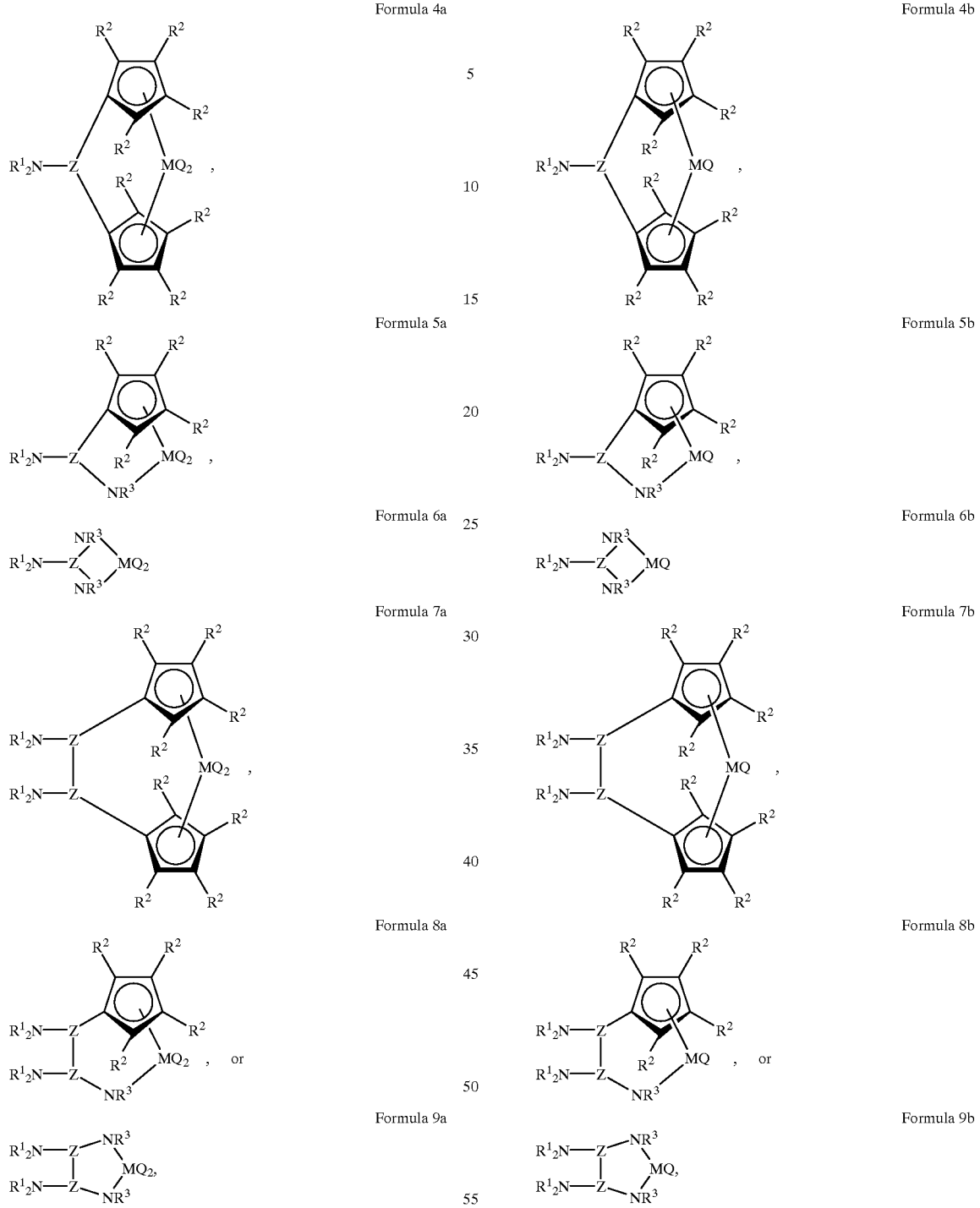

Formula 4a, Formula 4b, Formula 5a, Formula 5b, Formula 6a, Formula 6b, Formula 7a, Formula 7b, Formula 8a, Formula 8b, Formula 9a, Formula 9b and $R^1$ each occurrence is methyl; and Q, independently each occurrence is a halide, hydrocarbyl, hydrocarbyloxy, or dihydrocarbylamide group of up to 10 atoms not counting hydrogen, or two Q groups together form a $C_{4-20}$ diene ligand that together with M forms a metallocyclopentene.

40. A metal complex according to claim 35 corresponding to Formula 4b, 5b, 6b, 7b, 8b, or 9b, wherein the definitions of M, Z, $R^2$, and $R^3$ are as defined in claim 35:

and $R^1$ each occurrence is methyl, and Q, each occurrence is a monovalent anionic stabilizing ligand selected from the group consisting of alkyl, cycloalkyl, aryl, and silyl groups, said group being further substituted with one or more amine, phosphine, or ether substituents able to form a coordinate-covalent bond or chelating bond with M, and said Q having up to 30 non-hydrogen atoms; or Q is a $C_{3-10}$ hydrocarbyl group comprising an ethylenic unsaturation able to form an $\eta^3$ bond with M.

41. A metal complex according to claim 35 corresponding to Formula 4c, 5c, 6c, 7c, 8c, or 9c, wherein the definitions of M, Z, $R^2$, and $R^3$ are as defined in claim 35:

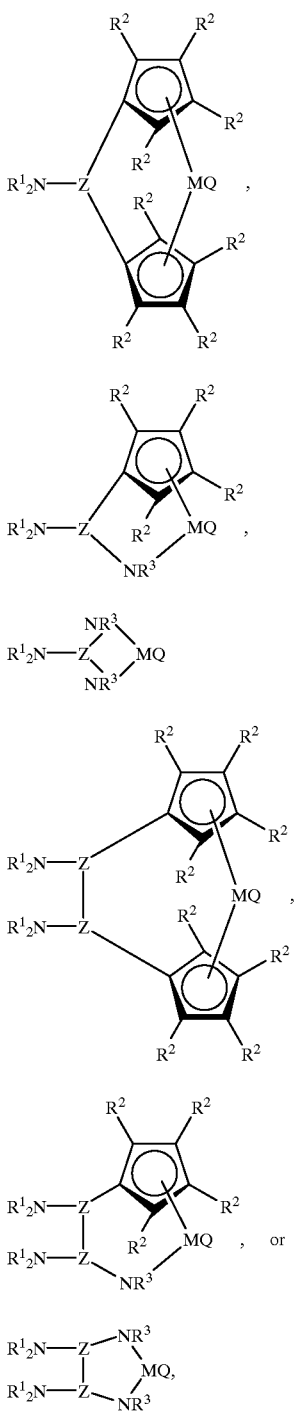

Formula 4c

Formula 5c

Formula 6c

Formula 7c

Formula 8c

Formula 9c and $R^1$ each occurrence is methyl, and Q, each occurrence is a neutral conjugated diene, optionally substituted with one or more tri(hydrocarbyl)silyl groups or tri(hydrocarbyl)silylhydrocarbyl groups, said Q having up to 30 atoms not counting hydrogen and forming a π-complex with M.

42. A metal complex according to claim 35 wherein M is zirconium or hafnium.

43. A metal complex according to claim 35 wherein Z is boron.

44. A Group 4 transition metal complex corresponding to the following formula:

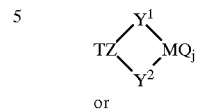

Formula 1 or

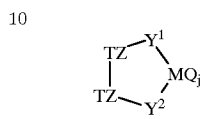

Formula 2 wherein:

M is titanium, zirconium, or hafnium in the +4, +3, or +2 oxidation state;

$Y^1$ and $Y^2$ are independently an anionic, cyclic or non-cyclic, π-bonded group, $NR^1$, $PR^1$; $NR^1_2$ or $PR^1_2$;

Z is boron or aluminum;

Q is a neutral, anionic or dianionic ligand group depending on the oxidation state of M;

j is 1, 2 or 3 depending on the oxidation state of M and the electronic nature of Q;

T independently each occurrence is:

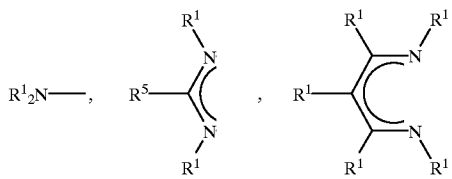

or

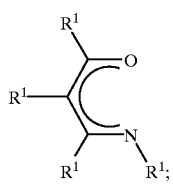

and two $R^1$ groups in T together or one or more $R^1$ groups in T together with $R^5$ are joined to form a ring structure.

45. A process for preparing a metal complex corresponding to the formula:

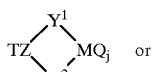

Formula 1

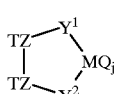

Formula 2 wherein:

M is titanium, zirconium, or hafnium in the +2 oxidation state;

$Y^1$ and $Y^2$ are independently an anionic, cyclic or non-cyclic, π-bonded group, $NR^1$ or $PR^1$;

Z is boron or aluminum;

Q is a neutral ligand group;

j is 1;

T independently each occurrence is:

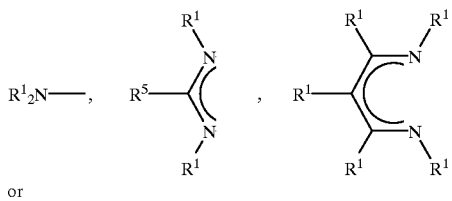

or

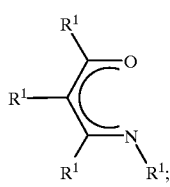

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups in T together or one or more $R^1$ groups in T together with $R^5$ may optionally be joined to form a ring structure, said process comprising contacting a compound having a ligand structure of formula 1A or 2A

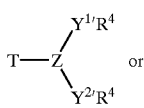   Formula 1A

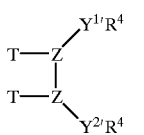   Formula 2A $Y^{1'}$ and $Y^{2'}$ are independently an anionic, cyclic or non-cyclic, π-bonded group, $NR^1$ or $PR^1$;
and T and Z, are as previously defined,
or a deprotonated dianionic derivative thereof,
with a Group 4 precursor of the formula 3:

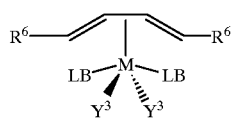   Formula 3 wherein M is defined as above;

$Y^3$ is a leaving group;

$R^6$ independently each occurrence is hydrogen, a hydrocarbyl group, a tri(hydrocarbyl)silyl group, or a tri(hydrocarbyl)silylhydrocarbyl group, said $R^6$ groups containing up to 20 atoms not counting hydrogen; and LB is a Lewis base of up to 20 carbons.

46. The process of claim 45 that is conducted in an aliphatic or aromatic hydrocarbon or ether, at a temperature from −100° C. to 150° C.

47. A compound of formula 1A or 2A

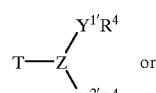   Formula 1A

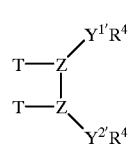   Formula 2A wherein $R^4$ is trimethylsilyl;

$Y^{1'}$ and $Y^{2'}$ are independently an anionic, cyclic or non-cyclic, π-bonded group, $NR^1$, $PR^1$; $NR^1_2$ or $PR^1_2$;

Z is boron or aluminum;

T independently each occurrence is:

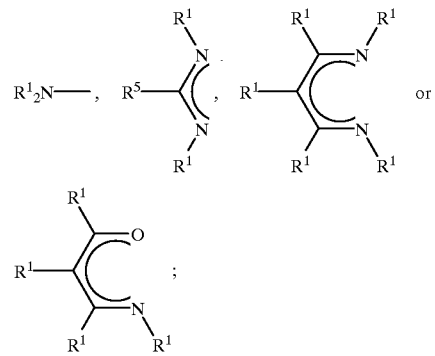

$R^1$ is independently each occurrence hydrogen, a hydrocarbyl group, a tri(hydrocarbyl)silyl group, or a tri(hydrocarbyl)silylhydrocarbyl group, said $R^1$ groups containing up to 20 atoms not counting hydrogen;

$R^5$ is $R^1$ or $N(R^1)_2$; and two $R^1$ groups in T together or one or more $R^1$ groups in T together with $R^5$ may optionally be joined to form a ring structure.

* * * * *

UNITED STATES PATENT AND TRADEMARK OFFICE
CERTIFICATE OF CORRECTION

PATENT NO.    : 6,284,905 B1
DATED         : September 4, 2001
INVENTOR(S)   : Arthur J. Ashe, III et al.

It is certified that error appears in the above-identified patent and that said Letters Patent is hereby corrected as shown below:

Columns 83, 86, 91, 96, 99 and 104,
Formula 2, delete 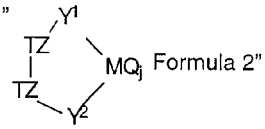 and insert therefor 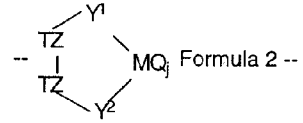

Column 105,
Line 44, insert -- wherein $R^4$ is trimethylsilyl, --.

Signed and Sealed this

Twentieth Day of January, 2004

JON W. DUDAS
*Acting Director of the United States Patent and Trademark Office*